United States Patent
Dority et al.

(10) Patent No.: US 12,280,379 B2
(45) Date of Patent: Apr. 22, 2025

(54) MOLECULAR DIAGNOSTIC ASSAY SYSTEM

(71) Applicant: Cepheid, Sunnyvale, CA (US)

(72) Inventors: Douglas B Dority, Santa Cruz, CA (US); Tien Phan, Sunnyvale, CA (US); David Fromm, Sunnyvale, CA (US); Richard J. Casler, Jr., Sunnyvale, CA (US); Dustin Dickens, Santa Clara, CA (US); Stuart Morita, Sunnyvale, CA (US); Matthew Piccini, Sunnyvale, CA (US)

(73) Assignee: Cepheid, Sunnyvale, CA (US)

( * ) Notice: Subject to any disclaimer, the term of this patent is extended or adjusted under 35 U.S.C. 154(b) by 238 days.

(21) Appl. No.: 18/054,729

(22) Filed: Nov. 11, 2022

(65) Prior Publication Data

US 2023/0166263 A1 Jun. 1, 2023

Related U.S. Application Data

(62) Division of application No. 16/738,944, filed on Jan. 9, 2020, now Pat. No. 11,524,301, which is a division
(Continued)

(51) Int. Cl.
*B01L 7/00* (2006.01)
*B01L 3/00* (2006.01)
(Continued)

(52) U.S. Cl.
CPC ............ *B01L 7/52* (2013.01); *B01L 3/50273* (2013.01); *G01N 35/00871* (2013.01);
(Continued)

(58) Field of Classification Search
CPC . B01L 7/52; B01L 3/50273; G01N 35/00871; G01N 35/1016; G01N 35/1095; G01N 33/4875; H02P 6/182; H02P 27/06
See application file for complete search history.

(56) References Cited

U.S. PATENT DOCUMENTS 5,045,187 A * 9/1991 Suchanek ................ C02F 1/42
            210/278
6,374,684 B1   4/2002 Dority
            (Continued)

FOREIGN PATENT DOCUMENTS

CA        2853471 A1    1/2015
DE    102013114041 A1   6/2015
            (Continued)

OTHER PUBLICATIONS

Gamazo-Real, et al., Position and Speed Control of Brushless DC Motors Using Sensorless Techniques and Application Trends, Sensors 2010, 10, 6901-6947.
(Continued)

*Primary Examiner* — Patrick C Williams
(74) *Attorney, Agent, or Firm* — Potomac Law Group, PLLC; Reza Mollaaghababa; Michael J. Bastian

(57) ABSTRACT

Improved sub-assemblies and methods of control for use in a diagnostic assay system adapted to receive an assay cartridge are provided herein. Such sub-assemblies include: a brushless DC motor, a door opening/closing mechanism and cartridge loading mechanism, a syringe and valve drive mechanism assembly, a sonication horn, a thermal control device and optical detection/excitation device. Such systems can further include a communications unit configured to wirelessly communicate with a mobile device of a user so as to receive a user input relating to functionality of the system with respect to an assay cartridge received therein and relaying a diagnostic result relating to the assay cartridge to the mobile device.

9 Claims, 66 Drawing Sheets

Related U.S. Application Data of application No. 15/217,920, filed on Jul. 22, 2016, now Pat. No. 10,562,030.

(60) Provisional application No. 62/196,845, filed on Jul. 24, 2015.

(51) Int. Cl.

| | |
|---|---|
| *G01N 33/487* | (2006.01) |
| *G01N 35/00* | (2006.01) |
| *G01N 35/10* | (2006.01) |
| *H02P 6/182* | (2016.01) |
| *H02P 27/06* | (2006.01) |

(52) U.S. Cl.
CPC ..... *G01N 35/1016* (2013.01); *G01N 35/1095* (2013.01); *H02P 6/182* (2013.01); *H02P 27/06* (2013.01); *B01L 2200/025* (2013.01); *B01L 2200/04* (2013.01); *B01L 2200/0647* (2013.01); *B01L 2200/143* (2013.01); *B01L 2300/023* (2013.01); *B01L 2300/027* (2013.01); *B01L 2300/0663* (2013.01); *B01L 2300/14* (2013.01); *B01L 2300/1822* (2013.01); *B01L 2300/1827* (2013.01); *B01L 2300/1894* (2013.01); *B01L 2400/0436* (2013.01); *B01L 2400/0439* (2013.01); *B01L 2400/0496* (2013.01); *G01N 33/4875* (2013.01); *G01N 2035/00019* (2013.01); *G01N 2035/00316* (2013.01); *G01N 2035/00356* (2013.01); *G01N 2201/0221* (2013.01); *G01N 2201/0256* (2013.01); *G01N 2800/00* (2013.01)

(56) References Cited

U.S. PATENT DOCUMENTS

| | | | |
|---|---|---|---|
| 6,660,228 B1 | 12/2003 | Chang et al. | |
| 6,818,185 B1 | 11/2004 | Petersen et al. | |
| 8,048,386 B2 | 11/2011 | Dority et al. | |
| 8,084,980 B2* | 12/2011 | Carlson | G05B 19/19 |
| | | | 318/40 |
| 8,133,451 B2 | 3/2012 | Yuan | |
| 9,295,778 B2 | 3/2016 | Kamen et al. | |
| 9,744,300 B2 | 8/2017 | Kamen et al. | |
| 9,914,968 B2 | 3/2018 | Chiang et al. | |
| 2005/0031322 A1* | 2/2005 | Boyle | A61M 16/205 |
| | | | 128/204.21 |
| 2007/0152515 A1* | 7/2007 | Motherway | H02K 41/031 |
| | | | 310/152 |
| 2009/0078898 A1* | 3/2009 | Sasaki | F02D 41/0077 |
| | | | 251/129.11 |
| 2010/0050749 A1 | 3/2010 | Yuan | |
| 2011/0000182 A1* | 1/2011 | Lasker | F03G 6/068 |
| | | | 60/39.24 |
| 2011/0268628 A1 | 11/2011 | Warhurst et al. | |
| 2011/0276744 A1 | 11/2011 | Sengupta et al. | |
| 2011/0313789 A1 | 12/2011 | Kamen et al. | |
| 2012/0190589 A1 | 7/2012 | Anderson et al. | |
| 2013/0184676 A1 | 7/2013 | Kamen et al. | |
| 2013/0281965 A1 | 10/2013 | Kamen et al. | |
| 2014/0098252 A1 | 4/2014 | Chang et al. | |
| 2015/0007500 A1 | 1/2015 | Schatz | |
| 2015/0190810 A1* | 7/2015 | Glezer | F16K 11/0743 |
| | | | 436/180 |
| 2016/0228876 A1 | 8/2016 | Chu | |

FOREIGN PATENT DOCUMENTS

| | | |
|---|---|---|
| JP | 2011/187295 A | 9/2011 |
| JP | 5523876 | 6/2014 |
| JP | 6800864 | 12/2020 |
| WO | 2011/132219 A1 | 10/2011 |
| WO | 2014/039703 A1 | 3/2014 |
| WO | 2015/086445 A1 | 6/2015 |

OTHER PUBLICATIONS

Viramontes, "BLDC Motor Control with Hall Effect Sensores Using the 9S08MP," Freescale Semiconductor, Apr. 1, 2010, 13 pages.
Keeping, "Controlling Sensorless, BLDC Mortors via Back EMF," Digi-key Electronics, Jun. 13, 2013, www.digikey.nl/en/articles/techzone/2013/jun/controlling-sensorless-blsc-motors-via-back-emf.
European Communication pursuant to Article 94(3) EPC for European Application No. 16745978.3 dated Mar. 27, 2024.
International Preliminary Report on Patentability an Written Opinion issued in PCT/US2016/043763, dated Jan. 30, 2018.
International Search Report and Written Opinion issued in PCT/US2016/043763, dated Dec. 5, 2016.

* cited by examiner

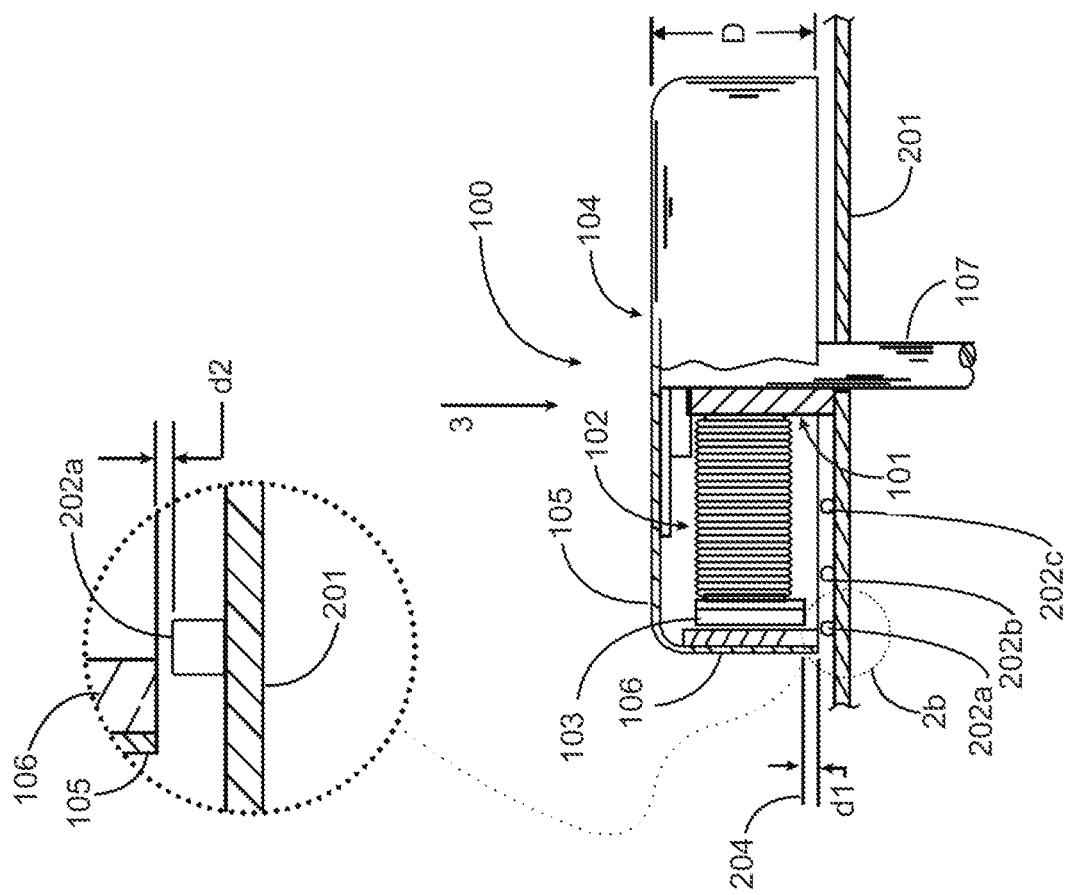
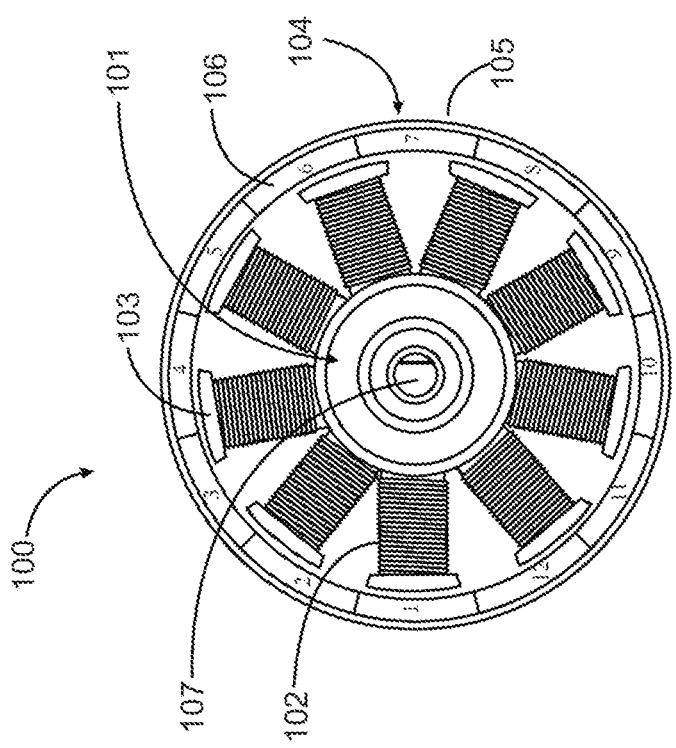
FIG. 2B
FIG. 2A

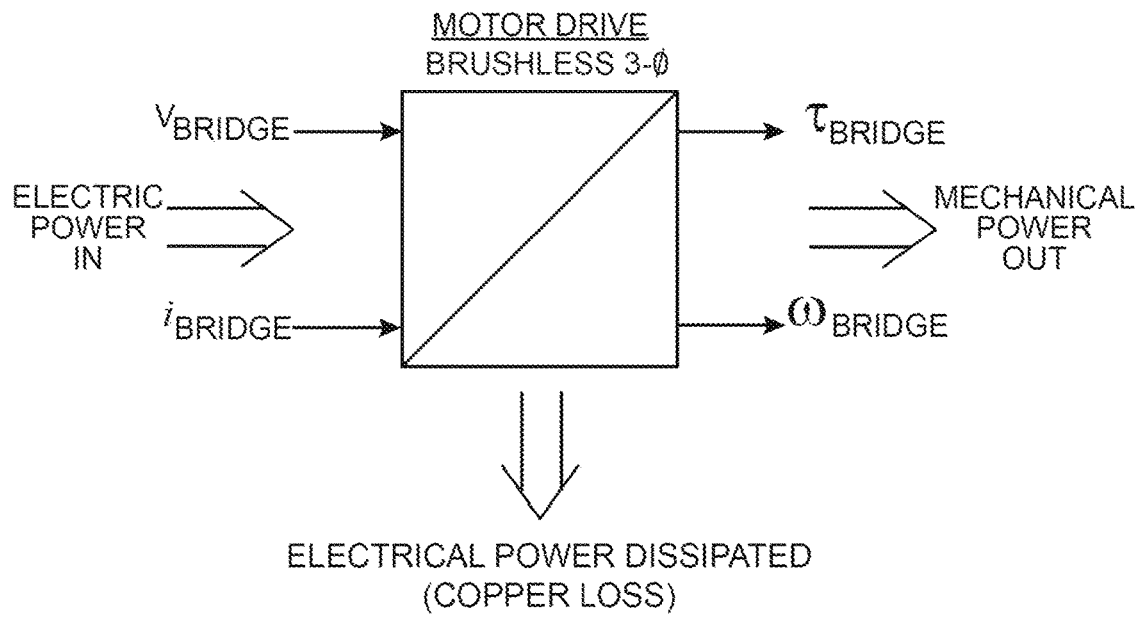
FIG. 3A
*q*-d MOTOR MODELS
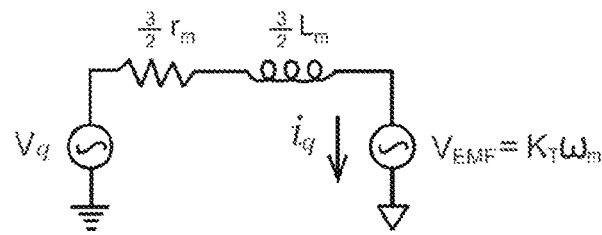
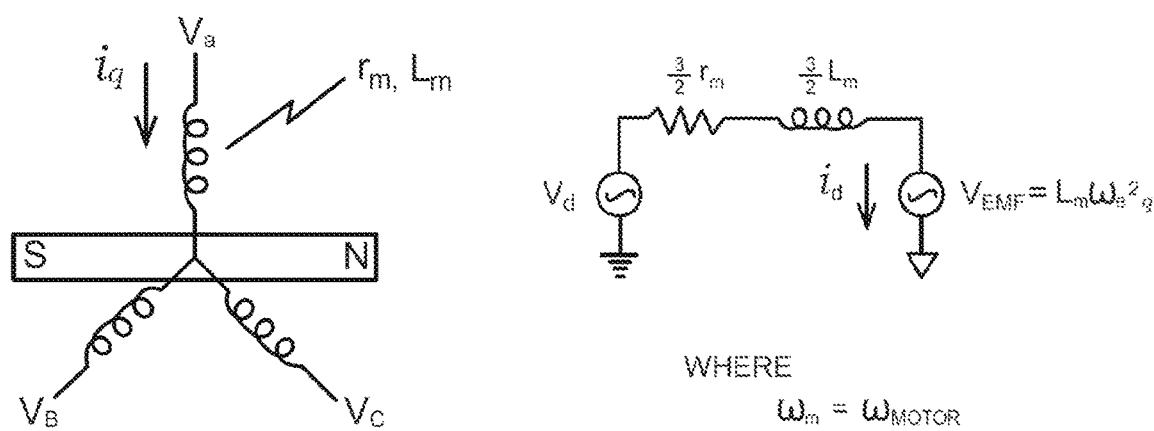
FIG. 3B
FIG. 3C

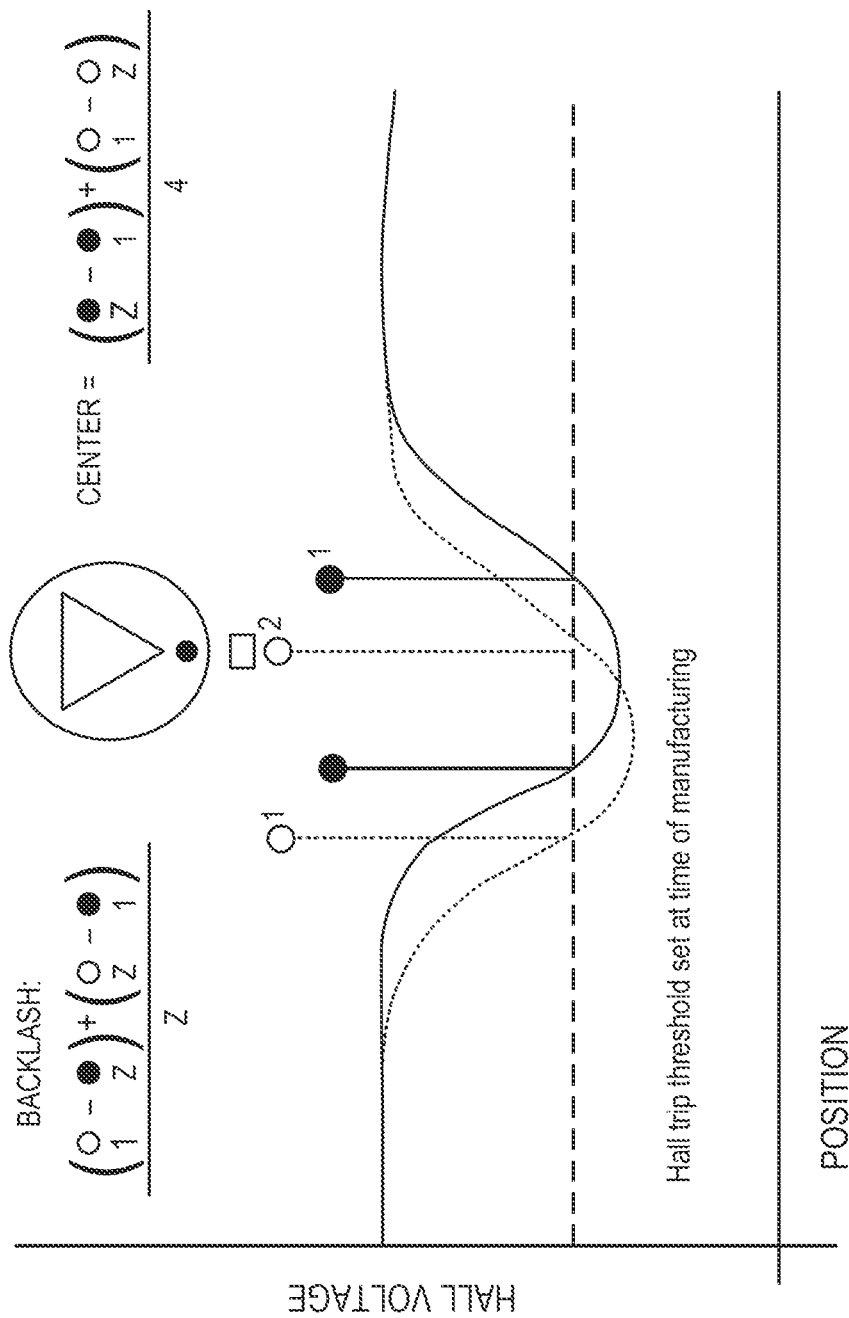

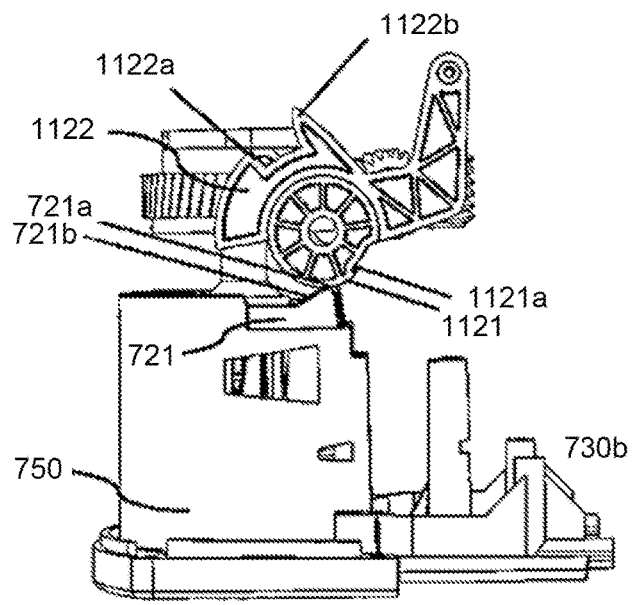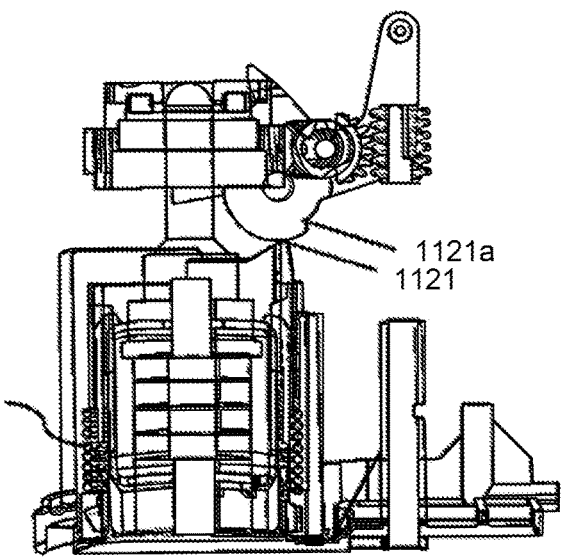
FIG. 11A-1    FIG. 11A-2
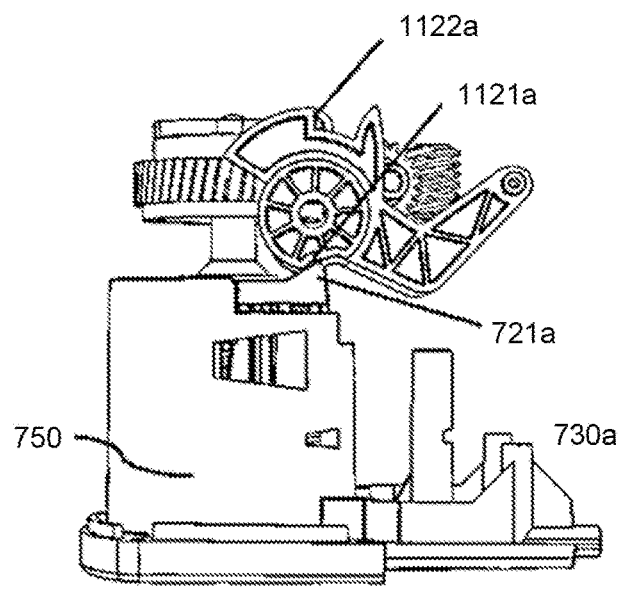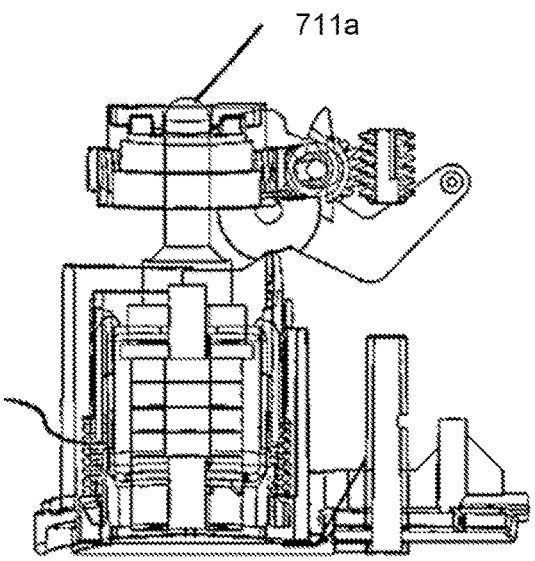
FIG. 11B-1    FIG. 11B-2

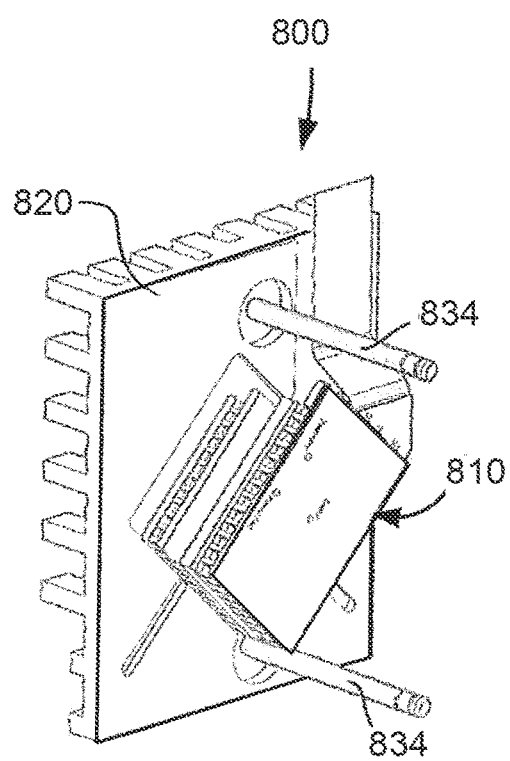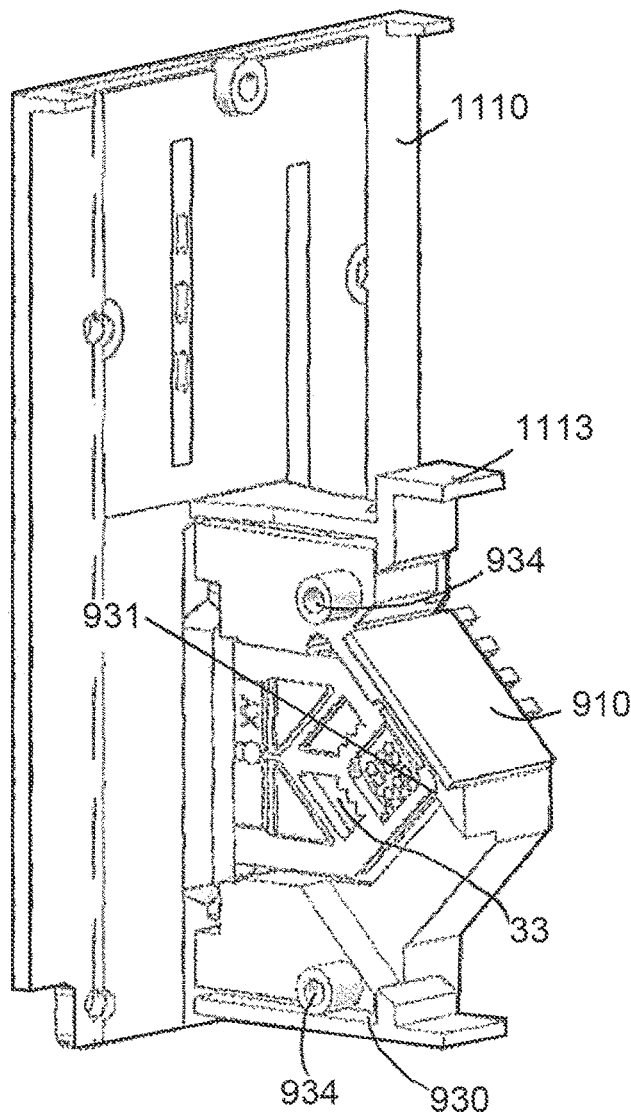
FIG. 23A
FIG. 23B

Thermo-cycling performance for cycles 1-5 (top) remains constant after 5,000 cycles (cycles 4,995-5,000 at bottom).

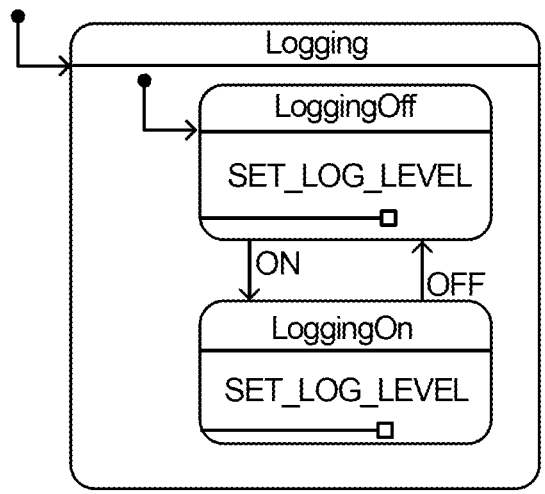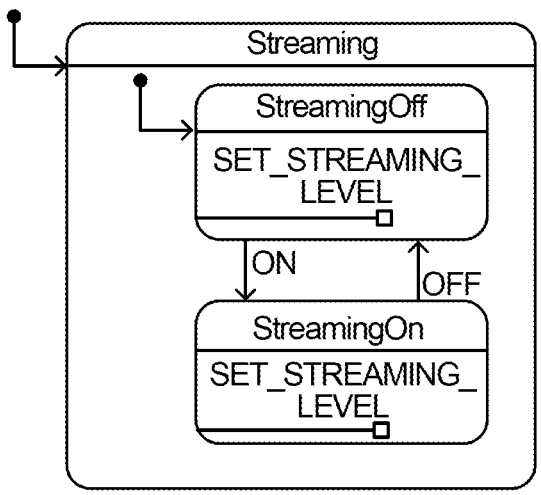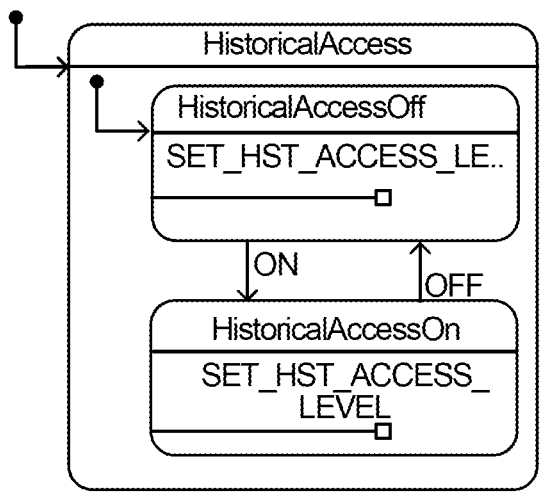
FIG. 41-4

MOLECULAR DIAGNOSTIC ASSAY SYSTEM

CROSS-REFERENCES TO RELATED APPLICATIONS

This application is a divisional of U.S. application Ser. No. 16/738,944, filed Jan. 9, 2020 which is a divisional of U.S. application Ser. No. 15/217,920, filed Jul. 22, 2016 which claims the benefit of priority of U.S. Provisional Patent Application No. 62/196,845 entitled "Molecular Diagnostic Assay System," filed on Jul. 24, 2015; the entire contents of which are incorporated herein by reference.

This application is generally related to U.S. patent application Ser. No. 15/217,902, filed Jul. 22, 2016, entitled "Thermal Control Device and Methods of Use" now U.S. Pat. No. 10,544,966; U.S. patent application Ser. No. 15/217,893, filed Jul. 22, 2016, entitled "Encoderless Motor with Improved Granularity and Methods of Use" now U.S. Pat. No. 10,348,225; U.S. patent application Ser. No. 13/843,739 entitled "Honeycomb tube," filed on Mar. 15, 2013, now U.S. Pat. No. 9,914,968; U.S. patent application Ser. No. 13/828,741 entitled "Remote Monitoring of Medical Devices," filed on Mar. 14, 2013; U.S. Pat. No. 8,048,386 entitled "Fluid Processing and Control," filed Feb. 25, 2002; and U.S. Pat. No. 6,374,684 entitled "Fluid Control and Processing System," filed Aug. 25, 2000; each of which is incorporated herein by reference in its entirety for all purposes.

BACKGROUND OF THE INVENTION

Technological advancements have made today's world an increasingly connected environment. While air travel allows an ordinary person to travel around the globe from one continent to another within one day, it may also permit rapid spread of contagious pathogens and expose the global population to deadly diseases with potentially devastating consequences. In the recent past the outbreaks of Severe Acute Respiratory Syndrome (SARS), Middle East Respiratory Syndrome (MERS), and Ebola hemorrhagic fever serve as examples of how a public health event that originated in one area on one continent can quickly evolve into a significant global concern. The highly mobile nature of today's world demands reliable diagnostic tools to provide real-time results and to facilitate early detection and immediate response to any potential epidemics.

On the other hand, there remain many remote and under-developed areas in this world where health care is not readily available to local residents. Inadequate accessibility to health care facilities such as hospitals and clinics, or even health product/service retailers (e.g., drug stores), seriously hinders any effort to achieve timely diagnosis and treatment of patients, especially those suffering from an infectious disease, making it difficult to properly assess the risk of an epidemic or to effectively contain an epidemic from rapid spreading. Thus, there exists a pressing need for new and improved diagnostic tools that are highly mobile, capable of performing complex molecular testing to generate rapid, reliable, and accurate diagnostic results, regardless of location, whether in a health care facility, neighborhood clinic, retail service provider, or in a resource-limited setting where electrical power, communication (e.g., internet), traditional health care services and/or health care professionals may not be routinely available.

The present inventors have developed a highly sophisticated yet completely portable and surprisingly easy to use molecular diagnostic assay system that fulfills the aforementioned needs. Improved upon existing molecular diagnostic assay systems (e.g., Cepheid's GeneXpert® system), the new molecular diagnostic assay system described herein includes a medical diagnostic device, which is optionally powered by battery, typically small in size and light in weight, thus permitting complete portable use at any location where patients may be, away from hospitals, laboratories, or even drug stores. The diagnostic device is capable of performing fully automated molecular diagnostic assays (optionally for detecting multiple pathogens at the same time), rapidly obtain accurate results (typically within 1 or 2 hours and as fast as 15-20 minutes). It is easy to operate, using one or more pre-manufactured assay cartridges one can quickly obtain test results indicating whether a patient is carrying particular pathogen(s), or afflicted with a particular disease state.

This newly designed molecular diagnostic assay system also includes components that provide secure cloud-based connectivity for conveying the diagnostic results from the portable testing device to a remote reporting system, which may be a centralized data collection or processing center, or mobile devices such as hand-held devices used by a physician or a patient to receive a diagnostic report. With such cloud-supported connectivity, data sharing can take place virtually instantaneously, not only allowing physicians to start treating patients without any delay but also enabling monitoring and reporting of any potential epidemic at a large scale.

These important features circumvent the current limitations that tend to prevent or hinder early diagnosis and effective treatment of patients in poor, remote areas where health care facilities are few and diagnostic testing capability is scarce. This newly designed molecular diagnostic assay system is the first true point-of-care diagnostic tool possessing the strength of rapid deployment and full operation in virtually any environment. It truly brings diagnostic testing to people, regardless of where they are. The combination of its deployability, its rapid and accurate diagnostic functionality, its technical sophistication yet ease of operation, and its cloud-based connectivity makes this new molecular diagnostic assay system the ultimate solution for the emerging markets and the revolutionary trend-setter that defines the future of medical diagnostic testing.

BRIEF SUMMARY OF THE INVENTION

In one aspect, the invention provides an improved diagnostic assay system. Such systems can include improvements pertaining to various subassemblies including: a door drive assembly, a syringe drive and a valve drive, a sonication horn, a thermal and optical detection assembly, and a device management/communication system. It is appreciated that any of these subassemblies can be included in such a diagnostic assay system separately or in combination with any other subassembly to provide improved performance aspects as described herein.

In some embodiments, the invention includes a diagnostic assay system adapted to receive an assay cartridge (also referred to occasionally as a "sample cartridge" or "test cartridge"). Such systems can include any one or combination of the various features and sub-assemblies described herein.

In some embodiments, the diagnostic assay system includes a brushless DC (BLDC) motor operatively coupled with, for example, any of a door opening/closing mechanism and cartridge loading system, a syringe drive, and/or a valve drive.

In some embodiments, the diagnostic assay system includes a door opening/closing mechanism cooperatively coupled with a cartridge loading mechanism and driven by a backdriveable transmission mechanism.

In some embodiments, the diagnostic assay system includes a syringe drive operatively coupled with a n-phase BLDC motor and controlled based at least in-part on monitored current draw of the BLDC motor.

In some embodiments, the diagnostic assay system includes a valve drive mechanism operatively coupled with a n-phase BLDC motor based at least in-part on a voltage signal provided by n voltage sensors of the BLDC without use of any encoder hardware or position sensors.

In some embodiments, the diagnostic assay system includes a sonication horn engageable with an assay cartridge for lysing of biological material within the assay cartridge and operatively coupled with a controller configured to control sonication based at least in-part on a frequency providing a highest output amplitude as a resonant frequency.

In some embodiments, the diagnostic assay system includes a thermal control device having a first thermoelectric cooler thermally engageable with a reaction vessel (also occasionally referred to as a "reaction tube") of the assay cartridge and at least one other thermal manipulation device thermally coupled with the first thermoelectric cooler and controlled so as to increase efficiency of the first thermoelectric cooler to facilitate rapid thermal cycling of the reaction vessel between a first and second temperature with the first thermoelectric cooler.

In some embodiments, the diagnostic assay system includes an optical excitation/detection block mountable relative the reaction vessel so as to emit excitation energy into a fluid sample within the reaction vessel at a substantially orthogonal angle from which excitation is detected through one or more edges (minor face) and/or a major face of the reaction vessel.

In some embodiments, the diagnostic assay system includes a communications unit configured to wirelessly communicate with a mobile device of a user so as to receive a user input relating to functionality of the system with respect to an assay cartridge received therein and relaying a diagnostic result relating to the assay cartridge to the mobile device.

Some embodiments of the invention relate to a door operating system for a diagnostic assay system. The system can include a chassis of the diagnostic assay system. A brushless DC (BLDC) motor can be coupled to the chassis of the diagnostic assay system. A back drivable transmission can be operable by the BLDC motor. A door can be movable relative to the chassis of the diagnostic assay system from a closed position to an open position (and from an open position to a closed position). The BLDC motor can be configured to operate the back drivable transmission based on current measurements of the BLDC motor, the current measurements being associated with back-driving events against the back drivable transmission.

Some embodiments of the invention relate to a method for operating a door opening/closing system for a diagnostic assay system. In the method, a command can be received to open a cartridge receiving door of the diagnostic assay system. A brushless DC (BLDC) motor coupled to a back drivable transmission can be operated to open the door from a closed position (and vice versa), the back drivable transmission being operationally coupled to the door and a cartridge loading mechanism. A first back-driving event occurring against the back drivable transmission can be detected, based on monitoring of the current. Based on detecting the first back-driving event, operation of the BLDC motor to place the door in an open position can be ceased, and an aspect of the cartridge loading mechanism can be placed into position for accepting an assay cartridge.

Some embodiments of the invention relate to a system for operating a syringe for a diagnostic assay system. The system can include a chassis of a diagnostic assay system. A brushless DC (BLDC) motor can be coupled to the chassis of the diagnostic assay system. A back drivable lead screw can be operable by the BLDC motor. A plunger rod can be operable by the lead screw to engage a plunger tip in a syringe passage of the assay cartridge. The BLDC motor can be configured to operate the lead screw based on monitoring current draw of the BLDC motor, the current being associated with pressure changes within the removable assay cartridge.

Some embodiments of the invention relate to a method for operating a syringe for a diagnostic assay system. A command to power a brushless DC (BLDC) motor can be received. The BLDC motor can be operable to turn a back drivable lead screw. A plunger rod can be coupled to and moveable by the lead screw. Power to the BLDC motor can be applied to move the plunger rod to engage a plunger tip within a syringe passage of an assay cartridge. At least one current associated with operation of the BLDC motor can be monitored to determine a quality of the removable assay cartridge. A change in the current of the BLDC motor can be detected. Operation of the BLDC motor can be altered within the removable assay cartridge based on detecting the change in the current.

Some embodiments of the invention relate to a horn assembly having an ultrasonic horn and a horn housing that engages with the disposable assay cartridge through a movable mechanism that moves the ultrasonic horn between a disengaged or retracted position to facilitate loading and ejection of the assay cartridge from the diagnostic device module and an engaged or advanced position to pressingly engage the horn against a sonication chamber of the assay cartridge to facilitate lysis of biological cells within the chamber as part of a diagnostic assay, which may include but is not limited to a polymerase chain reaction analysis. In some embodiments, the movable mechanism includes a spring or biasing mechanism and a cam that engages a wedge surface of the horn housing to effect movement of the horn between the lowered and raised positions. In some embodiments, movement of the horn assembly is effected by an actuator common to other movable components, such as a loading/ejection arm and a cartridge module door so as to provide efficient coordinated movements of components within the diagnostic device module.

Some embodiments of the invention relate to a horn having an ultrasonic horn and at least one piezo-electric actuator(s) controlled under closed-loop feedback. In some embodiments, the horn comprises a control circuit that utilizes sinusoidal control and phase matching for control of resonant frequency. These features ensure in-phase vibration between the piezo-electric actuator(s) so as to provide consistent, robust delivery of ultrasonic energy with an ultrasonic horn having reduced size and power requirements than would otherwise be feasible.

Some embodiments of the invention relate to a method for operating a valve drive mechanism. A command can be received to power a brushless DC (BLDC) motor coupled to the chassis to move a valve drive to a particular position. The valve drive can be configured to rotate positions of a valve body of a removable assay cartridge. A transmission can be coupled between the BLDC motor and the valve drive. The BLDC motor does not include any positional sensors or encoder hardware, but can include a plurality of Hall-effect sensors. The BLDC motor can be powered to rotate a shaft of the BLDC motor a particular number of turns to move the valve drive to the particular position based on a sinusoidal signal generated by the Hall-effect sensors.

Some embodiments relate to a system for operating a valve drive mechanism. The system can include a valve drive mechanism chassis. A brushless DC (BLDC) motor can be coupled to the chassis. The BLDC motor does not include any positional or encoder hardware, but can include a plurality of Hall-effect sensors. A transmission can be coupled to BLDC motor. A valve drive can be coupled to the transmission. The valve drive can be configured to rotate positions of a valve body of a removable assay cartridge. Position of the valve drive output can be determined based on analyzing a sinusoidal signal generated by the Hall-effect sensors.

Some embodiments of the invention relate to a diagnostic device which can include a Thermal Optical Subassembly ("TOS") which comprises a thermal control device component and an optical excitation/detect component. In some embodiments, the thermal control device includes a thermoelectric cooler ("TEC") component that performs thermal cycling of a reaction vessel. The optical component excitation/detect component performs excitation and optical detection for a target analyte with improved control, rapidity and efficiency. In some embodiments, the TOS includes mounting components for interfacing the thermal control device with the optical component and defines a cavity for receiving a reaction vessel having a prepared fluid sample for performing an assay for a target analyte. In some embodiments, the mounting components provide the thermal control device and optical component in proximity to the reaction vessel so as to perform thermal cycling for amplification, excitation and optical detection of the target analyte simultaneously or in rapid succession. In some embodiments, the reaction vessel comprises a micro-array or a plurality of separate reaction wells and/or a pre-amplification chamber within the reaction vessel. In some embodiments, the TOS includes one or more mechanisms that move the thermal control device so as to pressingly engage at least one surface of the reaction vessel when positioned within the diagnostic device so as to improve efficiency of thermal cycling. In some embodiments, the TOS is integrated with one or more printed circuit boards (PCB), processors and controllers so as to coordinate thermal cycling and optical excitation/detection according to a particular assay. In some embodiments, the TOS includes a sensor for detecting proximity of a reaction vessel or associated sample assay cartridge to facilitate positioning of the thermal control device and/or optical component relative the reaction vessel or operation thereof.

Some embodiments of the invention relate to a thermal control device which can include a first TEC having an active face and a reference face; a second TEC having an active face and a reference face; and a thermal capacitor or thermal interposer disposed between the first and second TECs such that the reference face of the first TEC is thermally coupled with the active face of the second TEC through the thermal capacitor. In some embodiments a thermal interposer is positioned between the first and second TEC devices. In some embodiments, the thermal interposer acts as a thermal capacitor. In some embodiments, the thermal control device includes a controller operatively coupled to each of the first and second TECs, the controller configured to operate the second TEC concurrent with the first TEC so as to increase the speed and efficiency in operation of the first TEC as a temperature of the active face of the first TEC changes from an initial temperature to a desired target temperature.

Some embodiments of the invention relate to an optical component that can include an optical excitation block and an optical detect block positioned on an optical mount that is configured to receive a reaction vessel. In some embodiments, the reaction vessel comprises two opposing major planar walls spaced apart from each other by minor planar walls, wherein at least two of the minor planar walls are offset from each other by about 90 degrees. In some embodiments, the optical excitation block is positioned to transmit excitation energy into the reaction vessel through one of the minor walls, and the optical detection block is positioned for detection along a major planar surface of the reaction vessel. In some embodiments, the excitation and detection occurs through opposing minor walls of the reaction vessel. In some embodiments, the optical excitation and optical detection components are orthogonal to one other. The optical components are adapted with a relatively low numerical aperture (e.g. low angular divergence) as compared to conventional systems. Such a configuration provides a larger detection volume with lower numerical angles, thereby providing improved optical sensitivity and facilitating optical alignment.

In another aspect, the TOS includes a sensor for detecting proximity and/or location as well as the identity of an assay cartridge or reaction vessel relative the TOS. In some embodiments, the sensor is a near field communication sensor adapted to detect when an assay cartridge has been loaded into the diagnostic device (also referred to occasionally as a "diagnostic module") of the diagnostic assay system, identify the assay, and link the cartridge to a sample identifier. In some embodiments, the TOS includes a controller for coordinating operation of the thermal control device and the optical module in response to the sensor.

Some embodiments of the invention relate to a method of managing a diagnostic assay system with a mobile device. At a mobile device, user input can be received for controlling functionality of a diagnostic device. In response to receiving the user input, with the mobile device, control information can be sent to the diagnostic assay device. At the mobile device, data (e.g., medical data) can be received from the diagnostic assay device. The data can be relayed to a server without storing or descripting the data.

Some embodiments of the invention relate to a diagnostic assay device having a communications subsystem. The system can include a diagnostic component. A processor communicatively can be coupled with the communications subsystem and the diagnostic component. The processor can be configured to cause the diagnostic assay device to wirelessly receive, using the communications subsystem, a device command from a mobile device. The processor can also be configured to wirelessly send, using the communications subsystem, a device command response to the mobile device. The processor can also be configured to conduct a test using the diagnostic component. The processor can also be configured to wirelessly send, using the communications subsystem, encrypted diagnostic information (e.g., medical information), indicative of a result of the test, to a remote server.

BRIEF DESCRIPTION OF THE DRAWINGS

FIGS. 2A-2C are perspective views of a brushless DC (BLDC) motor, according to some embodiments of the invention.

FIGS. 3A-3C are diagrams of models for determining torque output of a BLDC motor, according to some embodiments of the invention.

FIG. 6C is a graph relating an output signal to valve drive position, according to some embodiments of the invention.

FIGS. 11A1-2 to 11B1-2 illustrates side and cross-section views of a horn assembly in a disengaged position and a engaged position, respectively, in accordance with some embodiments of the invention.

FIGS. 23A-B illustrates an exemplary thermal control device component configured to interface with an optical mount of an example TOS in accordance with some embodiments of the invention.

FIGS. 41-1 to 41-4 are diagrams illustrating various states of the Hierarchical System Machine (HSM) component, according to some embodiments of the invention.

DETAILED DESCRIPTION OF THE INVENTION

I. System Overview

Figure 1A:
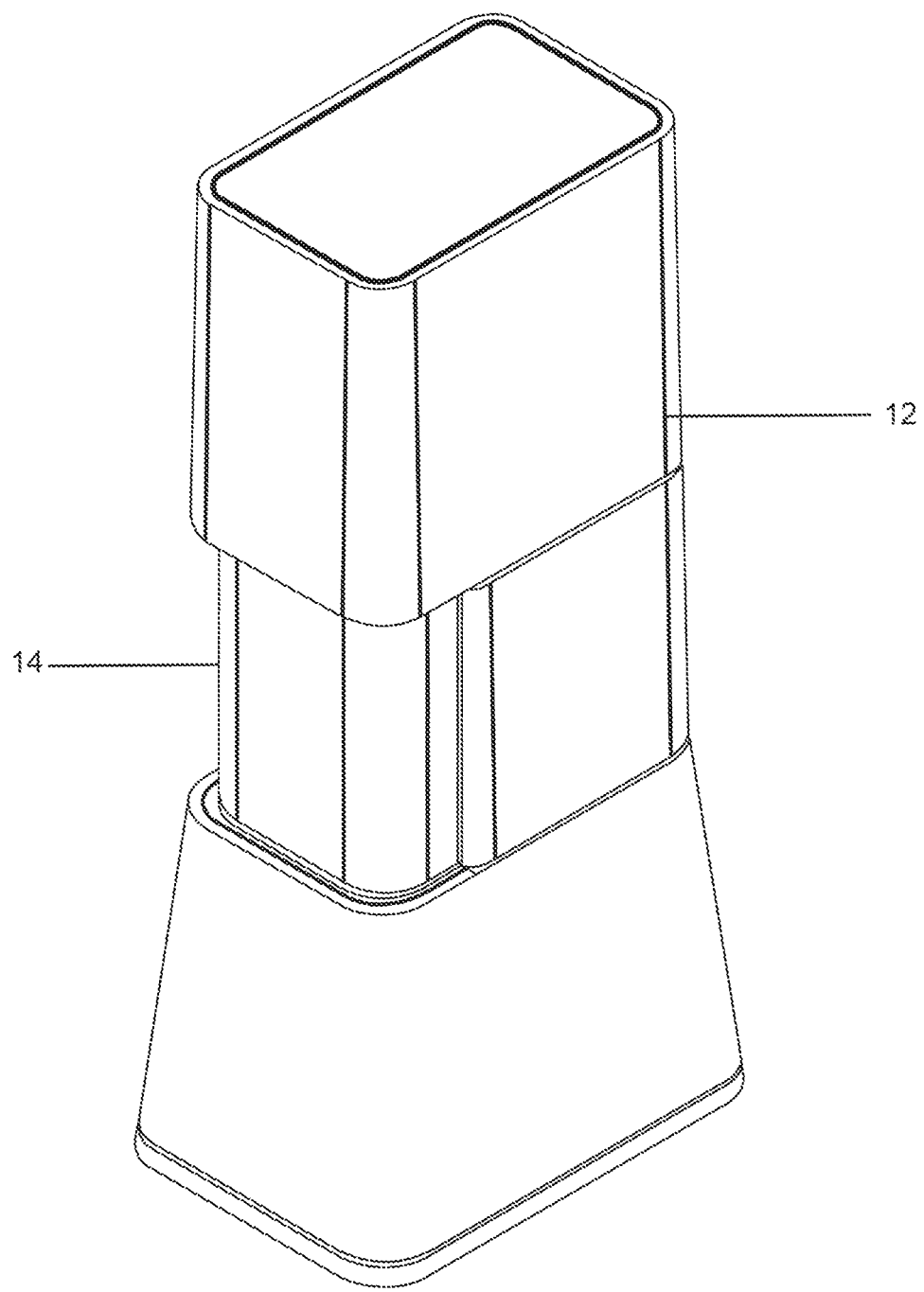
FIG. 1A is a perspective view of a diagnostic assay system, according to some embodiments of the invention.

FIG. 1A shows a perspective view of a system 10 for testing a biological sample, according to embodiments of the invention. The compact form factor of the system 10 provides a portable sample testing device that can communicate wirelessly or directly (wired) with a local computer or cloud-based network. As such, the system 10 can be advantageously used for point-of-care applications including mobile diagnostic centers, in emerging countries, and in physician office labs.

The system 10 is usable with a disposable assay cartridge, which is configured to accept a biological sample and adapted for performing a particular assay. The system and cartridges are highly flexible and can be used to detect a variety of analytes, including nucleic acid and protein. Non-limiting exemplary analytes that can be detected using the system and assay cartridges includes, bacteria, viruses, and disease specific markers for a variety of pathogenic disease states including Health Associated Infections (MRSA, *C. difficile*, Vancomycin resistant enterococcus (VRE), Norovirus), Critical Infectious Diseases (MTB/RIF, Flu, RSV, EV), Sexual Health (CT/NG, GBS), oncology (e.g., breast or bladder cancer) and Genetics (FII/FV). In some embodiments, the system 10 can identify the type of cartridge via integrated near field communication ability (e.g. RFID, laser scanning), and thus apply the appropriate assay routine to the cartridge. In some embodiments, cartridge identification uses Bluetooth technology, RFID tags, barcoding, QR labels, and the like.

Once a assay cartridge is physically inserted within and initialized by the system 10, the system will perform the functions of specimen processing, which can in some embodiments include sample preparation, nucleic acid amplification, and an analyte detection process. Results of the detection process can be uploaded wirelessly or directly by wire to a local computer or cloud based network. Advantageously, the local computer can be a wireless communication device, such as a tablet or cellular phone, having a software application specifically designed to control the system and communicate with a network.

The system 10 can be powered by an external power source, but can feature an uninterruptable power supply (e.g. batteries) in case of power disruption or field use. The uninterruptable power supply (UPS) allows for field use of the system, and in some embodiments can provide power to the system for at least one day, preferably up to two days. In some embodiments, the UPS allows for up to four hours of continuous operation. As shown in this external view, the system 10 can include an outer shell 12 and a door 14 for accepting an assay cartridge (not shown). Different styles of the outer shell 12 can be configured as needed by a particular user. Typically, outer shell 12 is formed of a substantially rigid material so as to protect and support the components within, for example, a hardened polymer or metal construction. Although not shown here, in some embodiments the outer shell 12 can be heavily ruggedized (armored) for field use, or as shown here made decorative for physician office use.

Figure 1B:
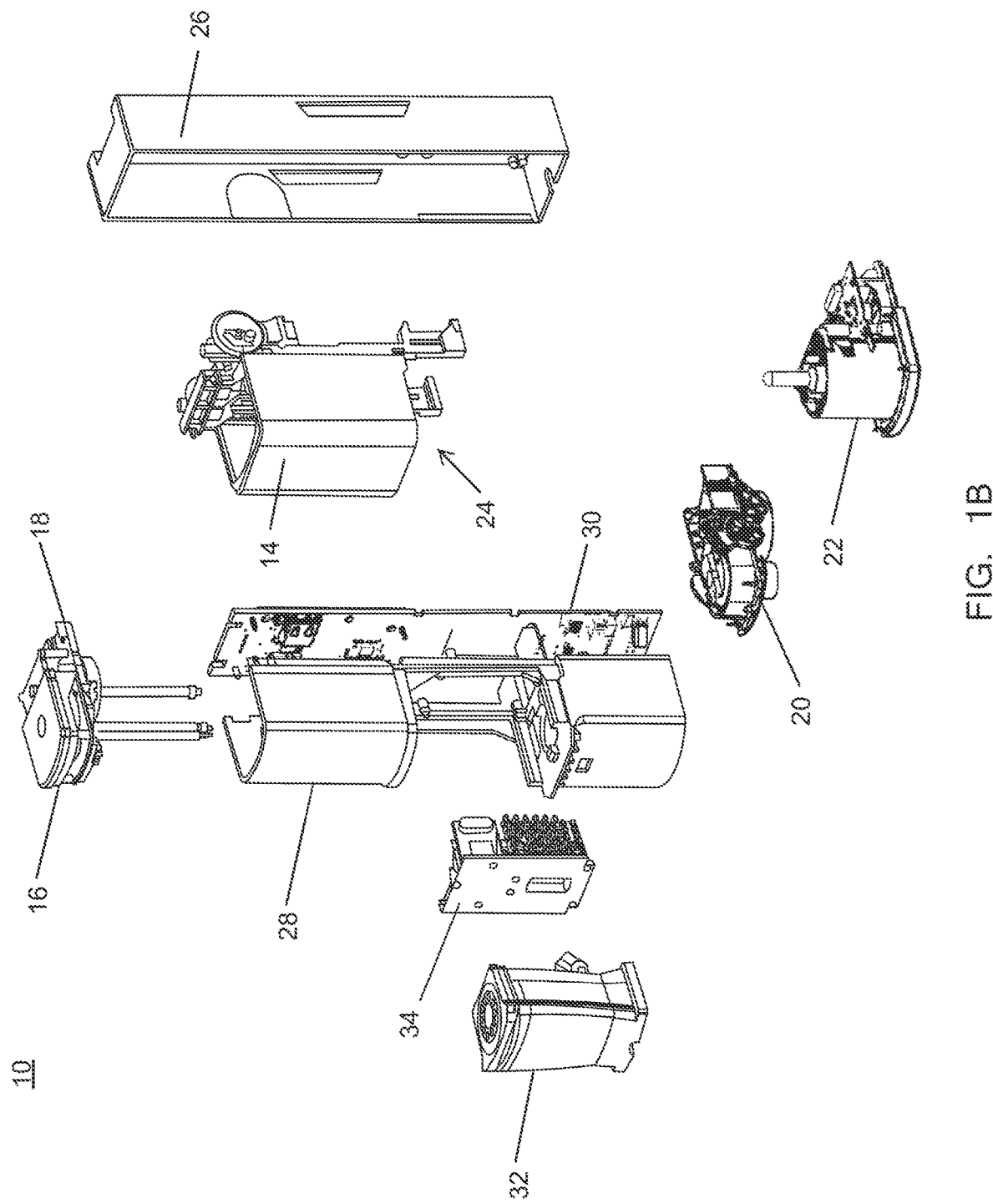
FIG. 1B is an exploded view of a diagnostic assay system, according to some embodiments of the invention.

FIG. 1B shows an exploded view of the system 10 (without the outer shell) and with major subsystems depicted outwardly. An overview of the subsystems is provided below. Additional details of each subsystem are described in the following sections.

Various sub-systems are disclosed that make use of brushless DC (BLDC) motors. Generally, each motor can have a stator assembly that is mounted to a printed circuit board (PCB) substrate, and can include a back drivable transmission mechanism, such as a lead screw. In some embodiments, such BLDC motors make use of analog sensors (e.g., Hall-sensors) for determining angular positioning and force-based current monitoring as a triggering tool. Such BLDC motors can include a rotor with multiple magnets disposed thereon and mounted to a stator on a substrate with at least as many sensors as phases of the motor. The three sensors are positioned such that the displacement of the rotor can be controlled based on the linear portions of measurements from the sensors, thereby providing improved resolution and granularity without requiring use of any position-based sensors or encoder hardware. Thus, the BLDC motors described herein do not require use of encoder hardware and their associated drive trains do not require use of position sensors. For example, the system can include a syringe drive mechanism 16 that includes a brushless BLDC motor having an output shaft that is mated to a back drivable lead screw. The lead screw drives a plunger rod that can interface with a plunger tip of a removable assay cartridge. Such a syringe drive mechanism 16 can share a PCB 30 with a door drive mechanism 18. The door drive mechanism also includes a BLDC motor having an output shaft that is mated to a back drivable lead screw. The motors of the syringe drive mechanism 16 and door drive mechanism 18 are shown directly mounted to opposite sides of a PCB board, however, this is not critical and both motors can be mounted to the same side. In some embodiments, each motor can be mounted to its own PCB. It is advantageous to utilize such BLDC motors as the improved resolution and granularity allows for improved accuracy and efficiency, and further allows for further miniaturization of mechanisms driven by such motors. It is appreciated, however, that use of such BLDC motors is not required and that any of the mechanisms described herein could also be driven by conventional type motors if desired, but additional sensors and/or circuitry may be required for some embodiments.

As mentioned above, the BLDC motor is unique in that includes a plurality of Hall-effect sensors, but does not include any traditional encoder hardware. In some embodiments, the syringe drive mechanism and door drive mechanism, and associated subsystems, do not include position sensors. In some embodiments, the angular position of the rotor and output shaft of the BLDC can be solely derived from the sinusoidal wave output of the analog sensors and the circuitry on the PCB. Thus, traditional position sensors (e.g. encoders, optical sensors, etc.) are not required for use in conjunction with the BLDC motors as used in the instant invention. In order for the BLDC motor to provide smooth torque production, motor control techniques such as sine-wave commutation can be implemented. Further, pulse-width modulation implementation can be used to center the drive voltages to achieve high speed operation.

In addition, because the lead screws of the mechanisms are back drivable, force-based end-of-travel detection can be used to determine start and stop points for driving the mechanisms. Force-based end-of-travel detection can be derived by monitoring the current of the BLDC motors, e.g., the current of a bridge circuit, which will deviate (increase or decrease) from a norm when a force-based event occurs. Hence, this deviation can be used as a trigger event to start, stop, reverse, slow down, and/or speed up a BLDC motor. For example, in the case of the syringe drive mechanism 16, current sensing can be correlated to pressure, and thus be used to deliver a consistent or intentionally varying pressure to the plunger rod by tuning the RPM of the associated BLDC motor. This alleviates the need for an in-line pressure sensor to monitor cartridge pressure.

Valve drive mechanism 20 can make similar use of the same type of BLDC motor. In some embodiments, the valve drive mechanism 20 can include a worm drive gear train, which ultimately outputs to a turntable like valve drive for rotating the valve of a removable assay cartridge. In some embodiments, the worm drive mechanism is not back drivable as in the aforementioned syringe drive and door drive mechanisms. However, the same type of Hall-effect position determination and force base triggering (current monitoring) can be used for the valve drive mechanism. For example, if turning the valve drive unexpectedly requires substantially less or more current, then such an event can be indicative of a jam or failure of an assay cartridge. Here, force base triggering can be used to sense a cartridge integrity malfunction.

Sonication horn mechanism 22 is partially integrated with the valve drive mechanism 20. The sonication horn mechanism 22 can apply a programmable sonication power for a programmable duration to the cartridge, for example, in order to lyse a target sample within the cartridge. In some embodiments, the sonication horn mechanism 22 can employ a resonant piezo-electric actuator to apply vibration at a frequency of about 30 kHz or greater, about 40 kHz or greater, such as about 50 kHz (e.g. 50.5 kHz). The sonication horn mechanism 22 includes a control circuit that uses the phase of measured current in relation to the voltage excitation to determine the resonant frequency. The frequency can be adjusted by the control circuit to maintain a preset phase relationship. In some embodiments, the amplitude of the voltage excitation can be continually adjusted to maintain the commanded power level. Based on these functions, the control circuit can maximize power output of the horn.

The system 10 also includes a door drive and cartridge loading system 24 that is powered by the door drive mechanism 18. The lead screw of the door drive mechanism 18 outputs power to the door drive and cartridge loading system 24 to both open and close the door 14 as well as engage and intake an assay cartridge 32.

A rear chassis portion 26 and a front chassis portion 28 provide structural support for the system 10, as well as mounting provisions for the other subsystems. The chassis portions are generally elongated to provide a smaller overall footprint for the system 10, and enable portability of the system 10. In some embodiments, the system can have a foot print of. 9.1"×3.0"×4.2", and an approximate weight of 2.2 lbs. The elongated circuit board or PCB 30 generally matches the foot print of the chassis portions. The PCB 30 includes most or all of the processors, sub-processors, memory, and control circuits required to control the system 10. However, the aforementioned BLDC motors can be integrated with their own respective printed circuit boards that have control circuits that connect separately to the PCB 30. The PCB 30 also includes communication circuit aspects (e.g. near field communication circuits, USB, wireless) as well as a power supply circuit.

The system 10 is compatible with various types of assay cartridges 32, which are generally configured for receiving and holding a sample of material, such as a bodily fluid (e.g., blood, urine, salvia) or solid (e.g., soil, spores, chemical residue) that is liquid soluble. The assay cartridge 32 can be a walled structure having one or more fluid channels and connection ports. The assay cartridge 32 may be relatively small, such that it can easily be hand-held, portable, and/or disposable. Examples of such cartridges (useable with the system 10) are disclosed in U.S. Pat. No. 6,660,228, Int'l Pub. No. WO 2014052671 A1, U.S. Pat. No. 6,374,684, which are each incorporated by reference herein for all purposes.

The assay cartridge 32 can include a reaction vessel 33 extending outward from the rear, which interfaces with a thermal cycling and detection module 34. The module 34 includes one or more apparatuses configured to deliver energy to, and also remove energy from, an aspect of the assay cartridge 32. Such an apparatus can include a dual thermoelectric cooler. The module 34 also includes one or more detection aspects, as discussed in further detail below.

II. Brushless DC (BLDC) Motor Architecture

FIG. 2A is a plan view diagram illustrating elements of a brushless DC (BLDC) motor 100, for use with some embodiments of the invention. Further details of the BLDC motor can be found at commonly assigned U.S. Provisional Application No. 62/195,449, filed Jul. 22, 2015, and entitled "Simple Centroid Implementation of Commutation and Encoding for DC Motor," which is hereby incorporated by reference for all purposes.

In one aspect, the BLDC motor includes a rotor and stator configured to produce a smoothly varying Hall-effect voltage without any need for filtering or noise reduction. In some embodiments, this feature is provided by use of permanent magnets within the rotor that extend a distance beyond the magnetic core of the stator. In some embodiments, the BLDC motor includes as many Hall-effect sensors as phases of the motor, which are positioned such that the motor can be controlled based on substantially only the linear portion of the measured voltage patterns received from the sensors. In some embodiments, this includes spacing the sensors radially about the stator such that the linear portions of the measured voltage waveforms intersect. For example, a three-phase BLDC can include three Hall-effect sensors spaced 40 degrees radially from each other, thereby allowing the system to control a position of the sensor within an increment of 40 degrees.

In some embodiments, the motor comprises an internal stator assembly 101 having nine pole teeth extending radially from center, each pole tooth ending in a pole shoe 103, and each pole tooth having a winding providing an electromagnetic coil 102. The motor further comprises an external rotor 104 having an external cylindrical skirt 105 and twelve permanent magnets 106 arranged with alternating polarity around the inner periphery of the skirt 105. The permanent magnets are shaped to provide a cylindrical inner surface for the rotor with close proximity to outer curved surfaces of the pole shoes. The BLDC motor in this example is a three-phase, twelve pole motor. Controls provided, but not shown in FIG. 2A, switch current in the coils 102 providing electromagnetic interaction with permanent magnets 106 to drive the rotor, as is well-known in the art.

It should be noted that the number of pole teeth and poles, and indeed the disclosure of an internal stator and an external rotor are exemplary, and not limiting in the invention, which is operable with motors of a variety of different designs.

FIG. 2B is a side elevation view, partly in section, of the motor of FIG. 2A, cut away to show one pole tooth and coil of the nine, ending in pole shoe 103 in close proximity to one of the twelve permanent magnets 106 arranged around the inner periphery of cylindrical skirt 105 of external rotor 104. The pole teeth and pole shoes of stator assembly 101 are a part of the core, and define a distal extremity of the core at the height of line 204. Stator assembly 101 is supported in this implementation on a substrate 201, which in some embodiments is a printed circuit board (PCB), which PCB can comprise controls and traces for managing switching of electrical current to coils 102, providing electromagnetic fields interacting with the fields of permanent magnets 106 to drive the rotor. The PCB as substrate can also comprise control circuitry for encoding and commutation. Rotor 104 engages physically with stator 101 by drive shaft 107, which engages a bearing assembly in the stator to guide the rotor with precision in rotation. Drive shaft 107 in this implementation passes through an opening for the purpose in PCB 107, and can be engaged to drive mechanical devices.

Three linear Hall-effect sensors 202a, 202b, and 202c are illustrated in FIG. 2B, supported by substrate 201, and positioned strategically according to some embodiments of the invention to produce a variable voltage pattern that can be used in a process to encode angular position of the rotor and provide commutation for motor 100. In FIG. 2B the overall height of skirt 105 of rotor 104 is represented by dimension D. Dimension d1 represents extension of the distal extremity of the rotor magnets below the distal extremity of the core at line 204. In conventional motors there is no reason or motivation to extend this edge below the extremity of the core, particularly since this can increase the height of the motor and require increased clearance between the rotor and substrate. In fact, the skilled artisan would limit dimension D so there is no such extension, as the added dimension would only add unnecessary cost and bulk to a conventional motor. Furthermore, in conventional motors at the distal extremity of the rotor, at the height of or above the distal extremity of the core, switching of current in coils 102 creates a considerable field effect, and a signal detected by a Hall-effect sensor placed to sense permanent magnets at that position would not produce a smoothly varying Hall-effect voltage. Rather, the effect in a conventional motor is substantially noise corrupted. The conventional approach to this dilemma is to introduce noise-filtering, or more commonly to utilize an encoder.

Extending the rotor magnets below the distal extremity of the iron core avoids the corrupting effect of the switching fields from the coils of the stator on the signal detected by the Hall-effect sensors. The particular extension d1 will depend on several factors specific to the particular motor arrangement, and in some embodiments will be 1 mm or more (e.g. 2 mm, 3 mm, 4 mm, 5 mm, 6 mm, or greater), while in some embodiments the extension will be less than 1 mm. In some embodiments, the distance is a function of the size of the permanent magnets and/or the strength of the magnetic field. In some embodiments, as detailed herein, 1 mm of extension is sufficient to produce a sinusoidal signal of varying voltage without noise or saturation. Placement of the Hall-effect sensors at a separation d2 to produce a Hall-effect voltage produces a smoothly variable voltage, devoid of noise. In some embodiments, the Hall-effect sensors produce a smoothly variable DC voltage in the range from about 2 volts to about 5 volts devoid of noise or saturation. The dimension d2 may vary depending on choice of sensor, design of a rotor, strength of permanent magnets in the rotor, and other factors that are well known to persons of skill in the art. A workable separation is readily discovered for any particular circumstance, to avoid saturation of the sensor and to produce a smoothly variable DC voltage substantially devoid of noise.

Figure 2D:
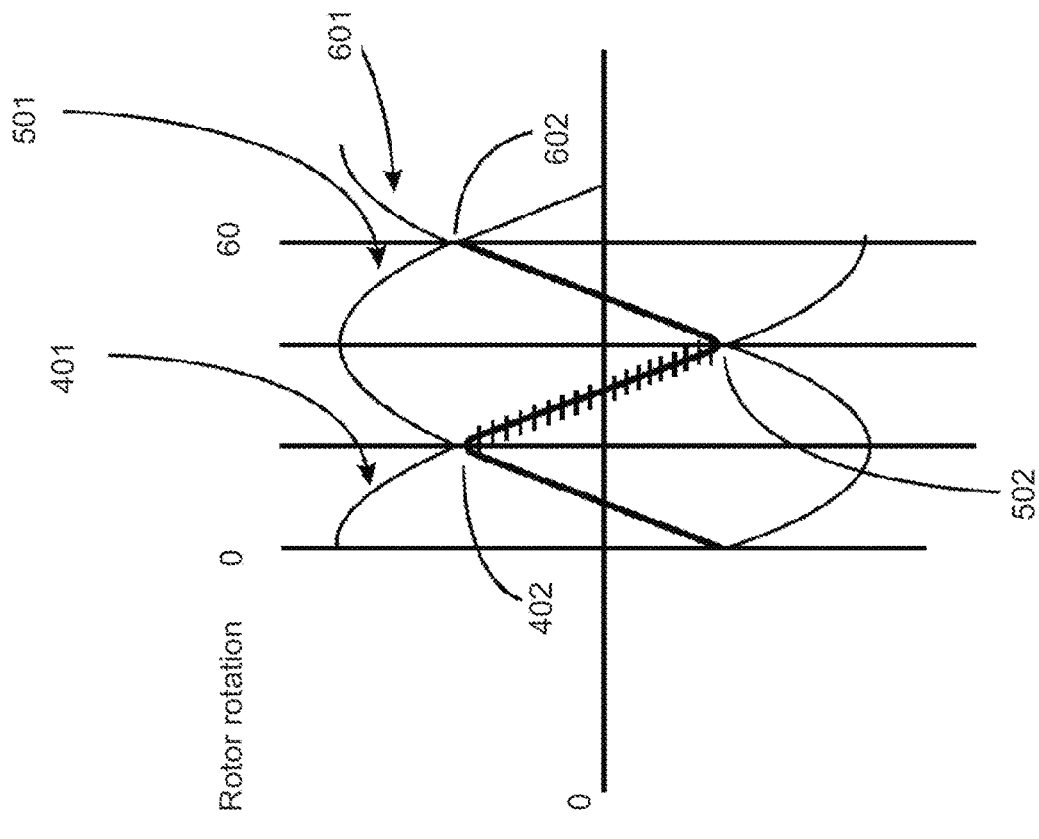
FIG. 2D is a graph of a sinusoidal variable voltage output pattern of a BLDC motor, with additional indicia to illustrate a process for encoding the mechanical angular position of the rotor of the motor according to some embodiments of the invention.
Figure 2C:
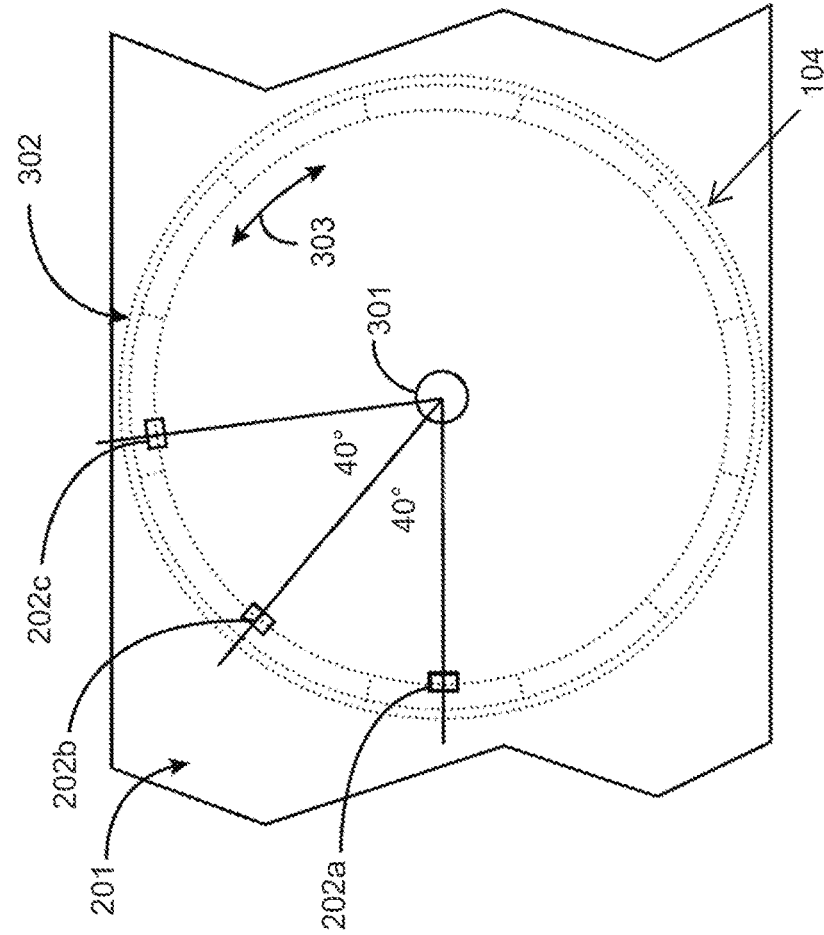

FIG. 2C is a plan diagram of a portion of substrate 201 taken in the direction of arrow 3 of FIG. 2B, showing placement of Hall-effect sensors 202a, 202b, and 202c relative to the distal edge of rotor 104, which may be seen in FIG. 2B to extend below the distal edge of the core by dimension d1. In FIG. 2C the rotation track of rotor 104 including the twelve permanent magnets 106 is shown in dotted outline 302. The rotor rotates in either direction 303 depending on details of commutation.

As illustrated in this non-limiting exemplary embodiment, each of Hall-effect sensors 202a, 202b, and 202c is positioned radially beneath the distal edge of the rotor magnets, just toward the inside of the central track of the rotating magnets. Hall-effect sensor 202b is located forty degrees arc from Hall-effect sensor 202a along the rotating track of the magnets of the rotor. Similarly, Hall-effect sensor 202c is located a further forty degrees around the rotor track from Hall-effect sensor 202b.

FIG. 2D illustrates three voltage patterns 401, 501 and 601 produced by passage of permanent magnets 106 of rotor 104 over Hall-effect sensors 202a, 202b, and 202c in a three-phase BLDC motor. A sinusoidal variable voltage pattern 401 produced by passage of permanent magnets 106 of rotor 104 over Hall-effect sensor 202a. The 0 degree starting point is arbitrarily set to be at a maximum voltage point. Three complete sine waveforms are produced in one full 360 degree revolution of the rotor. Voltage pattern 501 produced by passage of permanent magnets 106 of rotor 104 over Hall-effect sensor 202b. Further, a substantially noise free sinusoidal variable voltage pattern 501 produced by passage of permanent magnets 106 of rotor 104 over Hall-effect sensor 202b. As Hall-effect sensor 202b is positioned at an arc length of 40 degrees from the position of Hall-effect sensor 202a, sinusoidal pattern 501 is phase-shifted by 120 degrees from that of sinusoidal pattern 401. Yet further, a substantially noise free sinusoidal variable voltage pattern 601 produced by passage of permanent magnets 106 of rotor 104 over Hall-effect sensor 202c. As Hall-effect sensor 202c is positioned at an arc length of 40 degrees from the position of Hall-effect sensor 202b, sinusoidal pattern 601 is phase-shifted by 120 degrees from that of sinusoidal pattern 501. The patterns repeat for each 360 degree rotation of the rotor.

The three voltage patterns 401, 501 and 601 each have substantially the same max and min peaks, as the Hall-effect sensors are identical, and are sensing the same magnetic fringe fields at the same distances. Moreover, patterns 401, 501 and 601 intersect at multiple points, points 402, 502, and 602 being examples. Notably, the pattern segments between intersection points are substantially straight lines, and may be seen to provide an endless, continuing sequence of connected straight-line segments. Further, zero-crossing points for each straight line segment, and max and min peaks for each pattern may be sensed and recorded.

FIG. 2D further illustrates two straight line segments between crossing points 402, 502, and 602. As a non-limiting example, the segment between crossing points 402 and 502 is shown divided into 20 equal-length segments, which may conveniently be done by sensing the voltage at crossing points 402 and 502, and simple division. Because the physical rotation of the rotor, in this example, from one pattern intersection to another is twenty degrees of motor rotation, each voltage change by the calculated amount then represents 20/20, that is, 1.00 degrees of rotation of the rotor. This is a relatively gross example to merely illustrate the method. In some embodiments of the invention, circuitry on PCB 201 senses the crossing points and divides by an 11-bit analog to digital converter (ADC) between the intersections. This provides 2048 counts. In this implementation the mechanical rotational translation of rotor 205 for each count is about 0.0098 degree. Resolution of the system can be increased (or decreased) by using an ADC with a higher (or lower) bit resolution. For example, using an 8-bit ADC would resolve each count to about 0.078 degrees, a 16-bit ADC would resolve each count to 0.00031 degrees, and using a 20-bit ADC would resolve each count to about 0.00002 degrees. Alternatively, increasing or decreasing the number of poles will correspondingly increase or decrease the resolution of the system.

In some embodiments, the invention provides for a high degree of accuracy and precision for mechanisms driven by motor 100. In the non-limiting example described above using an 11-bit ADC, the motor position can be controlled to 0.0098 degree mechanical. Coupled with gear reduction extremely fine control of translation and rotation of mechanisms can be attained. In some embodiments, motor 100 is coupled to a translation drive for a syringe-pump unit to take in and expel fluid in diagnostic processes.

Figure 2E:
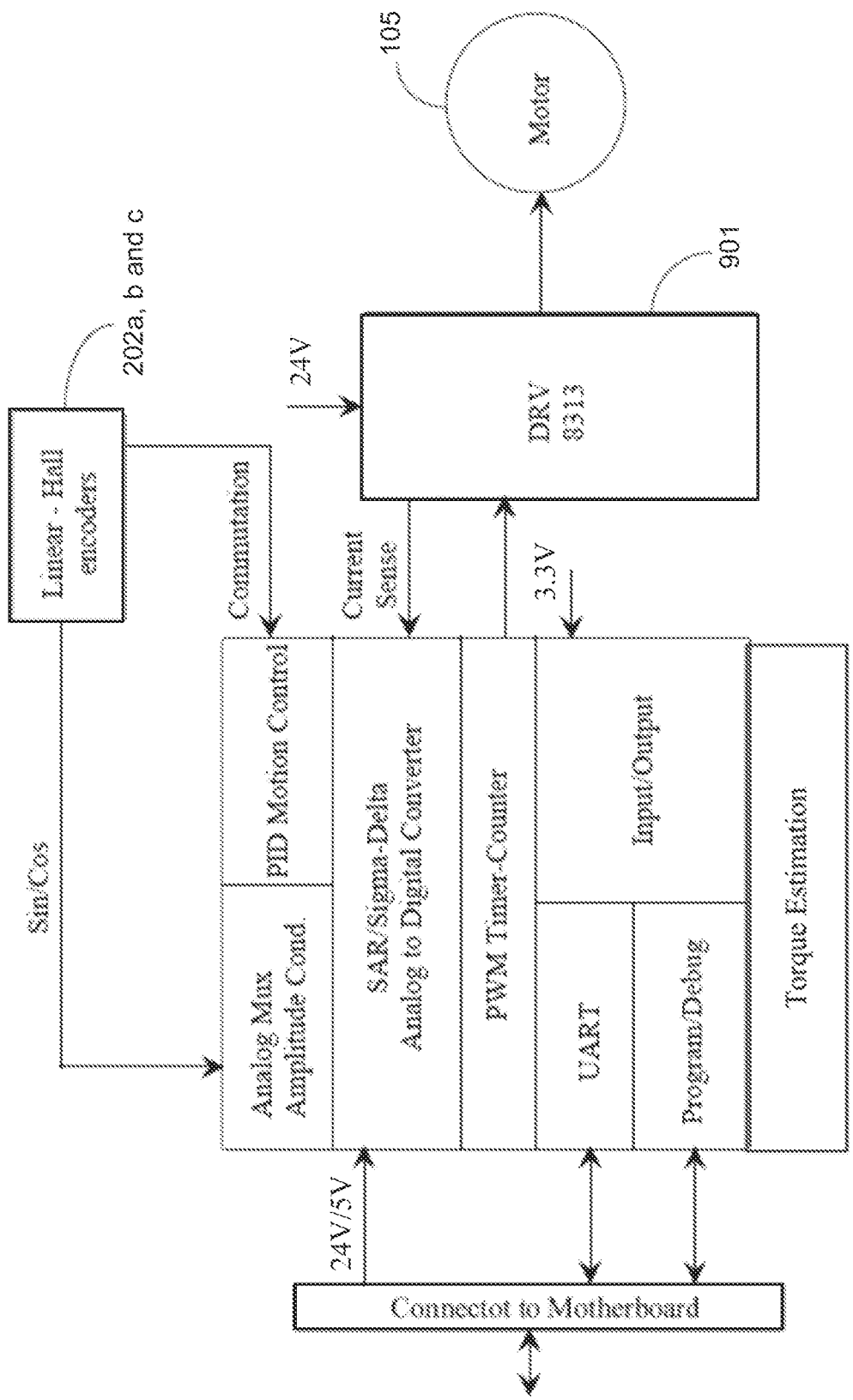
FIG. 2E is a circuit diagram for controlling a BLDC motor, according to some embodiments of the invention.

FIG. 2E is a diagram depicting circuitry in some embodiments of the invention for controlling motor 100 using the output of the Hall-effect sensors and the unique method of analyzing only the linear portions of phase-separated curves produced by the sensors, the linear portions divided into equal segments divided as described above. Output of the Hall-effect sensors 202a, 202b, and 202c is provided to a proportional-integral-derivative (PID) motion control circuitry for commutation purpose, and the waveforms produced by interaction of the rotor magnets with the Hall-effect sensors is provided to multiplexer circuitry as shown in FIG. 2E. As described above in the non-limiting exemplary embodiments, an ADC is used to produce the division of the straight portions of the phase-separated waveforms and motor 100, which can be driven by, for example, a DRV8313 Texas Instruments motor driver circuit. The skilled person will understand the circuitry is not necessarily unique, and will understand further that there are other arrangements of circuitry that might be used while still falling within the scope of the instant invention. In some embodiments the circuitry and coded instructions for sensing the Hall-effect sensors and providing motor encoding can be implemented in a programmable system on a chip (PSoC) on the PCB. The circuitry can also include a torque estimating circuit, which can be provided to estimate torque values generated by the motor based on current and voltage measurements taken at the PSoC, thus avoiding the need for additional force sensors throughout the greater system.

II. Motor Torque Estimation

In some embodiments, aspects of the BLDC motor 100 and control circuits can be used to detect torque without the need for extraneous sensors. This can be accomplished in different ways, for example by estimating torque based on the principle that the electrical power put forth into the BLDC motor is equal to the mechanical power extracted from the motor in addition to the electrical power dissipated by the motor (i.e. copper loss), as illustrated by the model shown at FIG. 3A. This principal is quantified by the following equation:

$$P_{in} = P_{out} + P_{CL}$$

Where dissipated power $P_{CL}$ is calculated from:

$$P_{CL} = \frac{3}{2} i_q^2 r_m$$

$$P_{CL} = \frac{3}{2} \frac{r_m}{K_t^2} \tau_m^2$$

or $$P_{CL} = \alpha_{CL} \tau_m^2,$$

with $$\alpha_{CL} = \frac{3}{2} \frac{r_m}{K_t^2}$$

Referring to the power balancing equation above, it logically follows that:

$$0 = P_{out} + P_{CL} - P_{in}$$

Substitution of the power variables results in the following balanced equation:

$$0 = (\alpha_{CL} * \tau_m^2) + (\omega_m * \tau_m) - (v_B * i_B)$$

Hence, solving for the motor torque $\tau_m$, the following equation results:

$$\tau_m = \frac{-\omega_m \pm \sqrt{\omega_m^2 - 4\alpha_{CL} v_B i_B}}{2\alpha_{CL}}$$

It follows that here are two possible calculated solutions for the motor torque, which are the most positive and most negative torque solutions generated by the preceding equation, using bridge current $i_B$, as shown below:

$$\hat{\tau}_{m1} = \frac{-\omega_m + \sqrt{\omega_m^2 - 4\alpha_{CL} v_B i_B}}{2\alpha_{CL}}$$

and $$\hat{\tau}_{m2} = \frac{-\omega_m - \sqrt{\omega_m^2 - 4\alpha_{CL} v_B i_B}}{2\alpha_{CL}}$$

Figures 1, 41:
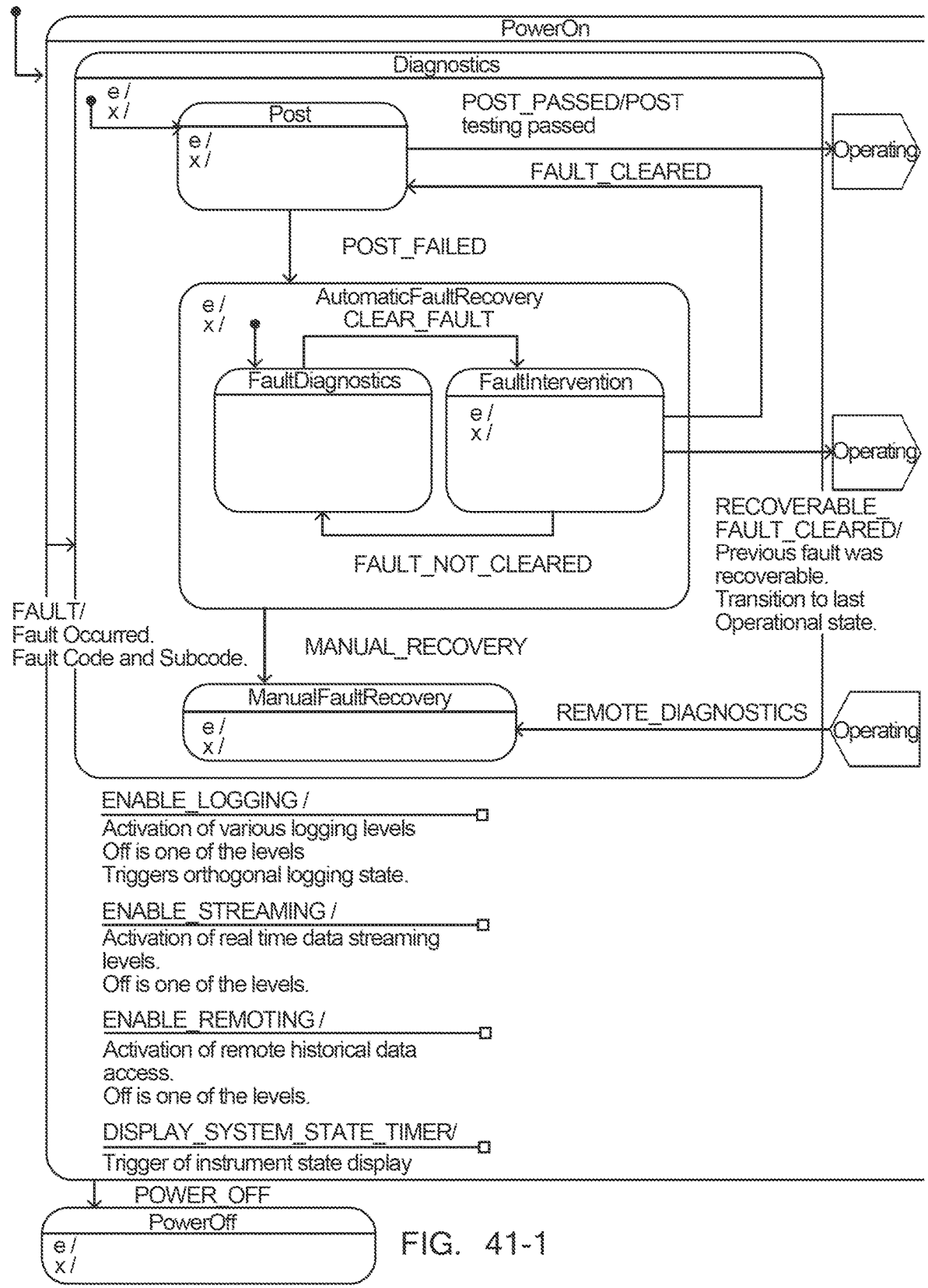
Figures 2, 41:
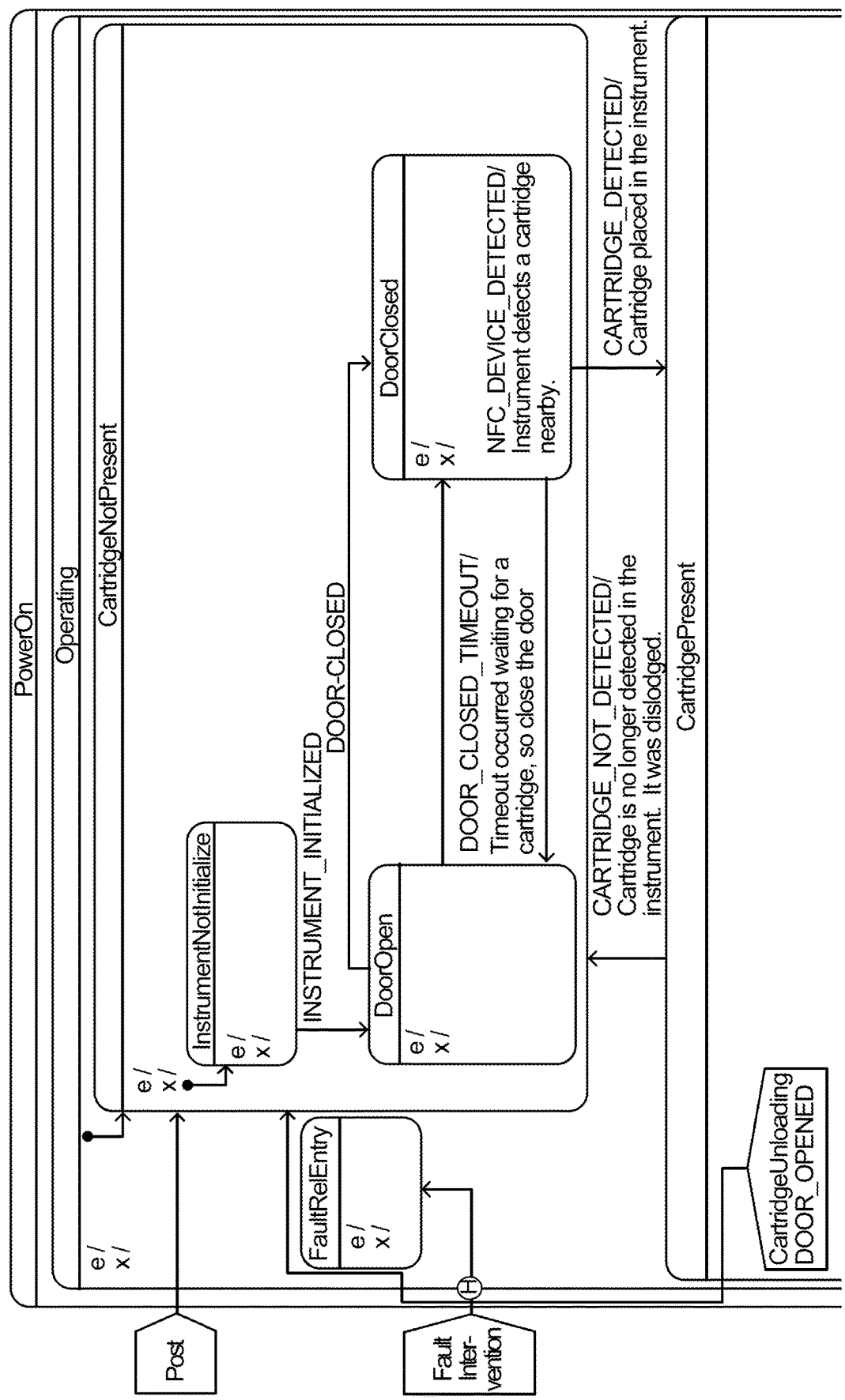
Figures 3, 41:
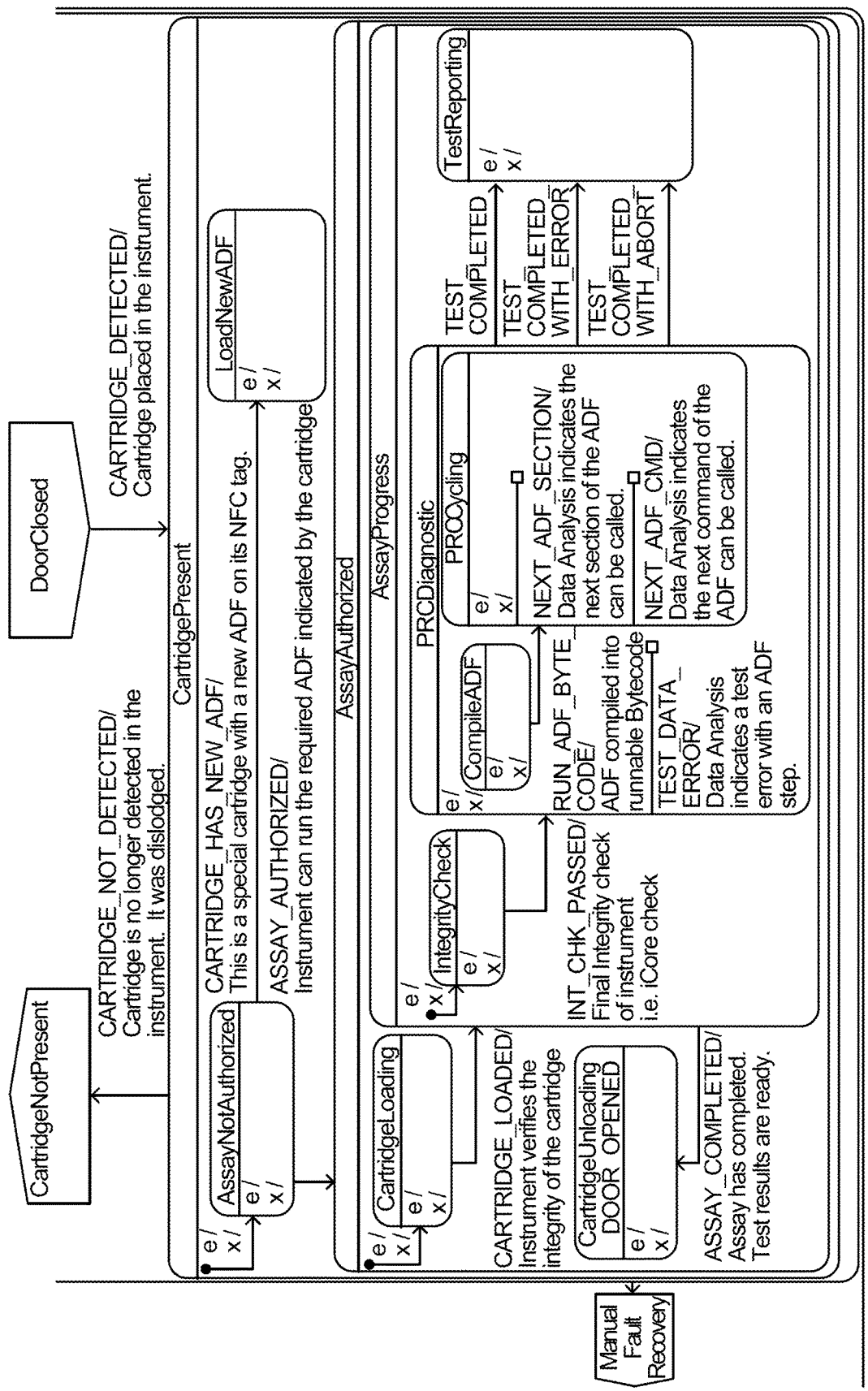

Given that torque is calculable from the motor constant and other variables, the motor torque can also be calculated using the motor constant $K_t$, as depicted at the motor models as shown at FIGS. 3B and 3C.

$$\hat{\tau}_m = K_t i_q \cong K_t \frac{v_q - v_{EMF}}{\frac{3}{2} r_m},$$

where $$V_{EMF} = K_t \omega_m$$

Thus, the calculated solution $\hat{\tau}_{m1}$ or $\hat{\tau}_{m2}$ that is closest to the calculation for $\hat{\tau}_m$ (using $K_t$) is assumed to be the correct solution. The following table defines the variables above.

| Variable | Notation | Details |
| --- | --- | --- |
| Bridge Voltage | $v_b$ | The DC bus voltage supplied to the motor drive power electronics |
| Bridge Current | $i_b$ | The current supplied to the motor drive power electronics by the bus voltage |
| Low-pass filter bandwidth | $f_B$ | The bandwidth in Hz of the low-pass filters employed in the force computation |
| Discrete Time Sample Period | $T_s$ | The interval between the samples in the discrete time control system. |
| Motor Torque | $T_m$ | The motor torque applied to the rotor by the stator windings |
| Motor Velocity | $\omega_m$ | The angular velocity of the motor |
| Motor Torque solutions | $\hat{\tau}_{m_1}, \hat{\tau}_{m_2}$ | The most positive and most negative torque solutions generated by the Motor Torque Solution Algorithm |
| q, d components | $()_q, ()_d$ | The component of voltage or current that aligns with the torque-producing, q, and non-torque-producing, d, vectors that denote the q, d coordinate system. |
| Motor Electrical Frequency | $\omega_e$ | The motor electrical frequency—a value equal to the product of the number of pole-pairs, $\frac{N_p}{2}$ and the motor angular velocity, $\omega_m$ |
| Motor Constant | $k_t$ | The motor constant that determines the scaling relationship between the motor torque and motor current ($\tau_m = k_t i_q$) and between the motor voltage and motor angular velocity ($v_q = k_t \omega_m$). |
| Motor voltage | $v_q, v_d$ | The vector that defines the motor voltage within the (q, d) coordinate system |
| Motor current | $i_q, i_d$ | The vector that defines the motor current within the (q, d) coordinate system |
| Motor Winding Voltage | $V_A, V_B, V_C$ | The voltages applied by the three-phase inverter to the motor windings |
| EMF Voltage | $v_{emf}$ | The back-emf (electro-motive force) is the open-circuit voltage generated when rotating the motor rotor, $v_{emf} = k_t \omega_m$ |
| Estimated or computed value | $\hat{()}$ | This refers to the computed value, including filtered signal representations. Lack of the "hat" designation refers to the actual value prior to sensing. |
| Motor resistance | $r_m$ | This is the winding resistance as measured from output to "center tap." |

The principles above can be relied on for estimating torque values based on the readily available current and voltages measurements, which is achievable using a low-cost Programmable System-on-Chip integrated circuit, such as the PSoC® line of circuits available from Cyprus Semiconductor Corp. Additional variables such as friction can be accounted for, as well as cogging effects that arise from harmonic disturbance torques by using a Kalman filter for example. As one of ordinary skill in the art would understand, the advantage of using a low-cost and simple integrated circuit for torque estimation provides a great advantage over prior devices that rely on sensors (pressure sensors, encoders, etc.) for providing device feedback, thus reducing the number of parts required and cost of the system as a whole. This advantage is greatly realized when torque sensing is used for triggering commands, as depicted in the Door Opening and Cartridge Loading, Syringe Drive, and Valve Drive sub-systems described below.

IV. Door Opening and Cartridge Loading Sub-System

In another aspect, the invention provides a door opening/closing and cartridge loading sub-system that is driven by a backdriveable mechanism so as to facilitate ease in manual loading and unloading an assay cartridge from the diagnostic assay system. In some embodiments, the door opening/closing mechanism and cartridge loading system are integrated so as to provide coordinated movement such that manual loading of the cartridge into an open bay of the system initiates closing of the bay door, typically upon detection of backdriving of the mechanism as the user manually pushes the cartridge into the system. It is appreciated that such mechanisms can be driven by a BLDC motor, as described herein, and utilize motor torque estimation, or utilize various conventional motors and approaches as would be known to one of skill in the art. Examples of such configurations are detailed below.

Figure 4A:
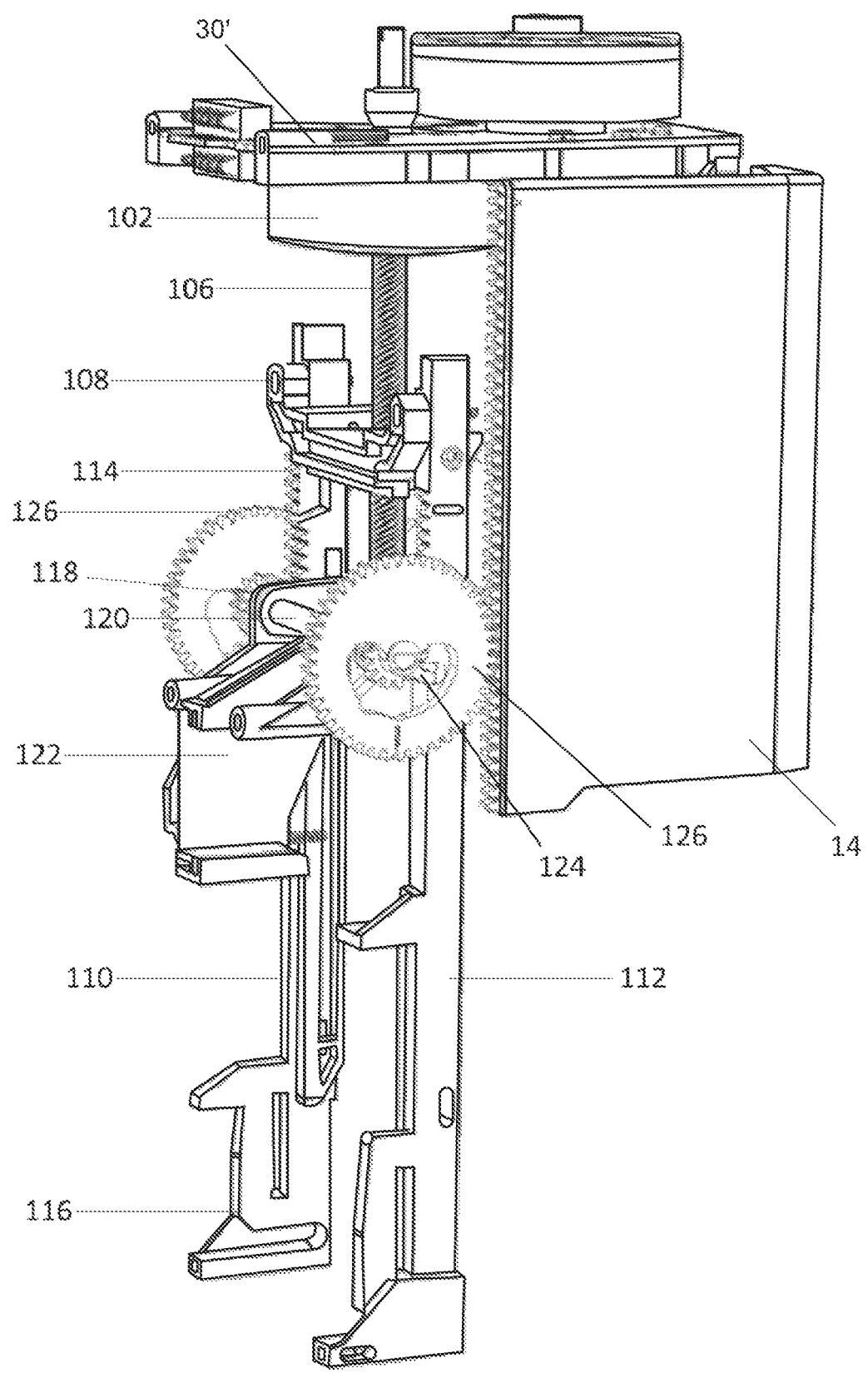
FIG. 4A is a perspective view of a door opening mechanism, according to some embodiments of the invention.
Figure 4B:
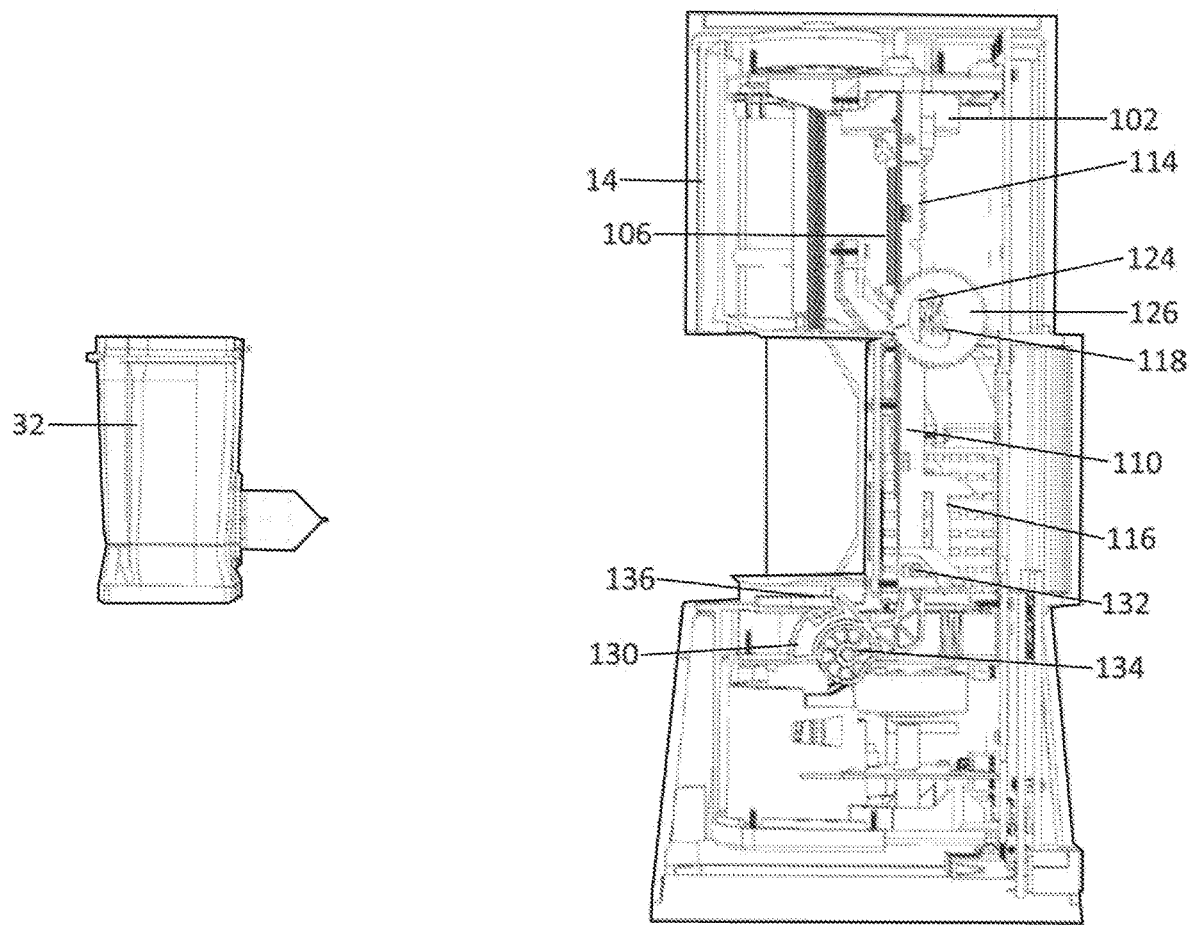
FIGS. 4B-4E are cross sectional views of a diagnostic assay system in use, according to some embodiments of the invention.

FIG. 4A shows a perspective view of a door opening and cartridge loading sub-system 100. The system includes a brushless DC (BLDC) motor 100, as described above, mounted to a PCB 30'. The BLDC motor 100 includes an output shaft (not shown) to which a lead screw 109 is attached. The lead screw 109 is back drivable aspect of a transmission that operates to open and close the door 14 as well as power a cartridge loading mechanism.

The lead screw 109 is threadingly engaged with a nut of a bridge 108, hence, when the lead screw 109 turns, the bridge 108 moves upward or downward (as the device is oriented in FIG. 4A) depending on the direction the lead screw 109 turns. A first rack portion 110 and a second rack portion 112 are affixed to the bridge 108. Both rack portions are elongated to include a rack 114 and a cam pathway 116, that forms an "L" like path.

A pair of pinion gears 118 are meshed with the racks 114. Up and down movement of the racks 114 is caused by movement of the bridge 108 and the lead screw 109, which causes the pinions 118 to rotate accordingly. The pinion gears 118 are connected to each other by a shared shaft 120 that is supported by a sub-frame 122, which is affixed to a greater portion of the system 10, such as rear chassis portion 26. Each pinion gear 118 includes a finger 124 for stopping rotation of the pinion gear 118 at certain interfaces.

Each pinion gear 118 is integrated with a larger door gear 126. Accordingly, the pinion gears 118 and door gears 126 spin at the same RPM. The door gears 126 interfaces with door racks 128 of the door 14. Hence, when the door gears 126 turn, the door racks 128 and door 14 move up or down according to the direction the door gears 126 are spinning.

FIGS. 4B-4E graphically depict a method of loading an assay cartridge. At FIG. 4B, a command is sent to the BLDC motor 102 to open the door 14 to place the system into position to accept insertion of the cartridge 32. When the command is received, the system 100 operates the BLDC motor 102 to turn the lead screw 109. This action causes the bridge 108 and affixed rack portions 110/112 to move upwardly, and hence initiate turning of the pinion gears 118 and door gears 126. This movement will cause the door 14 to travel upward as the door gears 126 spin against the door racks 128.

After the door 14 is completely open, the pinion gears 118 disengage from the racks 114 of the first and second rack portions 110/112, which continue to move upwards. Upward movement of the first and second rack portions 110/112 also causes cartridge loading arms 130 to be actuated by the pins 132 that are constrained to move along the cam pathways 116 of the first and second rack portions 110/112. The cartridge loading arms 130 are forced by this movement to spin about pivots 134, which places first arm portions 136 into an upward position.

The first and second rack portions 110/112 will move upwardly, until a force based event occurs that back drives the lead screw 109. Such an event can be, for example, the bridge 108 encountering a stop or the first and second rack portions 110/112 pulling against the cartridge loading arms 130. The back driving event can be detected at a bridge circuit of the BLDC motor as a change in current. Based on the back driving event, the BLDC motor is commanded to stop turning and rest in the position shown. Advantageously, this step is performed without the aid of any position sensors.

Figure 4C:
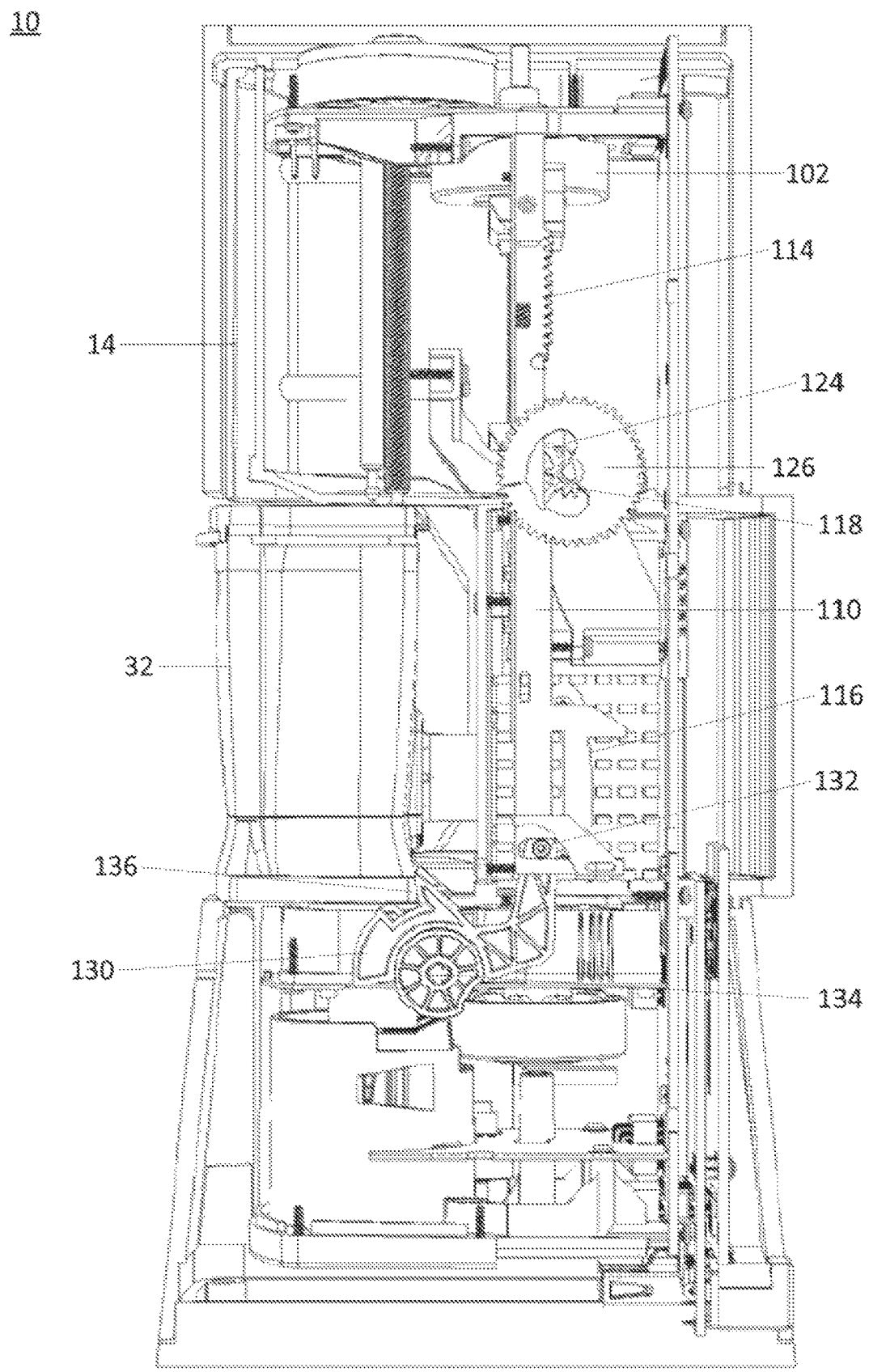

At FIG. 4C, the assay cartridge 32 is inserted into the system 10 until a portion of the assay cartridge 32 is brought into contact with the first arm portions 136. Slight movement against the first arm portions 136 results in another back driving event at the lead screw 109 that is detectable at the bridge circuit of the BLDC motor as a change in current. This event serves as a command for the BLDC motor to reverse direction from the previous door-opening step in order to capture the cartridge and close the door.

Figure 4D:
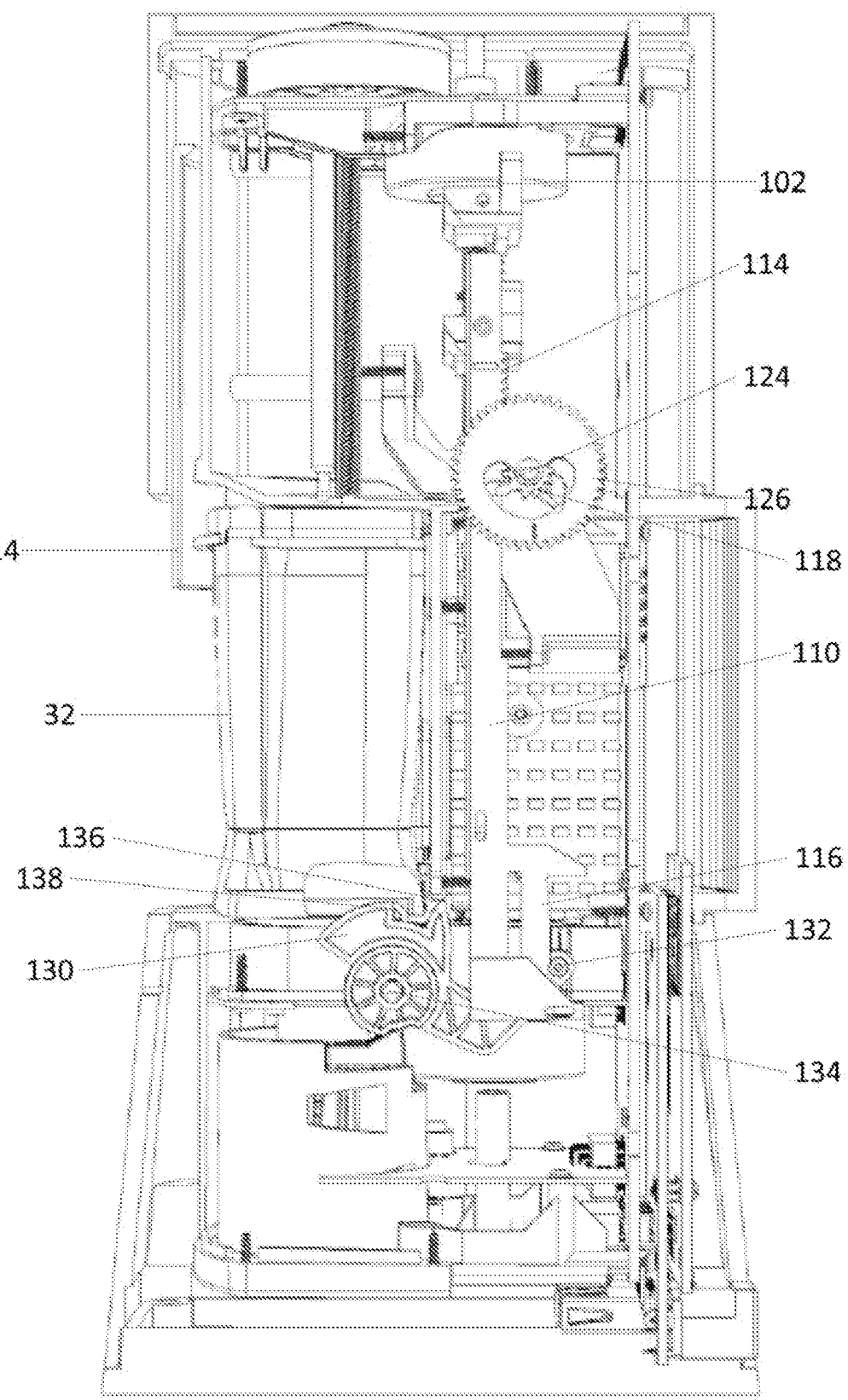

As shown at FIG. 4D, upward movement of the first and second rack portions 110/112 causes the pins 132 to be guided about the length of the cam pathways, which in turn causes the cartridge loading arms 130 to rotate in a clockwise direction. This causes second arm portions 138 of the cartridge loading arms 130 to push the cartridge inward into a home position. In addition, the first and second rack portions 110/112 are raised until the fingers 124 of the pinion gears 118 are turned by notches 140 of the first and second rack portions 110/112, which initiates movement of the pinion gears 118 against the rack 114, as well as the door gears 120 against the door rack 128. In this manner, the door 14 is made to travel downward towards a closed position.

Figure 4E:
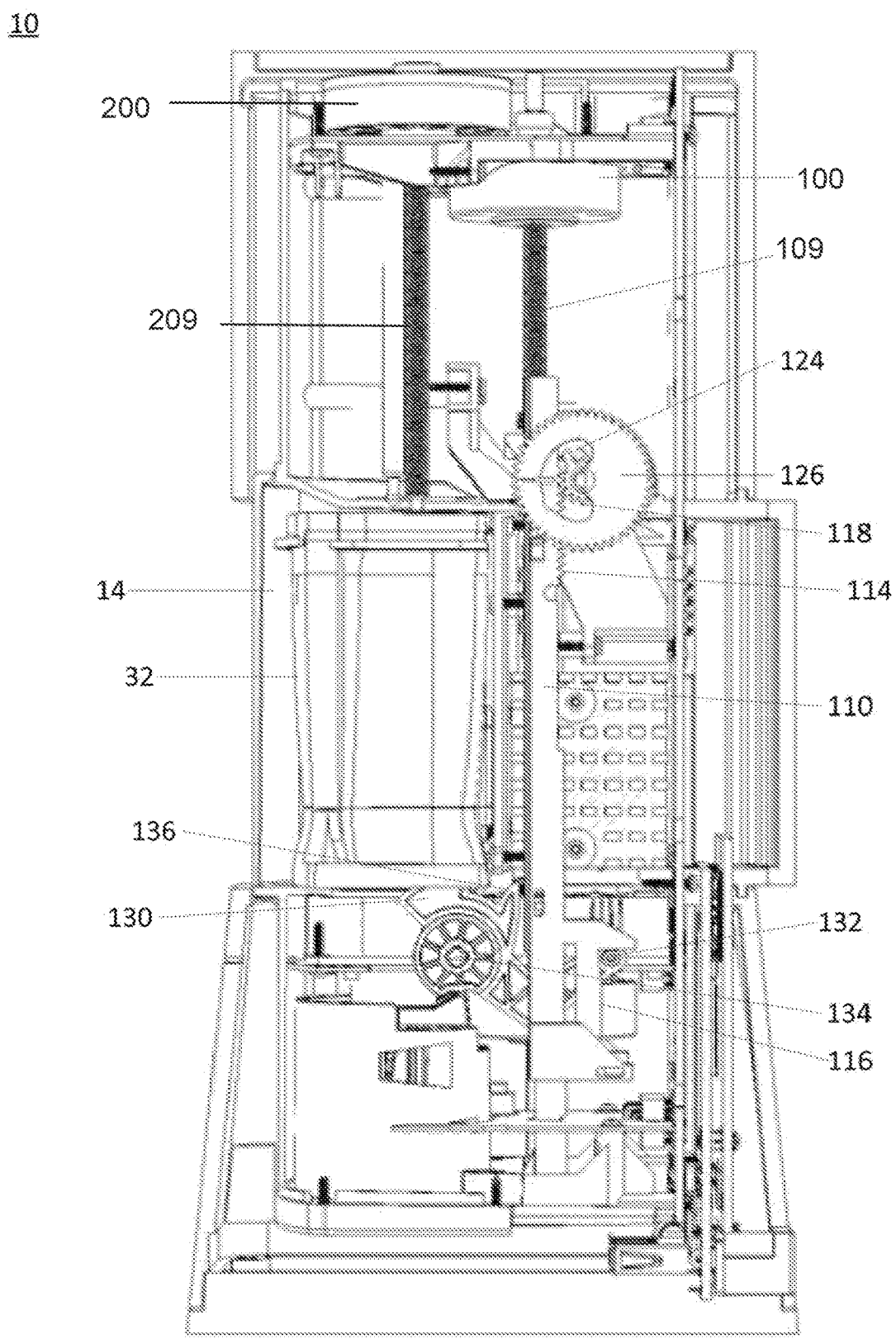

As shown at FIG. 4E, the door 14 is made to travel downward by continued movement of the lead screw 109 to completely close the door. The BLDC motor is powered to do so until a force based event occurs that back drives against the lead screw 109. Such an event can be, for example, the bridge 108 encountering a stop or the first and second rack portions 110/112 pushing against the cartridge loading arms 130. The back driving event can be detected at the bridge circuit of the BLDC motor as a change in current. Based on detection of the back driving event, the BLDC motor is commanded to stop turning and rest in the position shown. Advantageously, this step is performed without the aid of any position sensors.

V. Syringe Drive Sub-system

Figure 5A:
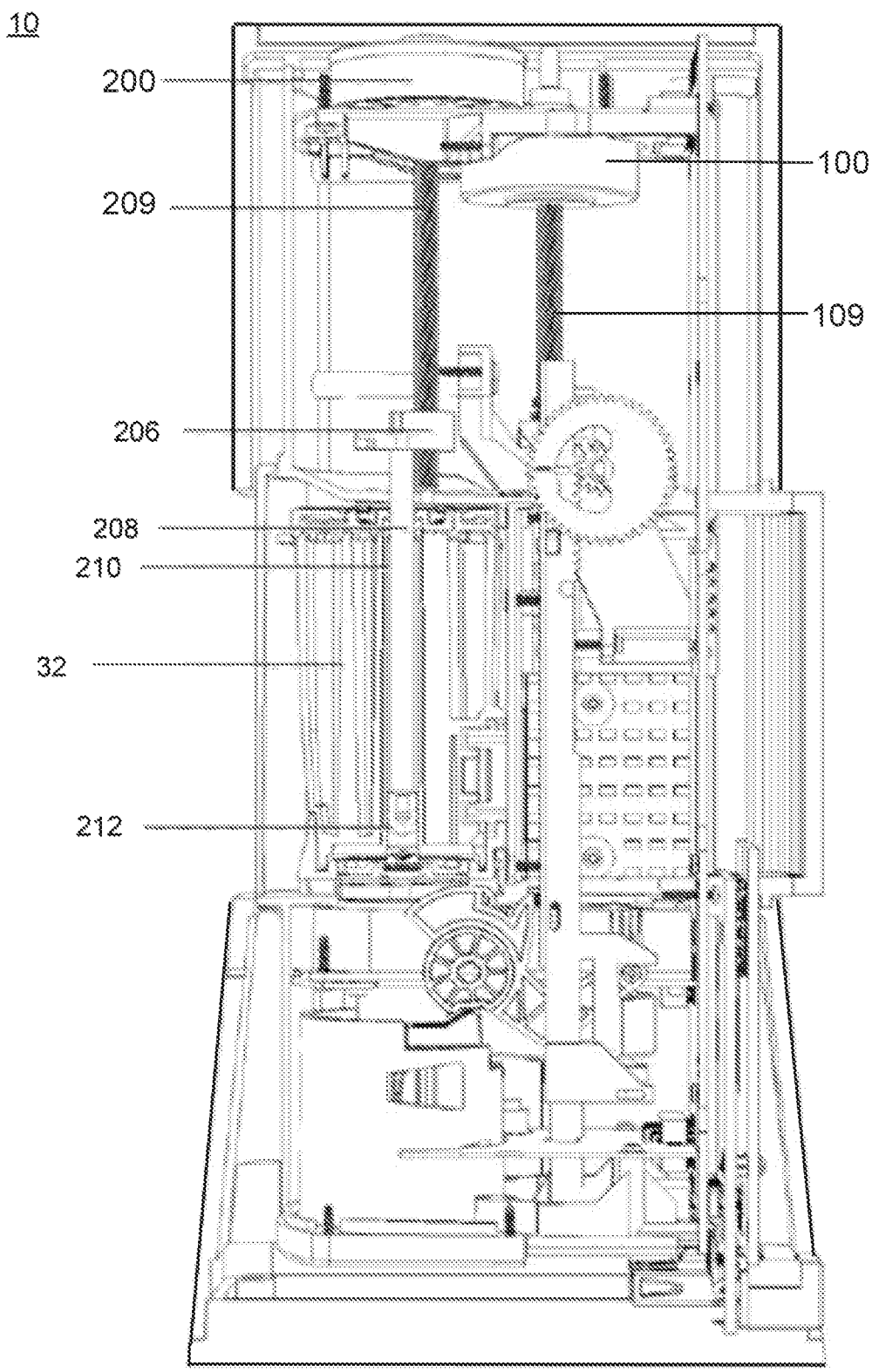
FIG. 5A is a cross sectional view of a diagnostic assay system in use, according to some embodiments of the invention.

As described above, embodiments of the invention can include aspects of the syringe drive mechanism 16. As shown at FIG. 5A, the syringe drive mechanism 16 includes a BLDC motor 200 as described above. The BLDC motor 200 includes an output shaft that is connected to a back drivable lead screw 209.

A laterally extending arm 206 includes a nut that is threaded to the lead screw 209. The laterally extending arm 206 also is affixed to a plunger rod 208. The laterally extending arm 206 and plunger rod 208 can be driven downward and upward by commanding the BLDC motor 200 to turn the lead screw 209 in an appropriate direction.

After the assay cartridge 32 is secured and the door 14 is closed, the syringe drive mechanism 16 can be utilized to interface with the assay cartridge 32. The assay cartridge includes a syringe passage 210 holding a plunger tip 212. Downward movement of the plunger rod 208 into the syringe passage 210, which causes the tip of the plunger rod 208 to engage the plunger tip 212. In this manner, the combined plunger tip 212 and plunger rod 208, together with the syringe passage, functions as a syringe to pressurize/depressurize the assay cartridge 32. Programmed pumping of the assay cartridge 32 causes fluid to flow into and out from various chambers of the assay cartridge 32 to affect an assay.

After engagement with the plunger tip 212, the plunger rod 208 can be actuated by the BLDC motor 200 to any desired position within the syringe passage 210, including enactment of various syringe pumping algorithms. Currents of the BLDC motor 200 can be continually monitored to deliver a consistent pressure to the plunger rod, thus, alleviating the need for an in-line pressure sensor to monitor cartridge pressure.

Accordingly, because the lead screw 209 can be back driven, a pressure decrease within the assay cartridge 32 can cause a stationary plunger rod 208 to be pulled downward. The pressure decrease can be detected by monitoring the measured current of the BLDC motor 200, detecting a relative change, and then changing the output of the BLDC motor 200 accordingly. Similarly, a pressure decrease within the assay cartridge 32 can cause a stationary plunger rod 210 to be pushed upward. The pressure increase can be detected by monitoring the measured current of the BLDC motor 200, detecting a relative change, and then changing the output of the BLDC motor 200 accordingly. Advantageously, this can be performed without the aid of any pressure sensors.

In another example, the current associated with a moving plunger rod 208 can be monitored for changes that indicate increases or decreases in pressure rate. Hence, after detecting a relative change, the output of the BLDC motor 200 can be changed to increase or decrease the pressure rate being applied by the moving plunger rod 208. Advantageously, this can be performed without the aid of any pressure sensors.

Figure 5B:
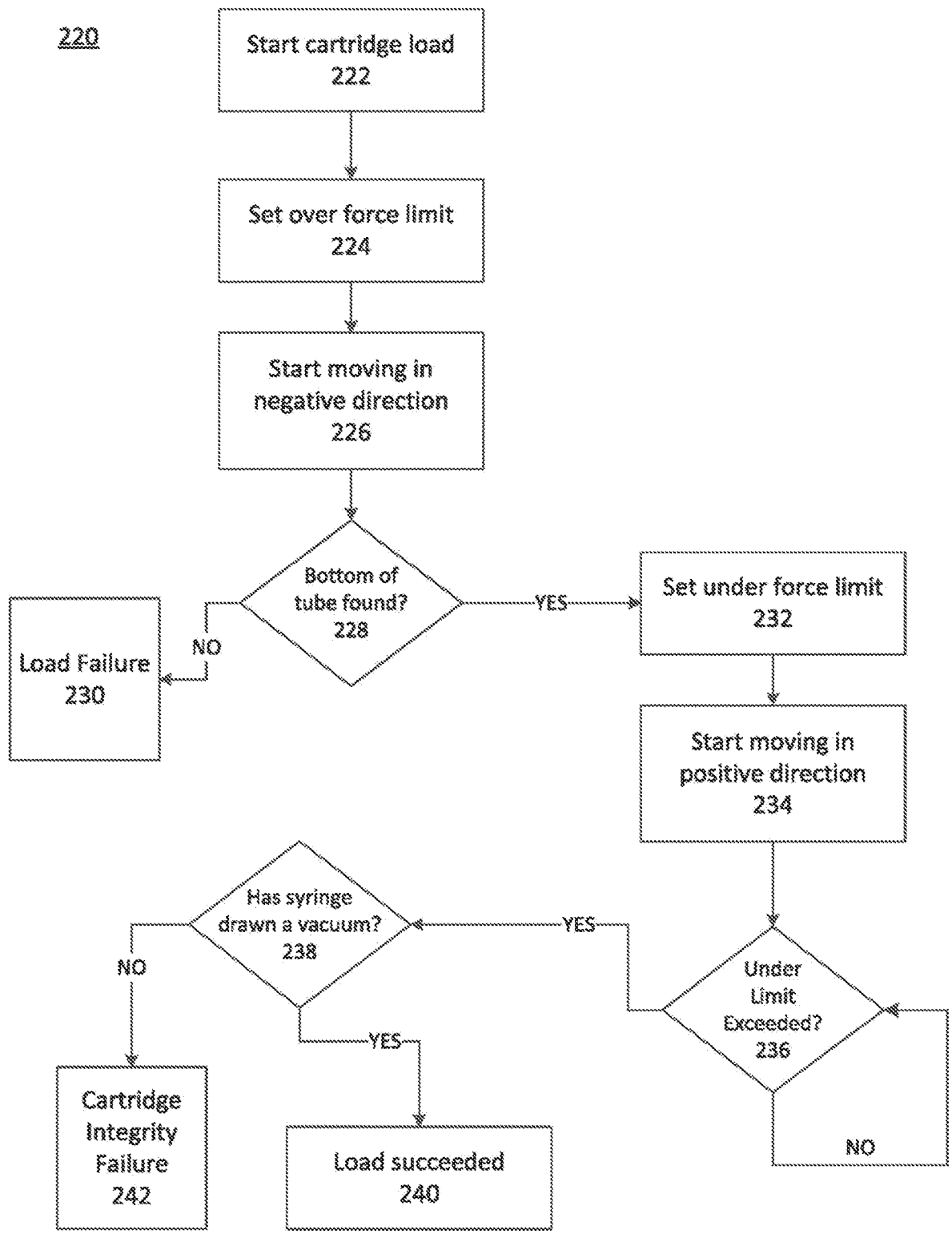
FIGS. 5B and 5C are flow diagrams of a method for operating aspects of a diagnostic assay system, according to some embodiments of the invention.

An example of a method 220, using the aforementioned principles of BLDC current monitoring, for determining proper loading of an assay cartridge and testing integrity of that cartridge is depicted at FIG. 5B. It is assumed that the assay cartridge 32 has been already physically loaded as shown at FIG. 5A.

At operation 222, a command is sent to begin the loading procedure. As a result, an over force limit is set at operation 224. The over force limit is the maximum force the BLDC motor 200 may exert onto the plunger rod 208 for the purposes of this operation, which is associated with the plunger rod 208 compressing the plunger tip 212 against the bottom of the syringe passage 210. At operation 226, the BLDC motor 200 is operated to move the plunger rod 208 into the syringe passage 210, which causes the tip of the plunger rod 208 to engage the plunger tip 212. At operation 228 torque of the BLDC motor 200 is continually monitored, using the torque estimation circuit of FIG. 2E and the methodology of FIGS. 3A-3C, to determine if the plunger rod 208 has travelled to the bottom of the syringe passage 210. If the over force limit is not exceeded then it is determined that the loading procedure has failed at operation 230. Occasionally, the plunger tip 212 may be missing due to a manufacturing error or physically deficient. In either case, the plunger rod 208 will meet the end of its possible travel with the syringe passage 210 without properly bottoming against a plunger tip 212, and hence, the over force limit will not be exceeded.

If the over force limit is exceeded then it is determined that the plunger rod 208 has pushed the plunger tip 212 to the bottom of the syringe passage 210, and the method 220 moves to operation 232, where an under force limit is set. The under force limit is the maximum force the BLDC motor 200 may exert onto the plunger rod 210 for the purposes of this operation, which is related to decompressing the plunger tip 212. At operation 234 the BLDC motor 200 is operated to move the plunger rod 210 upward within the syringe passage 210. At operation 236 torque of the BLDC motor 200 is continually monitored to determine if the under limit has been exceeded. As a result of operation 228, the plunger tip 212 will be highly compressed. The under limit is the amount of force required to decompress the plunger tip and thereby zero out the position of the plunger tip 212 for later operation. Once the under limit is exceeded, the BLDC motor 200 will cease operation and the method will move to operation 238, where it is determined if the syringe has drawn a vacuum. At this operation, valving of the assay cartridge 32 is operated to seal off the syringe passage 210 to atmosphere, which was not the case in the preceding steps. After this is complete, the BLDC motor 200 is operated to pull the plunger rod 208 upwards against the vacuum within the syringe passage 210. If the plunger rod 208 does not move freely and force is detected, then at operation 240 it is determined that vacuum has been established and thus integrity of the assay cartridge 32 is not comprised. If the plunger rod 208 moves freely without detection of force, then at operation 242 it is determined that no vacuum has been established and thus integrity of the assay cartridge 32 is compromised.

Figure 5C:
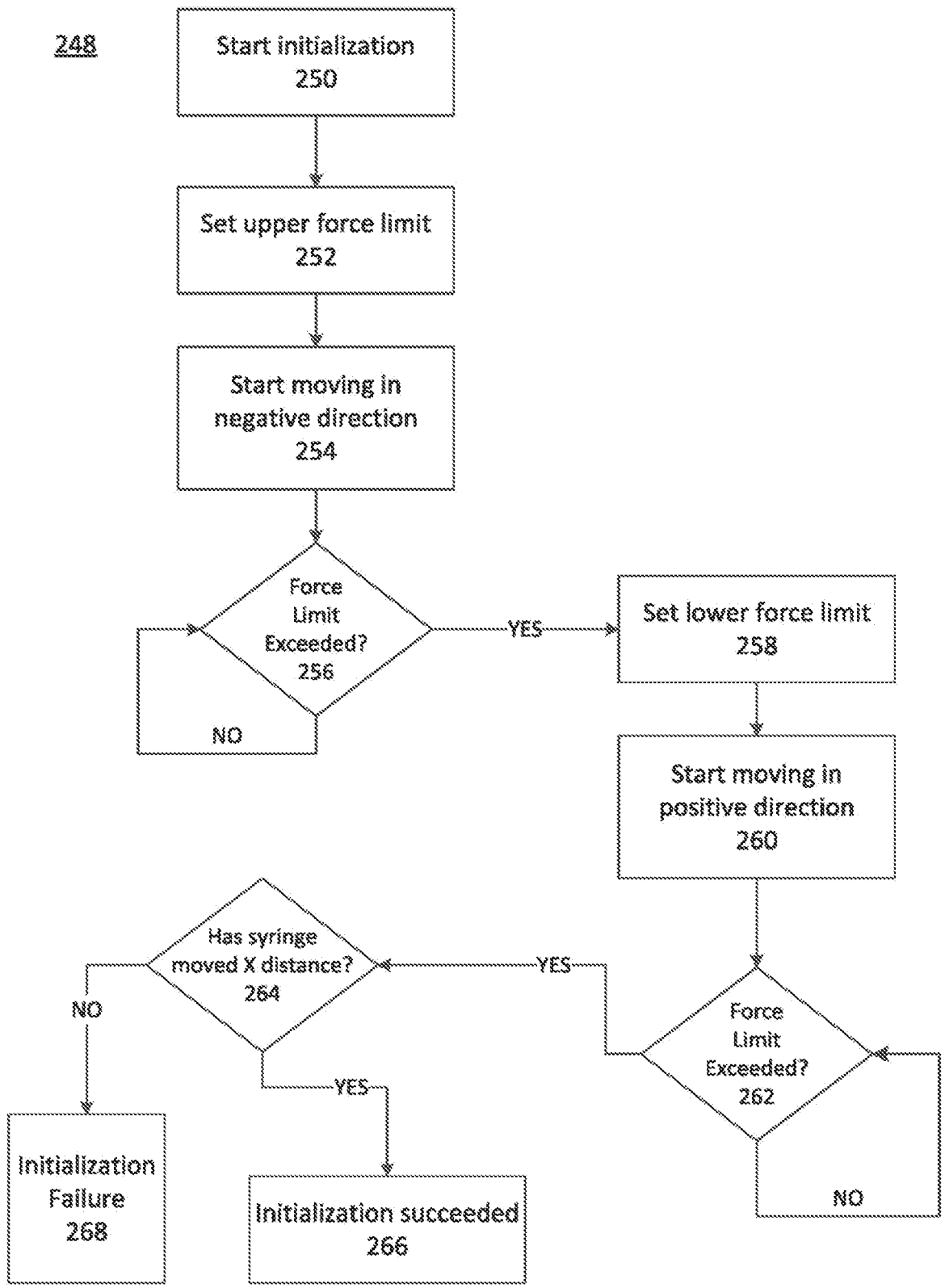

Another example of a method 248, using the aforementioned principles of BLDC current monitoring, for determining initializing the syringe of the assay cartridge (i.e., plunger rod 208, syringe passage 210, and plunger tip 212) is depicted at FIG. 5C. It is assumed that the assay cartridge 32 has been already physically loaded as shown at FIG. 5A, and the cartridge has been loaded properly as shown at FIG. 5B.

At operation 250, a command is sent to begin the loading procedure. As a result, an upper force limit is set at operation 252. The over force limit is the maximum force the BLDC motor 200 may exert onto the plunger rod 208 for the purposes of this operation, which is associated with placing the plunger tip 212 at a proper upward position (relative to the orientation of the device as shown in FIG. 5A) at the top of the syringe passage 210.

At operation 254, the BLDC motor 200 is operated to move the plunger rod 208 upwardly within the syringe passage 210, which causes the plunger tip 212 to top out at a position within the syringe passage 210. At operation 256 torque of the BLDC motor 200 is continually monitored, using the torque estimation circuit of FIG. 2E and the methodology of FIGS. 3A-3C.

Once the over force limit is exceeded then it is determined that the plunger tip 212 is topped out, and the method 248 moves to operation 258, where a lower force limit is set. The lower force limit is the maximum force the BLDC motor 200 may exert onto the plunger rod 210 for the purposes of this operation, which is related to placing the plunger tip 212 against the bottom of the syringe passage 210, but without excessive compression of the plunger tip 212. At operation 260 the BLDC motor 200 is operated to move the plunger rod 210 downwardly within the syringe passage 210. At operation 262, torque of the BLDC motor 200 is continually monitored to determine if the lower force limit set at operation 258 has been exceeded. Once the lower limit is exceeded, the BLDC motor 200 will cease operation, and it is assumed the plunger tip 212 has been placed at the bottom of the syringe passage 210. After this, the method 248 will move to operation 238, where it is determined if the syringe has moved a predetermined amount of distance (e.g. 60 mm). This is performed by using the Hall-effect sensors of the BLDC motor 200 to count revolutions of lead screw 209 and relating that count to an amount of linear travel of the syringe rod 208. In some cases the upper and lower force limits will be triggered by obstructions or excessive friction within the syringe passage 210. Hence, the travel check step is performed to make sure the syringe rod 208 has moved freely without obstruction. If the syringe rod 208 has moved at least the predetermined amount of travel, then it is determined that initialization is successful at operation 266. However, if the syringe rod 208 has not moved at least the predetermined amount of travel, then it is determined that initialization is not successful at operation 268.

VI. Valve Drive Sub-system

Figure 6A:
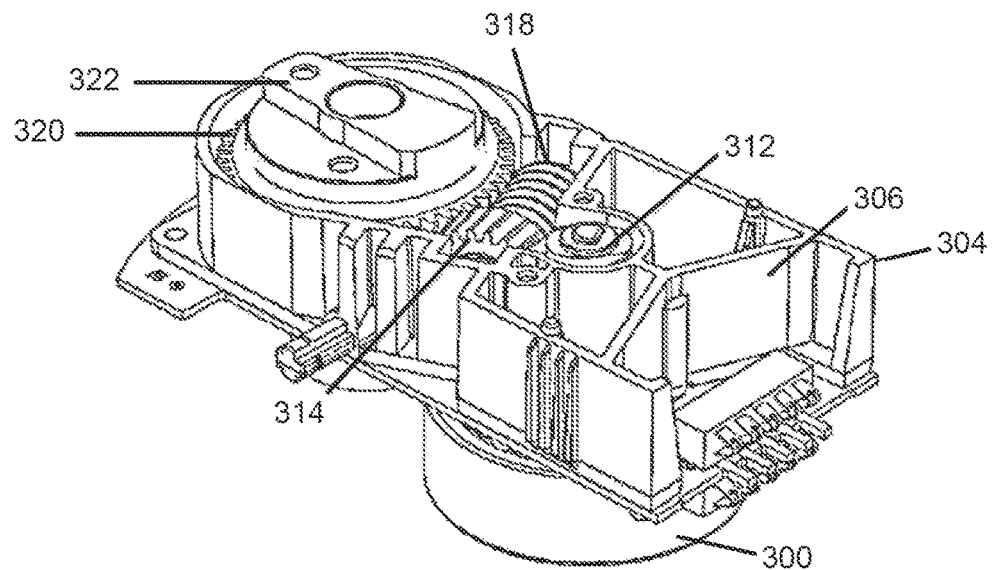
FIGS. 6A and 6B are perspective views of a valve drive mechanism, according to some embodiments of the invention.
Figure 6B:
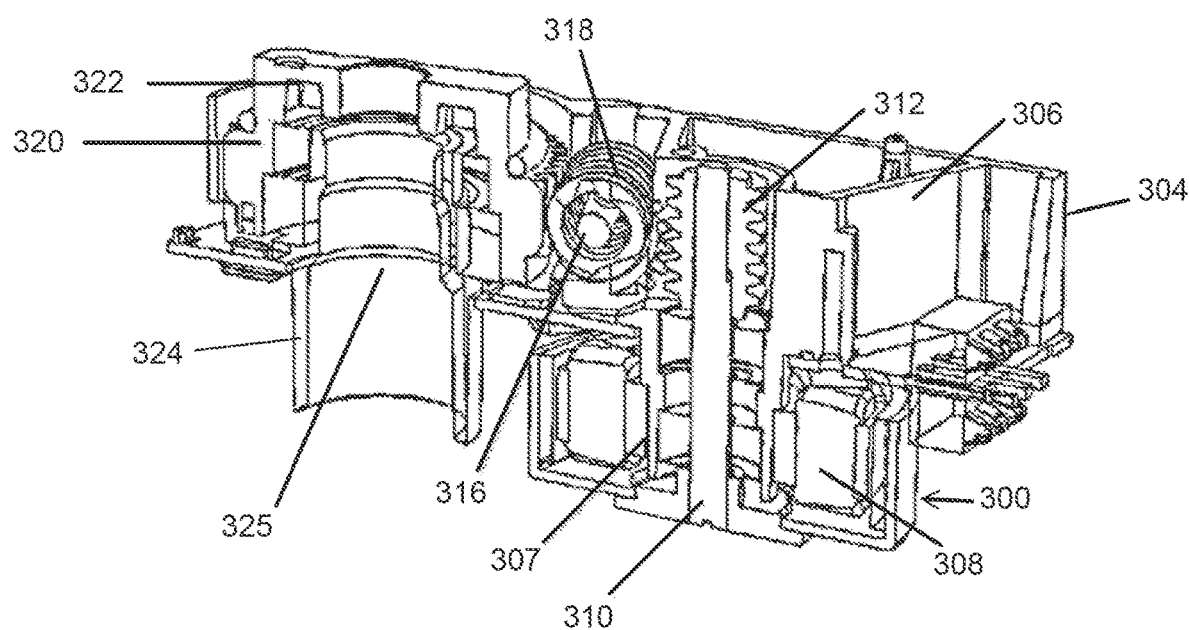

As described above, embodiments of the invention can include aspects of the valve drive mechanism 20. As shown at FIGS. 6A and 6B, the valve drive mechanism 20 includes a BLDC motor 300 as described above.

The BLDC motor 300 is mounted to a chassis 304 having a plurality of reinforcing ribs 306 that contribute to the rigidity of the chassis 304. The chassis 304 includes an elongated first portion 307 that serves as a mount for a stator 308 of the BLDC motor 300. An elongated shaft 310 extends from the BLDC motor 300 and holds a first worm 312. The first worm 312 cooperates with and turns a first worm gear 314, which turns on a shaft 316 shared with a second worm 318.

The second worm 318 cooperates with and turns a second worm gear 320. The second worm gear 320 is integrated with a turntable like valve drive 322, which is configured to cooperate with a turning valve mechanism of the assay cartridge 32. The valve drive 322 is mounted to an elongated second portion 324 of the chassis 304. The elongated second portion 324 includes a passage 325 for cooperation with the sonication horn mechanism 22.

In use, the BLDC motor 300 is powered to turn and thereby turns valve drive 322 via the worm drives described above. The valve drive 322 is substantially geared down, which allows for great precision when positioning the valve drive 322. The syringe drive mechanism 16 does not include any position sensors, because angular position of the stator 308 can be solely derived from the sinusoidal wave output of the hall-effect sensors, and through that position of the valve drive by knowledge of the final drive gear ratio.

The worm drives are not back drivable as in the aforementioned syringe drive and door drive mechanisms. However, the same type of hall-effect position derivation and force base triggering can be used for the valve drive mechanism. Here, force base triggering can be indicative of a cartridge integrity malfunction. For example, if turning the valve drive unexpectedly requires substantially less or more power, then such an event can be indicative of a jam or failure of an assay cartridge. While each of the syringe drive, door drive mechanisms and valve drive mechanisms are described as utilizing the improved BLDC motor described herein, it is appreciated that any or all of the drives and mechanisms could also utilize a conventional type BLDC motor, a servo motor or other suitable motor, as would be understood by one of skill in the art, however some features may require additional sensors or circuitry.

In addition, the BLDC motor is configured to home and center position of the valve drive output by performing a centering protocol based on the sinusoidal signal generated by the hall-effect sensors. This can compensate for gear backlash and gear wear over time. This is illustrated by the Hall voltage signal to valve drive position graph shown at FIG. 6C. As shown, a given position of the valve drive 322 can vary according to gear backlash and wear.

VII. Horn Subassembly

In some embodiments, an ultrasonic horn subassembly is provided for use in an diagnostic assay system as described herein. In some embodiments, the ultrasonic horn assembly includes an ultrasonic horn, a horn housing, a spring, a chassis and control circuitry configured for operation of the horn. The horn housing is adapted for supporting and securing the ultrasonic horn and includes a section for retaining a spring coil to facilitate movement between a disengaged and engaged horn position and a wedge for interfacing with a cam mechanism of the system to actuate movement of the horn between the disengaged (lowered) and engaged (raised) positions. Although a coil spring is described herein, it is appreciated that various other types of springs or biasing mechanisms can be used. In the disengaged position, the tip of the ultrasonic horn is flush or below a base surface upon which the assay cartridge sits to facilitate loading and removal of the assay cartridge from the system. In the engaged position, the tip of the ultrasonic horn extends above the base surface so as to engage a domed portion of a sonication chamber of the assay cartridge to facilitate sonication of biological material in a fluid sample contained within the sonication chamber during sample analysis preparation and/or processing. In some embodiments, the movement of the horn is effected by an actuator mechanism common to one or more other movable components of the system, such as a door of the system. The horn assembly also includes circuitry, such as a printed circuit board, with interfaces adapted for electrical connection to corresponding circuitry within the system to facilitate operation of the ultrasonic horn by the system.

Figure 9A:
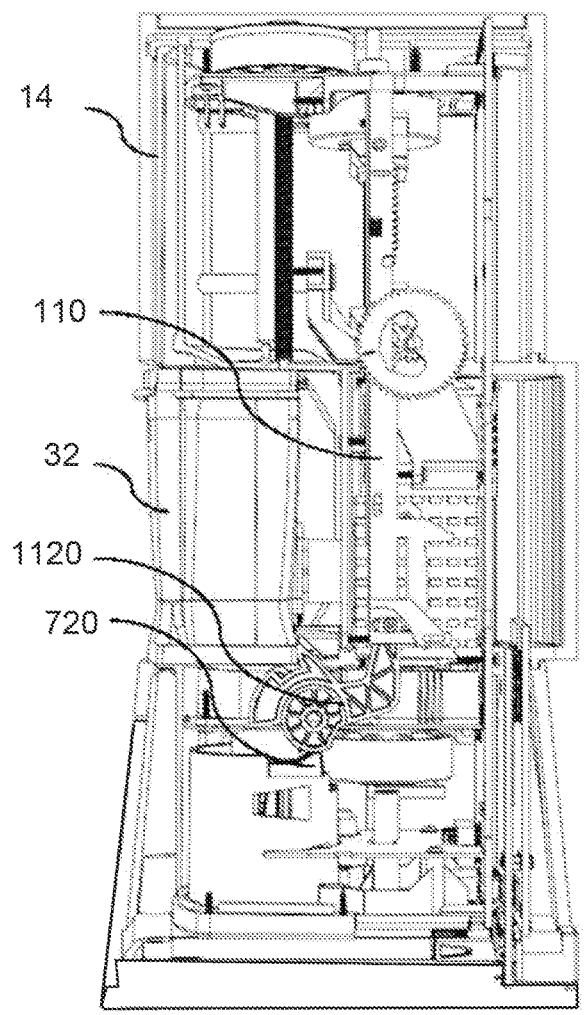
FIGS. 9A-B illustrates cross-sectional views of a diagnostic assay system during and after loading of an assay cartridge in accordance with some embodiments of the invention.
Figure 9B:
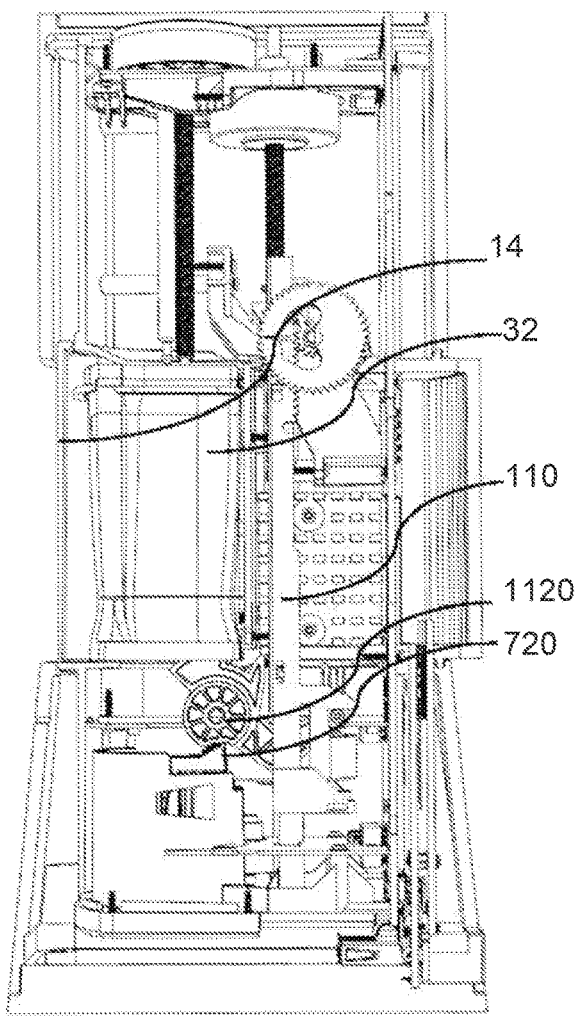

In some embodiments, the diagnostic assay system is placed upright during performance of an assay (as shown in FIGS. 9A-B) such that the horn moves between the disengaged position (lowered below the cartridge) and the engaged position (raised toward the cartridge) so as to engage and contact the sonication chamber of the cartridge. It is appreciated that in some embodiments, the design could be different such that in the disengaged positions and engaged positions the horn could be in various other orientations and/or locations relative the cartridge depending on the design of the cartridge and the diagnostic assay system.

VII. A. Horn Subassembly Design and Assembly

Figure 7A:
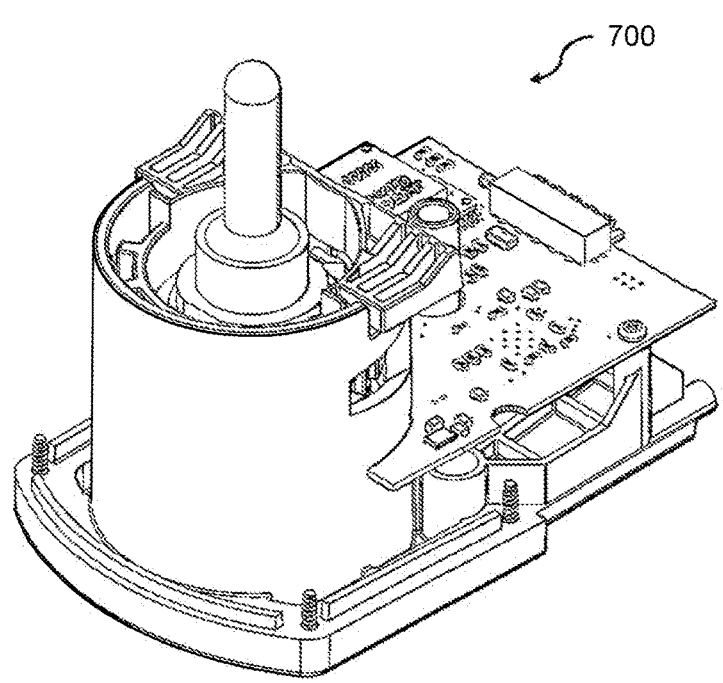
FIGS. 7A-B illustrates an ultrasonic horn assembly for use in diagnostic assay system in accordance with some embodiments of the invention.
Figure 7B:
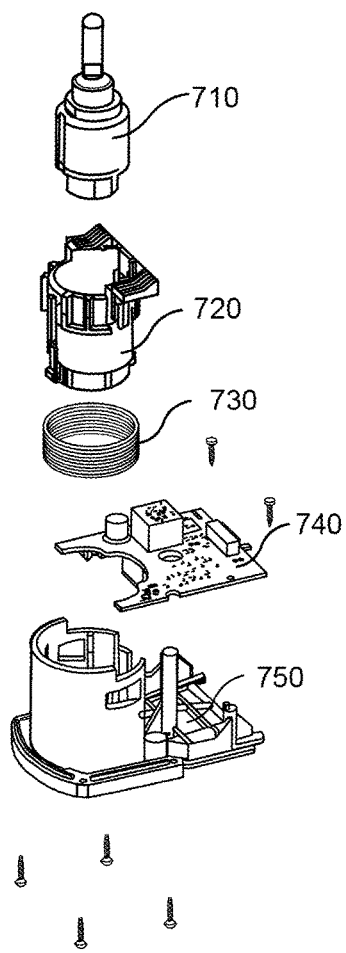

FIG. 7A illustrates an ultrasonic horn subassembly 700 configured for use in a diagnostic assay system in accordance with some embodiments of the invention. FIG. 7B depicts an exploded view of the horn assembly of FIG. 7A. In this embodiment, the horn subassembly includes an ultrasonic horn 710, horn housing 720, spring coil 730, control circuitry 740, and chassis 750. The horn subassembly can be tested as a stand-alone sub-assembly before insertion into the system and may also be removed or replaced as needed.

Figure 8A:
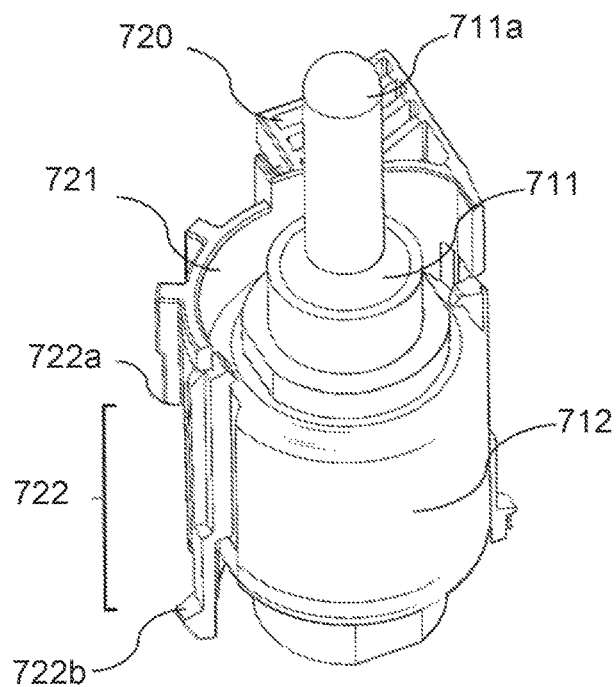
FIGS. 8A-D illustrates component views of ultrasonic horn assembly in accordance with some embodiments of the invention.
Figure 8B:
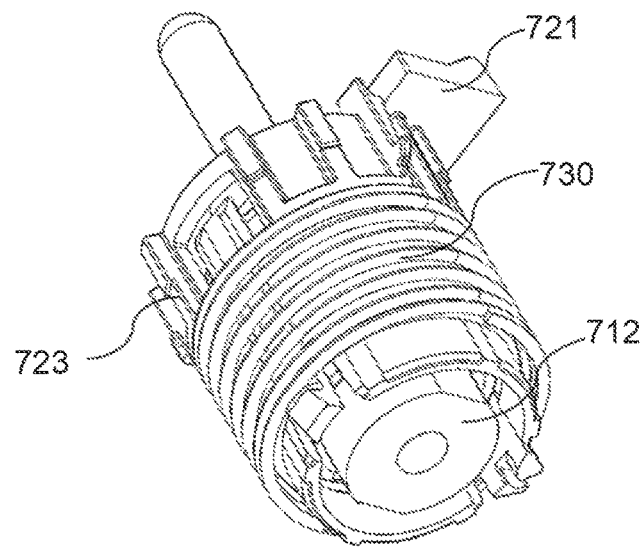

FIGS. 8A-E illustrate the components of the horn assembly during various stages of assembly. As shown in FIG. 8A, ultrasonic horn 710 snaps into the horn housing 720 (shown cut-away to show the horn residing within). The housing can be designed such that snapping the horn into the housing locates or clocks the horn within a pre-determined orientation and position relative the housing. For example, the ultrasonic horn can be of a design that includes features that are not perfectly axi-symmetric about a longitudinal axis of the horn such that corresponding features or surfaces on an interior portion of the housing engage to secure the horn into position within the housing and inhibit rotation of the horn therein. The non-axi-symmetric feature may include, but is not limited to, a flat portion on one or both sides of the horn or a protrusion or tab extending outwardly from the horn or a contact through which the horn is electrically connected.

In some embodiments, the horn 720 is incorporated into the subassembly and controlled with the control circuitry to provide an output suitable for lysing biological materials as needed for a particular assay.

As can be seen in FIG. 8A, the outside surface of the horn housing 720 includes a spring retention portion 722 for retaining a spring coil 730 to effect movement of housing 720 between the disengaged and the engaged positions. The retaining portion includes an upper retaining surface 722a and a lower retaining surface 722b that engage the spring when in a non-compressed state. The housing 720 may also include one or more lead retention details 723 to secure and/or guide the leads electrically connected to the horn 710 during movement of the horn between the disengaged/engaged positions. The horn housing 720 includes a wedge portion 721 for interfacing with a cam of the system.

Figure 8C:
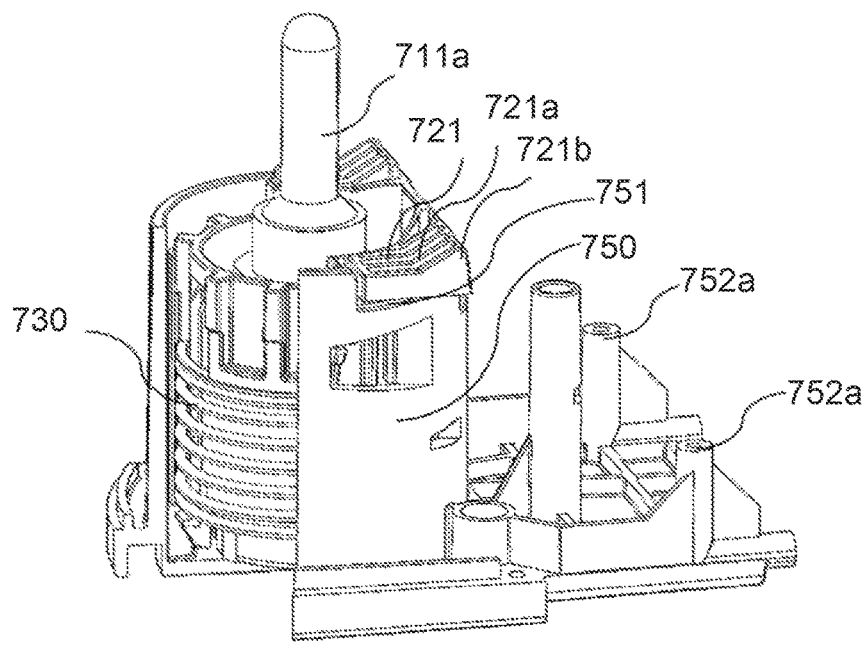
Figure 8D:
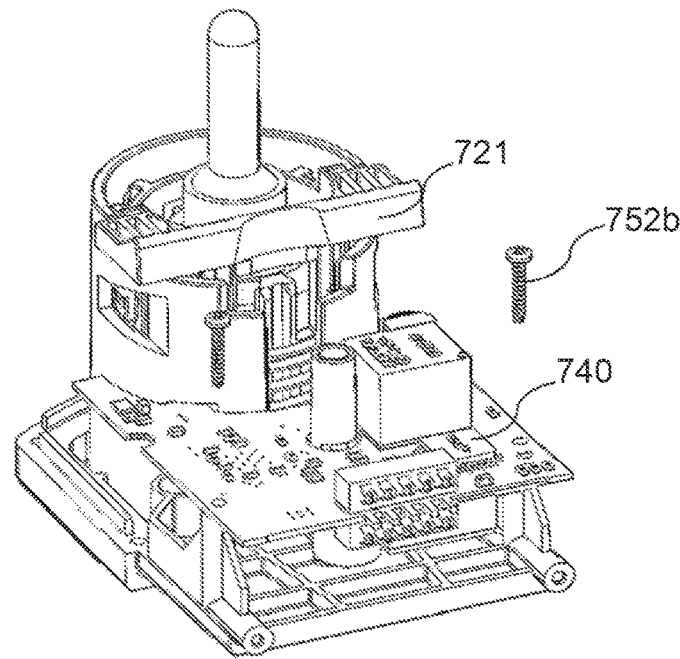

As shown in FIG. 8C, the partially assembled horn assembly can be snapped into a horn chassis 750. The chassis includes a localization feature 751 that engages a corresponding feature of the housing 720 so as to secure the position and orientation of the housing when snapped in place. The chassis also includes one or more features for securing the entire horn assembly 700 within the diagnostic assay system, for example, the chassis may include a base portion with one or more holes through which the chassis can be mounted to the module. In some embodiments, the chassis is formed of a polymer material by injection molding, although it is appreciated that it may be formed of various other materials (e.g. polymer, ceramic, metal) by various other manufacturing processes (e.g. pressing, machining, etc.). After placement of the horn assembly into the chassis, a circuitry component 740 is attached to the chassis. The chassis may include one or more mounting features 752a through which the circuitry component (e.g. PCB) can be secured by one or more fasteners or screws 752b. The circuitry component can be electrically connected to the horn before or after its attachment to the chassis. The completed horn assembly 700 can then be tested and supplied to a user separately or within a diagnostic assay system.

VII. B. Sonication Horn Positioning Interface

Figure 10A:
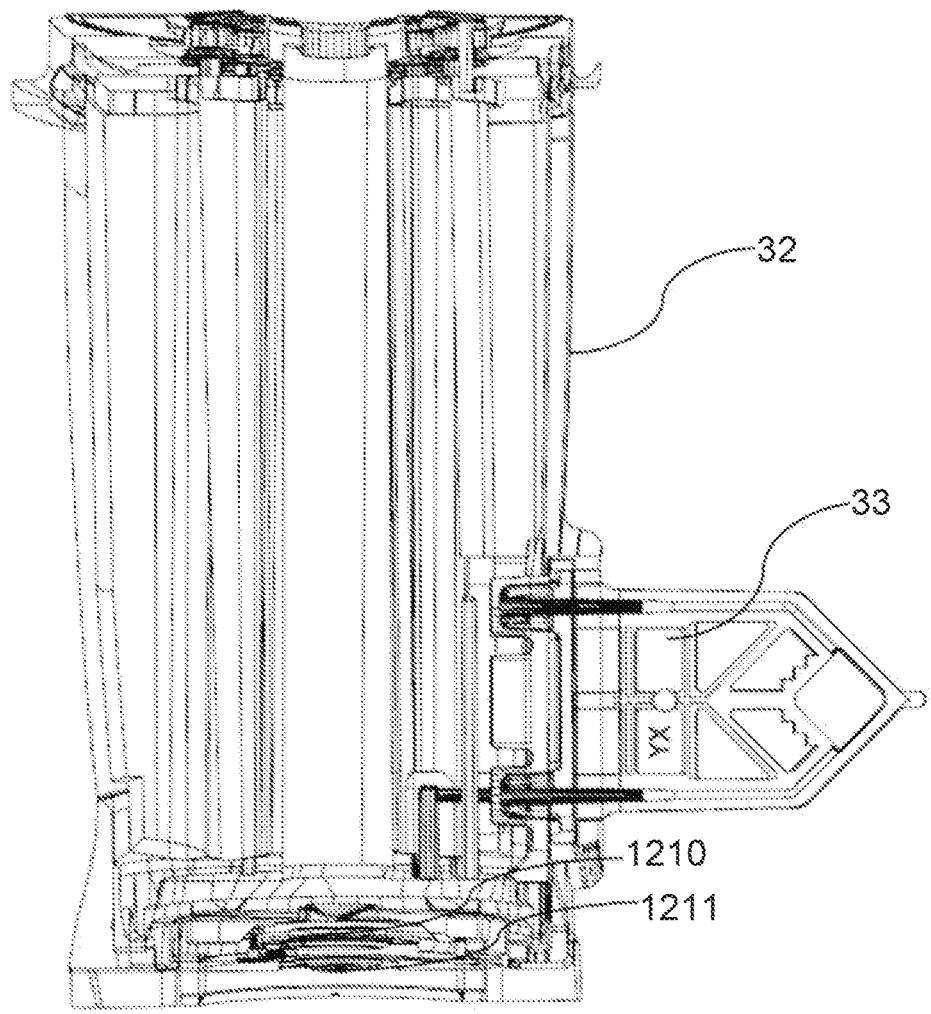
FIG. 10A illustrates cross-sectional view of an assay cartridge and FIG. 10B illustrates a cut-away view of an assay cartridge loaded in a diagnostic assay system with an ultrasonic horn assembly in accordance with some embodiments of the invention.

In some aspects, the ultrasonic horn is mounted on a movable mechanism by which the ultrasonic horn is positioned relative to a sonication chamber of an assay cartridge disposed within a diagnostic assay system. In some embodiments, the assay cartridge includes a sonication chamber positioned on the bottom of the cartridge (as oriented in FIG. 10A) with a downward facing dome (outer surface of the dome being convex shaped with respect to the assay cartridge), as shown in the example of FIG. 10A, that corresponds to a rounded tip 711A of the domed output portion 711 of the ultrasonic horn. Although the tip is rounded in this embodiment, it is appreciated that the tip of the dome portion may be shaped in a variety of shapes, including but not limited to flat, pointed, concave, convex, rounded, or domed, as desired. The dome shaped portion of the sonication chamber and the rounded horn tip focus the ultrasonic energy transmitted from the horn so as to efficiently reach the desired ultrasonic levels required to lyse cellular material (e.g. ruggedized cell, spores, etc.) and release DNA into the fluid sample with minimal ultrasonic horn power and size requirements. It is preferable for the rounded tip 711a of the domed output portion 711 of the ultrasonic horn to press against the dome 1211 of the sonication chamber 1210 with sufficient force to ensure contact is maintained between the tip of the horn and the domed shaped surface of the sonication chamber during delivery of ultrasonic energy. In some embodiments, the movable mechanism is configured to move the ultrasonic horn upwards (in the engaging direction) to pressingly engage the domes of the sonication chamber and the ultrasonic horn together with at least 0.5 lb-F. In some embodiments, the force applied to ensure that the rounded tip of the horn and the dome portion of the sonication chamber is between about 1 lb-F to about 2 lb-F. In some embodiments, the force applied is about 1.4 lb-F. Although an interfacing cam and wedge are described herein, it is appreciated that various other mechanisms may be used with or without a biasing member to facilitate movement of the horn between the disengaged and engaged positions. For example, in some embodiments, such mechanisms can include a lead screw, cable, and the like.

In some embodiments, the movable mechanism by which the ultrasonic horn is positioned to press against the sonication chamber is integrated within an inter-connector network of actuators that effect movement of various other components of the diagnostic assay system, such as opening and closing of a door of the system, loading and ejection of the assay cartridge from the system, movement of a valve assembly and a syringe assembly within the system. It is appreciated that the movable mechanism may be integrated with actuators of one or more other components or the movable mechanism may be entirely independent of other mechanisms and actuators.

FIGS. 9A-9B illustrates cross-sectional views of a diagnostic assay system during and after loading of an assay cartridge into the system demonstrating a mechanism that positions the ultrasonic horn in coordination with closing of a door of the system and loading of the assay cartridge. FIG. 9A depicts a partially inserted assay cartridge 32 in which a distal facing portion of a base of the assay cartridge begins to engage an ejection tooth of an ejection/loading cam 1120. In this position of the cam 1120, the outer surface of the cam engages an upper surface 721 of the wedge portion 721 of the horn housing, as can be seen in more detail in the side-view and cross-section of FIGS. 11A-1 and 11A-2.

As the assay cartridge 32 is more fully inserted, the assay cartridge presses against the ejection tooth and the ejection/loading cam 1120 rotates clock-wise so that a loading tooth of the cam engages an underside surface of the assay cartridge pulling the cartridge inward to a fully loaded position. As the ejection/loading cam 120 rotates the outer surface 1121 of the cam slides along the wedge tip 721*a* of the wedge portion 721 of the horn housing slide, which presses the horn away from the cartridge to the disengage position, which partly compresses the spring coil 730. As the assay cartridge is fully inserted, the wedge tip 721*a* is received within an inwardly curved portion 1121*a* of the rounded portion of the cam 1120 that allows the horn housing 720 to move upward a short distance allows the coil to at least partly uncompress such that the rounded tip 711*a* of the ultrasonic horn protrudes above the surface along which the assay cartridge was loaded and pressingly engages the dome-shaped portion of the sonication chamber. This position can be seen in more detail in the side view and cross-section of FIG. 11B-1 and FIG. 111B-2, respectively. As can be seen in FIGS. 9A and 9B, rotation of the cam 120 is actuated by a closing movement of the first rack portion 110 of the door rack mechanism, which in this embodiment is downward movement (in the direction of the arrow). Through a network of interrelated gears, this closing movement of the door also simultaneously actuates closing of the door 100 of the system 1000 from an open position in FIG. 9A to facilitate insertion and loading of the assay cartridge 32 to a closed position, as shown in FIG. 9B, after loading of the cartridge. Movement of the door rack mechanism can be effected by one or more motors, such as any of those described herein.

FIG. 10A illustrates a cross-sectional view of an assay cartridge for use in a diagnostic assay system in accordance with some embodiments of the invention. The dome-shaped portion 1211 of the sonication chamber 1210, described above, is positioned on the bottom surface of the assay cartridge. The sonication chamber 1210 is in fluid communication with a network of channels in the assay cartridge, through which fluid is transported by movement of a valve and syringe to effectuate pressure changes during the assay procedure. After the sample is prepared and/or processed, the prepared fluid sample is transported into a chamber of the reaction vessel 33, while an excitation means and an optical detection means are used to optically sense the presence or absence of a target analyte (e.g. a nucleic acid) of interest (e.g., a bacteria, a virus, a pathogen, a toxin, or other target analyte). It is appreciated that such a reaction vessel could include various differing chambers, conduits, micro-well arrays for use in detecting the target analyte. An exemplary use of such a reaction vessel for analyzing a fluid sample is described in commonly assigned U.S. Pat. No. 6,818,185, entitled "Cartridge for Conducting a Chemical Reaction," filed May 30, 2000, the entire contents of which are incorporate herein by reference for all purposes.

VII. C. Sonication Horn Control

In some embodiments, operation of the ultrasonic horn is performed by use of a horn control circuit configured to control current amplitude and phase estimation in a manner to optimize excitation and provide consistent robust delivery of ultrasonic power, which is proportional to current at fixed voltage, as needed for a particular assay. In some embodiments, the system provides entirely digital control of sonication power delivery. In some embodiments, the system provides operation of the ultrasonic horn without conventional transformer and full-wave rectification analog circuitry, thereby allowing for decreased power usage, reduced horn assembly size and an overall reduction in size of the system. In some embodiments, the power delivery and control is performed so as to control real power (which is total power) into the ultrasonic horn (as opposed to reactive power). The control circuit is configured to apply a programmable sonication power for a programmable duration to the assay cartridge to lyse the target cells as needed for a particular assay.

Figure 12A:
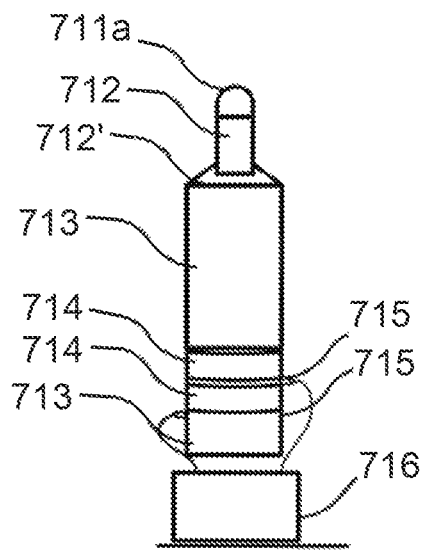
FIG. 12A illustrates an exemplary ultrasonic horn and FIG. 12B illustrates a control diagram for operation of an ultrasonic horn in accordance with some embodiments of the invention.

In some embodiments, (e.g. with reference to FIG. 12A), an ultrasonic horn includes a mass 713 (typically a solid core of metal) adjacent one or more piezo-electric actuators 714 that vibrates when connected to a power supply 716 through electrical contacts 715. The solid mass includes a tapered portion 712' leading to an elongated portion 712 that focuses the ultrasonic wave and terminates in a domed output portion 711 that further focuses the ultrasonic waves for output at the tip 711*a* of the domed outputportion 711. Typically, multiple piezo-electric actuators can be used to provide greater ultrasonic output with lower relative requirement (as compared to one actuator suited to deliver higher ultrasonic energies).

In some embodiments, the horn assembly can utilize an off-the-shelf horn with a horn control circuit that operates the horn with a closed loop or feedback control that provides consistent, robust ultrasonic energy at desired levels with lower relative power requirements than would otherwise be possible with the horn. For example, such an off-the-shelf horn having multiple piezo-electric actuators when operated to deliver ultrasonic energy levels suitable for lysing of cells in a diagnostic assay may not operate consistently by merely applying a set current level due to the actuators operating out of phase. The piezo-electric actuators expand outward when current is applied and if this outward expansion occurs at even slightly different times (out-of-phase), then the result is low-frequency coupling into vibration that prevents the horn from delivering suitable levels of ultrasonic energy. For this reason, such horns may only operate properly at lower ultrasonic levels or may not be depended upon to provide consistent delivery of energy for the duration needed in a particular diagnostic assay.

In some embodiments, the system applies an improved control scheme that allows for consistent delivery of levels of ultrasonic energy suitable for lysing of cells in a diagnostic assay for a specified duration using such a horn as described above. In some embodiments, the horn assembly is configured to employ resonant piezo-electric actuators to apply vibration at a frequency of about 50.5 kHz. In some embodiments the horn assembly is configured to apply vibration frequency in a range from about 20 kHz to about 50 kHz. For example, the vibration frequency can be about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or about 50 kHz. In some embodiments, the vibration frequency is more than 50 kHz. In some embodiments, the system utilizes a closed-loop control system to provide excitation of the piezo-electric that is maintained in-phase with each other for the duration required for sonication of biological material.

Figure 10B:
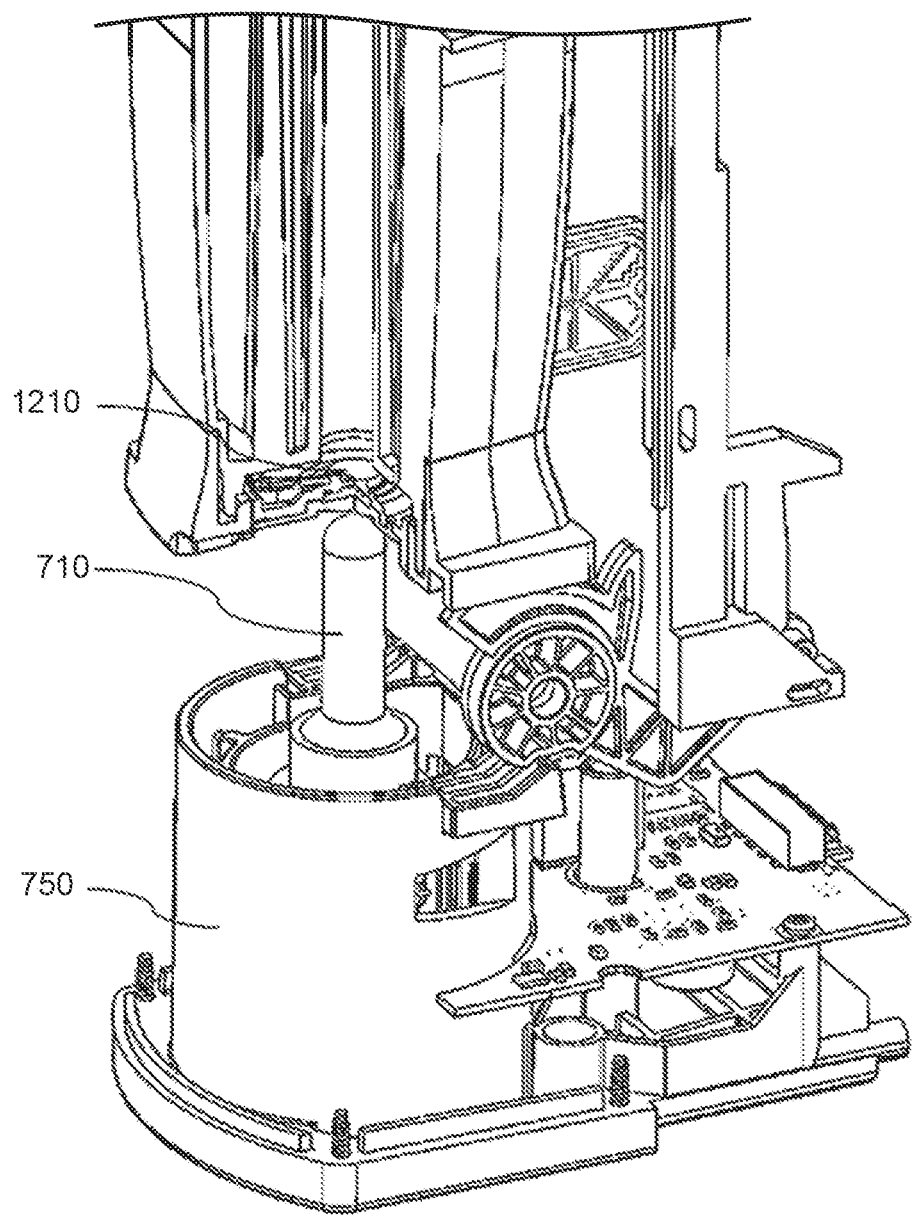

In some embodiments, the system applies current and/or voltage to the piezo-electric actuators by ramping up the applied power to the desired levels to minimize occurrences of out-of-phase excitation. An example of this scheme is shown in FIG. 10B. In some embodiments, the power delivery and control is performed so as to control real power (which is total power) into the ultrasonic horn (as opposed to reactive power). By substantially maintaining a specified phase relationship between voltage and current, allows reactive power to be substantially eliminated. The reactive power is when the piezo actuators are not in locked phase and the horn merely vibrates. By ramping up the power, as opposed to just turning the power on, the ramp allows the system to maintain the phase relationship between current and voltage and prevent vibration to allow the horn to deliver the desired ultrasonic energy levels required.

Figure 12B:
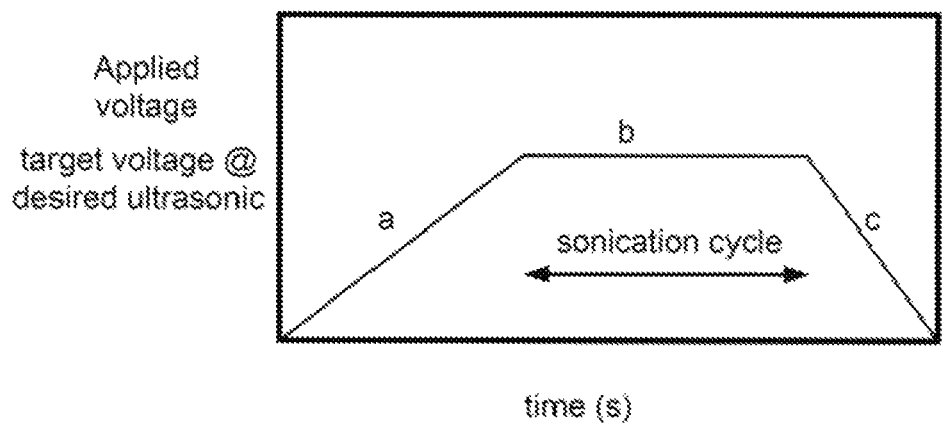

FIG. 12B illustrates a simulated horn power transfer function demonstrating the phase relationship between excitation current and voltage at the power resonance.

Figure 14:
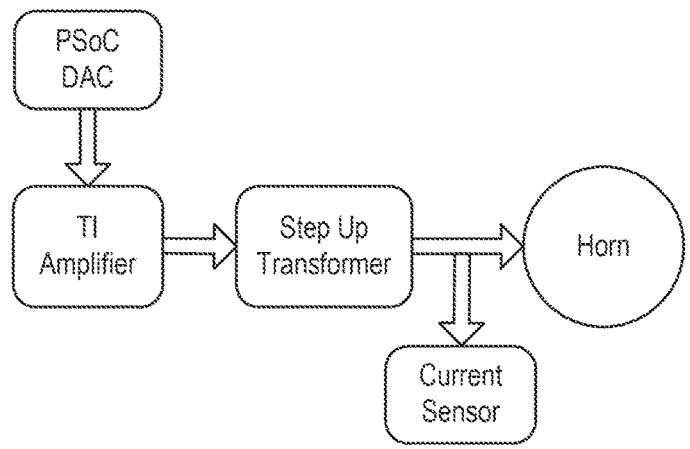
FIG. 14 illustrates a control schematic of a horn assembly in accordance with some embodiments of the invention.

In some embodiments, the horn control circuit uses closed control loops to operate the horn. In an inner control loop, the frequency is adjusted to maintain the present phase relationship. In an outer loop, the amplitude of the voltage excitation is continually adjusted to maintain the commanded power level. An example of these inner and out control loops is illustrated in FIG. 14.

Figure 13:
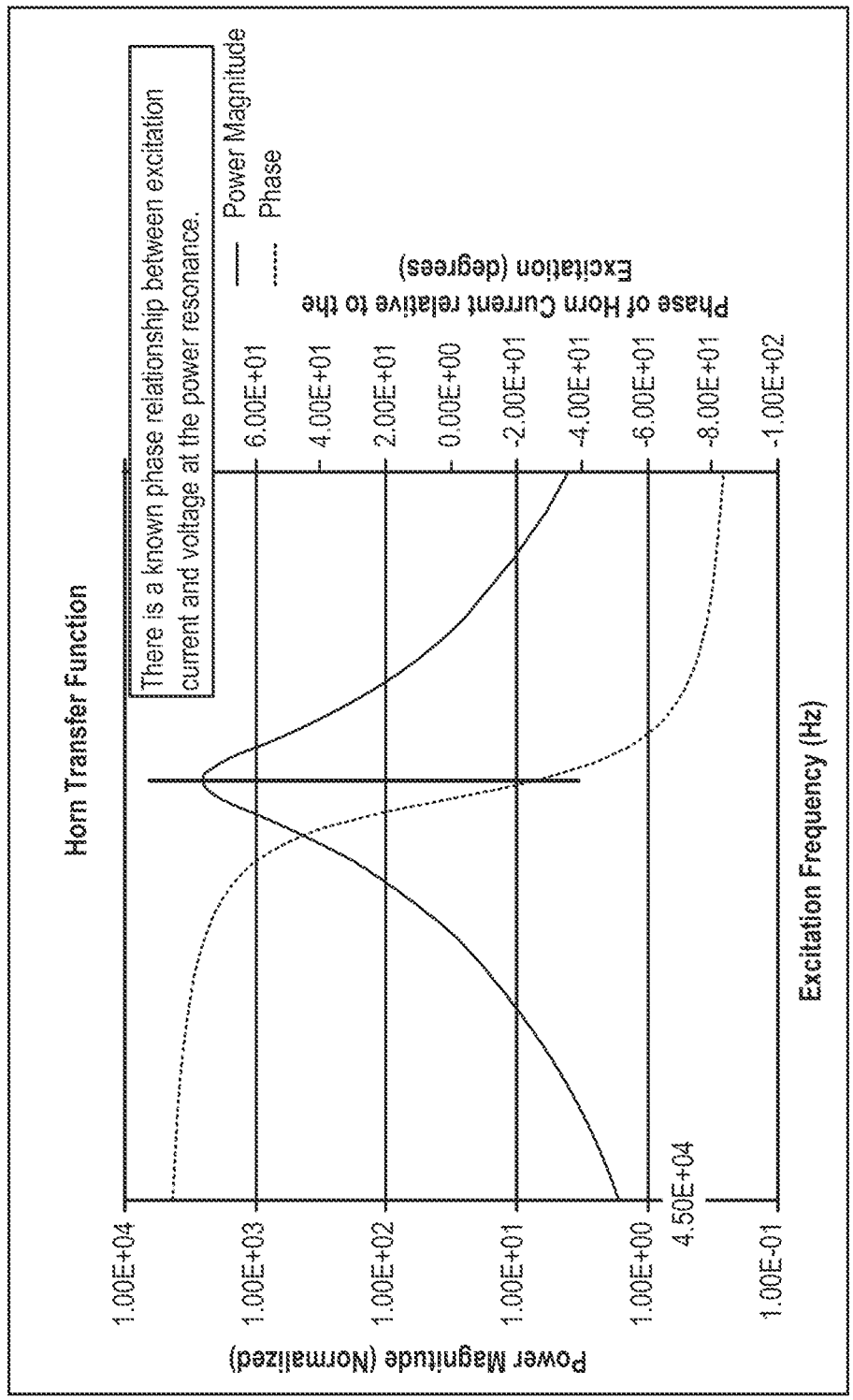
FIG. 13 illustrates a transfer function for control of a horn assembly in accordance with some embodiments of the invention.
Figure 15:
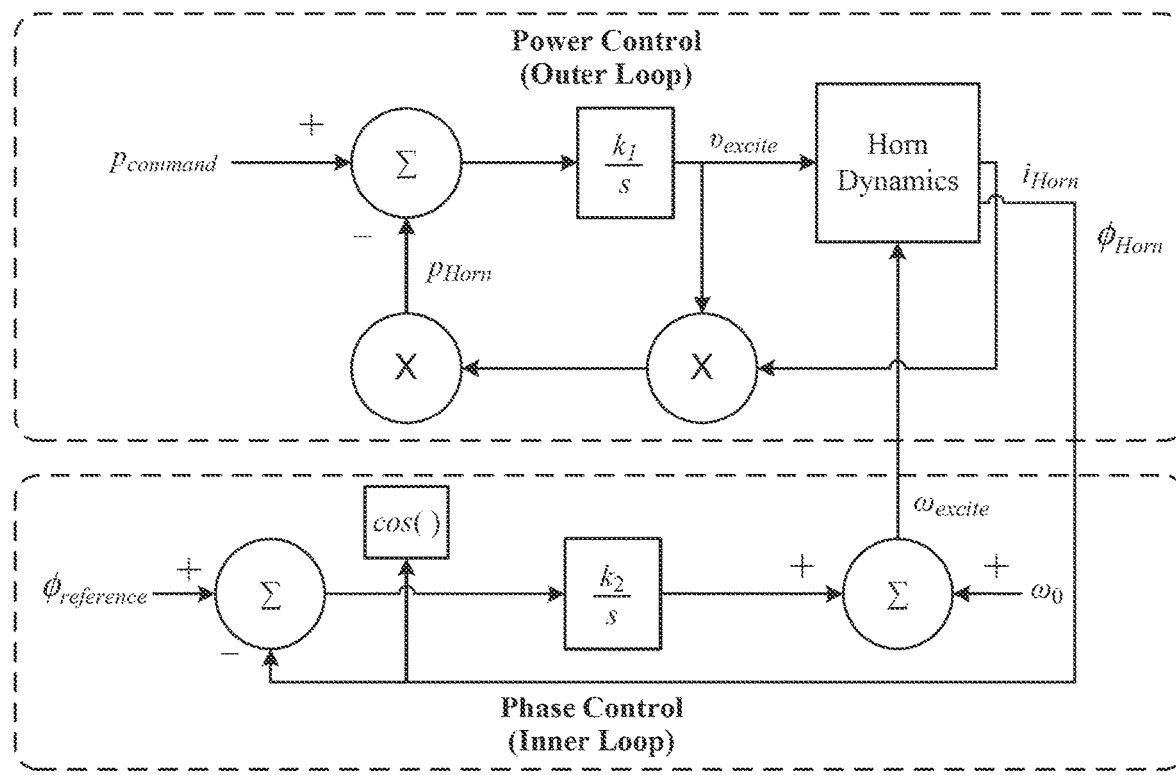
FIG. 15-17 illustrate control diagrams for a horn assembly in accordance with some embodiments of the invention.

FIG. 13 illustrates a control schematic of the sonication horn assembly in accordance with some embodiments of the invention. The sonication interface is configured in power (Watts) and duration (seconds) as needed for a particular assay. Typical power levels of 5-10 Watts are applied for between 15-30 seconds to sufficiently lyse typical spore cells and releasing 50% of spore-bound DNA into solution within the sample chamber 1210, as shown in FIG. 10B. It is appreciated however, that power, duration and required sonication efficiency vary by assay and can be greater or lesser than the levels described depending on assay needs, design and the type of cells or material being sonicated. In some embodiments, the PSoC DAC generates a 0-4V sine wave. The DAC output goes through a TI audio amplifier. The TI amplifier multiplies the signal by 20 db. The TI amplified signal goes through a step up transformer before being delivered to the horn. Power is estimated by the voltage (DAC voltage amplified through TI and the transformer) and the current read by the sensor (P=v*I cos(Φ)) (real power). Thus, power delivered to the horn is controlled via controlling the DAC voltage. A control loop drives the input voltage to keep the power at the desired level. See for example FIG. 15.

Figure 16:
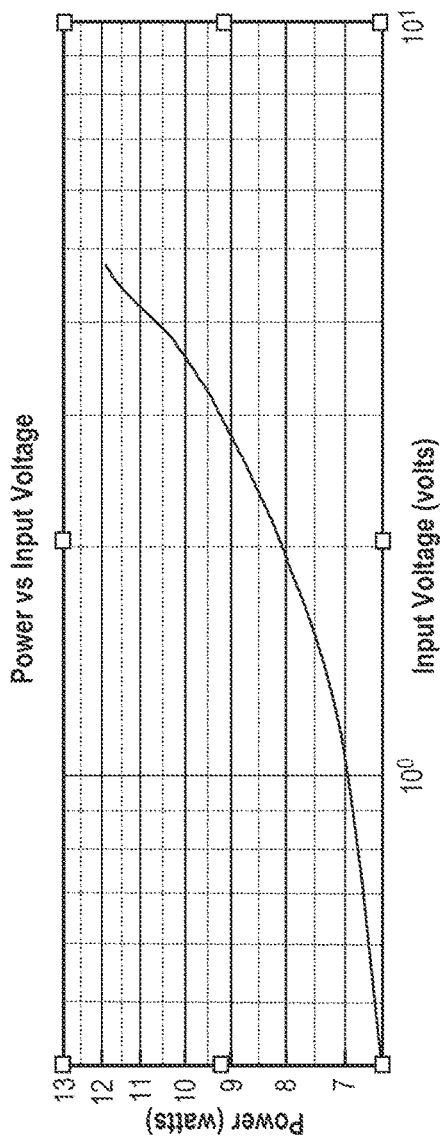
Figure 17:
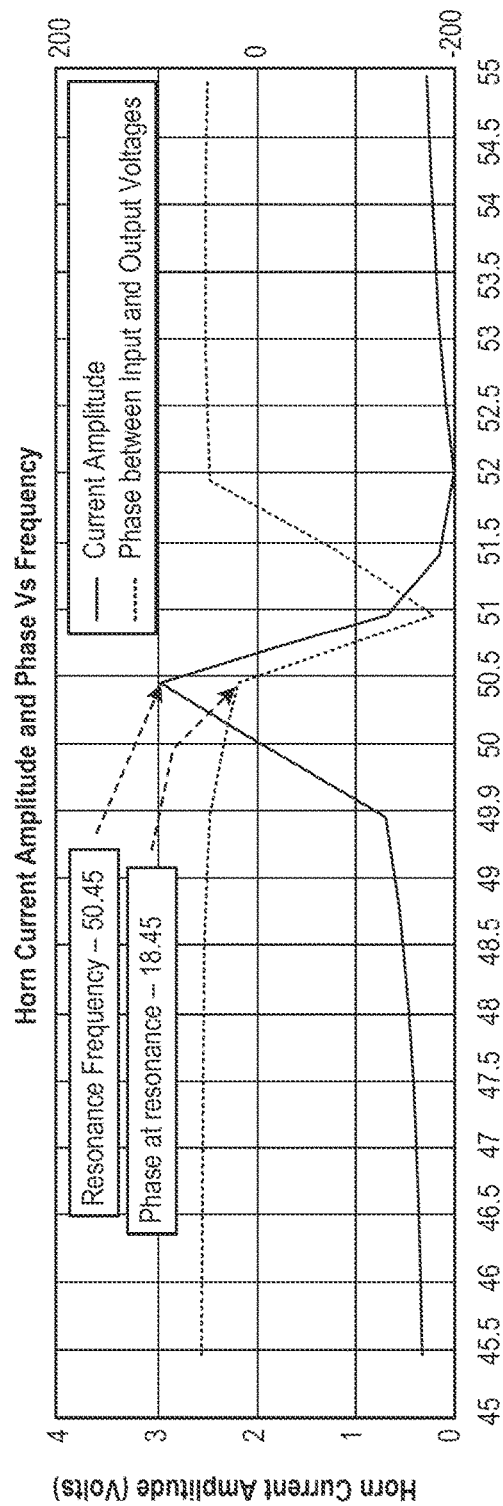

In some embodiments, the horn control circuit is configured so that a frequency that gives the highest real power amplitude from a frequency sweep is established as the resonance frequency. The phase between the input voltage and the output voltage is measured at the resonance frequency. During sonication, a control loop locks the measured phase between input and output voltages by adjusting the input frequency. Current amplitude is a product of sensor factor and the PSoC amplifier that amplifies the signal before reading. An exemplary relationship between power vs input voltage can be seen in FIG. 16. An exemplary relationship between the horn current amplitude and phase versus frequency can be seen in FIG. 17.

In some embodiments, the horn control circuit utilizes a sinusoidal control that controls amplitude input to the horn driver. The circuit can utilize phase-matching for resonant frequency control to ensure the voltage and current maintain a specified phase relationship, which can be used for instance to eliminate reactive power. In some embodiments, the circuit utilizes frequency sweeping with a 1 Hz resolution, however, it is appreciated that this configuration can provide effectively unlimited frequency resolution. Such configuration allows for consistent and robust delivery of ultrasonic energy levels with an ultrasonic horn having reduced power and size requirements than would otherwise be possible with such a device.

VIII. Thermal Optical Subassembly

In some embodiments, the invention provides a Thermal Optical Subassembly (TOS) for use in a diagnostic assay system. In some embodiments, the TOS includes a thermal control device component and an optical excite/detect component. The TOS may interface with other components of the diagnostic assay system, including the ultrasonic horn, the door, syringe and valve. In some embodiments, the TOS includes a thermal control device instrument and an optical component instrument having an excitation means and an optical detection means. The TOS unit is constructed so as to define a cavity in which a reaction vessel can be inserted for performing nucleic acid amplification and/or detection of a target analyte using the thermal control component and optical interrogation of the target analyte using the optical component instrument. The TOS is employed in a system with one or more circuit boards (e.g. motherboard) that control operation and coordination between the various components of the assay system. In some embodiments, a Cell Core piggy backs onto the motherboard. In some embodiments, each hardware subassembly carries their own dedicated PSoC processor and associated electronics. In some embodiments, the diagnositc assay system includes a communication means (e.g. wireless, NFC, USB) that allows modification and/or updating of the control software or control parameters utilized by the system. The TOS can also include one or more sensors (e.g. NFC reader) to determine a location or presence of an assay cartridge or a position of the valve component so as to coordinate operation of multiple components of the system. In some embodiments, the TOS comprises a cartridge position sensor (e.g. NFC reader) located physically on the TOS to allow it to be physically in close proximity to the assay cartridge when inserted into the diagnostic assay system. In some embodiments, the TOS can be serially connected other electronic subsystems via USB and/or wireless interfaces like NFC or bluetooth.

VIII. A. TOS Design

It is appreciated that the thermal control device instrument and the optical detection device can be defined in various configurations, as desired. In the embodiments described herein, the thermal control and optical detection device is configured for use with a reaction vessel having two opposing major faces and two edges (minor faces). The thermal control device can be configured for one-sided heating of one major face of the reaction vessel, or two-sided heating of both the major faces. In the embodiments described herein, the thermal control device is configured to be positioned adjacent a major face of the reaction vessel on one or both sides. Likewise, the optical detection detection device can be configured according to various configurations, such as optical detection from a major face of the reaction vessel or from one or more edges (minor face(s)) of the reaction vessel. Typically, the optical detection configuration corresponds to a configuration of the thermal control device, for example, the optical detection device is positioned to detect optics through a part of the reaction vessel not covered by the thermal control device. In some embodiments, where one sided heating is used, the opposing non-heated major face can be covered with a transparent insulating material so as to control heat transfer while still allowing for optical detection through the insulating material. In some embodiments, the system utilizes a thermal control device configured for one-sided heating and an optical detection device configured for excitation/detection from a major face and/or one or more edges (minor face) of the reaction vessel. In other embodiments, the system utilizes a thermal control device configured for two-sided heating with an optical detection device configured for optical excitation/detection from one or more edges of the reaction vessel. Exemplary configurations are provided below.

Figure 18:
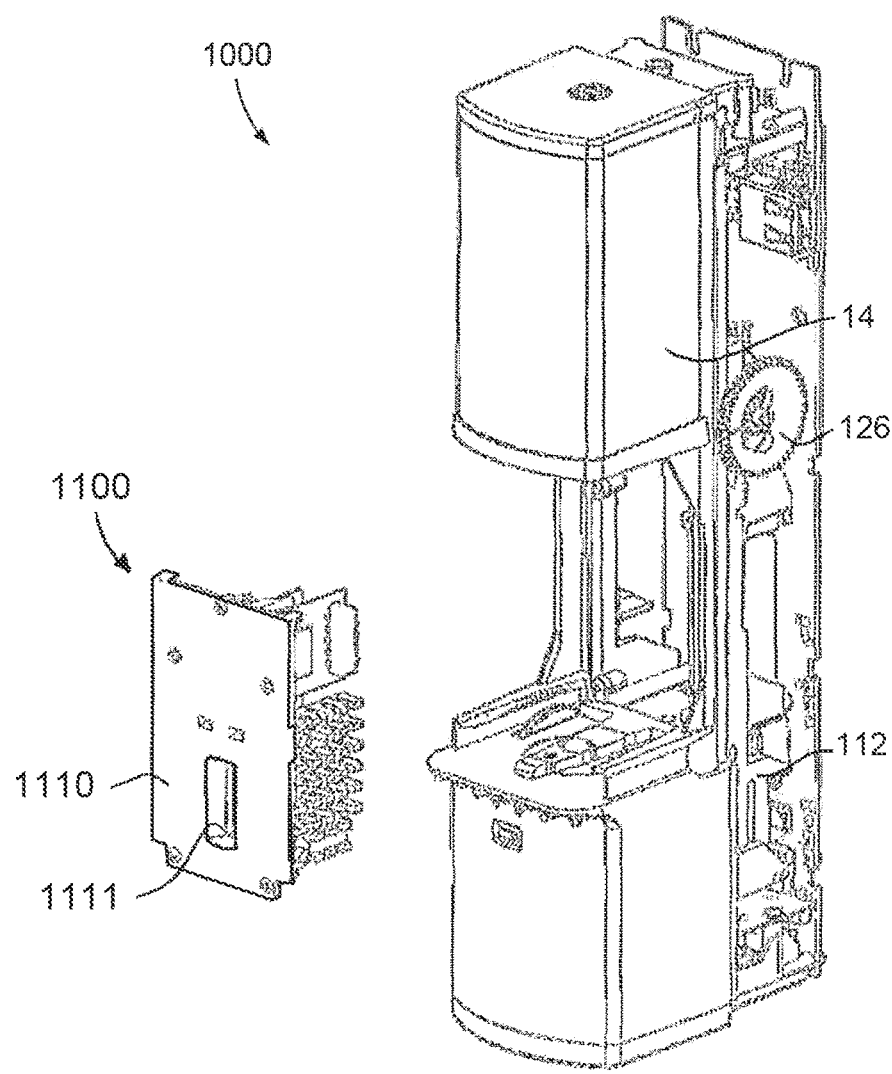
FIG. 18 illustrates an exemplary TOS sub-assembly before insertion into the assay module in accordance with some embodiments of the invention.

FIG. 18 shows an exemplary diagnostic assay system 1000 for performing detection of a target analyte in a fluid sample prepared within a disposable assay cartridge (not shown) when inserted into the system. The diagnostic assay system 1000 includes multiple components and subassemblies, as described herein, one of which is the TOS subassembly 1100. As shown in FIG. 18, the TOS 1100 subassembly can install from the front of the system. The TOS can be inserted into the frame or housing of the system 1000 with the door 14 open and secured with one or more screws (not shown) so that the front plate 1110 faces into the receptacle of the system that receives the assay cartridge. The front plate 1110 defines a cavity opening or slot 1111 through which a planar reaction vessel of an assay cartridge can be inserted. In some embodiments, the TOS can be tested as a stand-alone sub-assembly before insertion into the diagnostic assay system. In some embodiments, the TOS can be removed or replaced as needed.

In some embodiments, the diagnostic assay system uses a disposable assay cartridge. An exemplary assay cartridge suitable for use with the system as described herein is described in U.S. Pat. No. 6,818,185, entitled "Cartridge for Conducting a Chemical Reaction," filed May 30, 2000, the entire contents of which are incorporate herein by reference for all purposes.

In some embodiments, the TOS slot 1111 and cavity is dimensioned so as to accommodate the reaction vessel (typically within +/−0.020″) and the optical mount and associated components are adapted to locate the optical components relative to the reaction vessel to facilitate excitation and optical detection for the target analyte. In some embodiments, the TOS is spatially configured to locate a thermal control device, such as a dual-TEC device, relative to the reaction vessel to control and facilitate thermal cycling of the fluid sample within the reaction vessel of the assay cartridge. In some embodiments, the TOS moves the thermal control device, for example, retracting the dual-TEC before insertion of the reaction vessel and then engages and clamps the dual-TEC against the reaction vessel when the reaction vessel is in place.

Figure 19A:
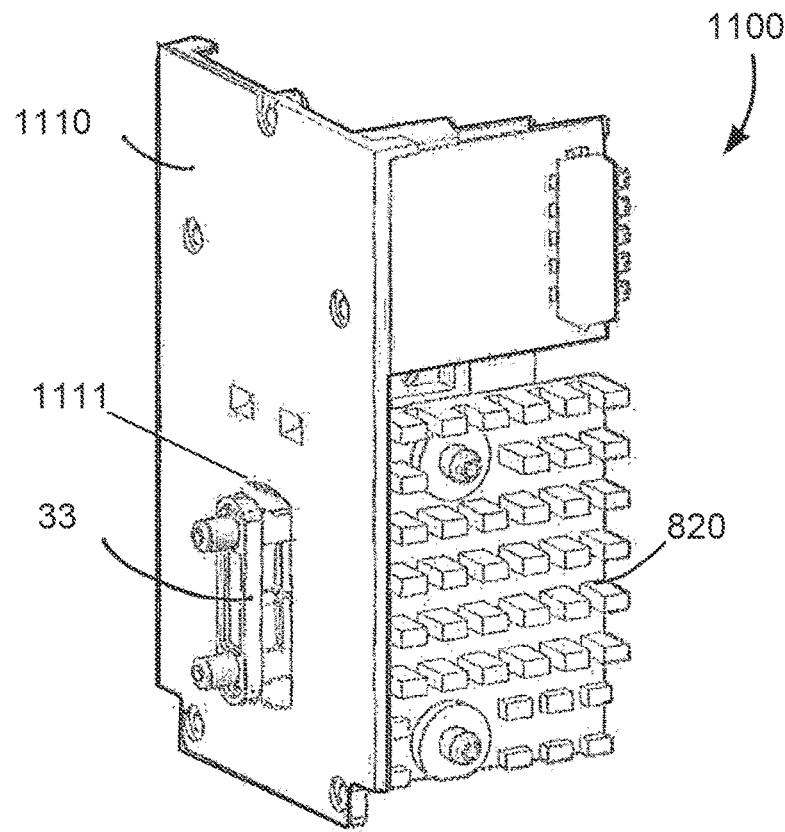
FIGS. 19A-19B illustrates front and rear views of an exemplary TOS sub-assembly in accordance with some embodiments of the invention.
Figure 19B:
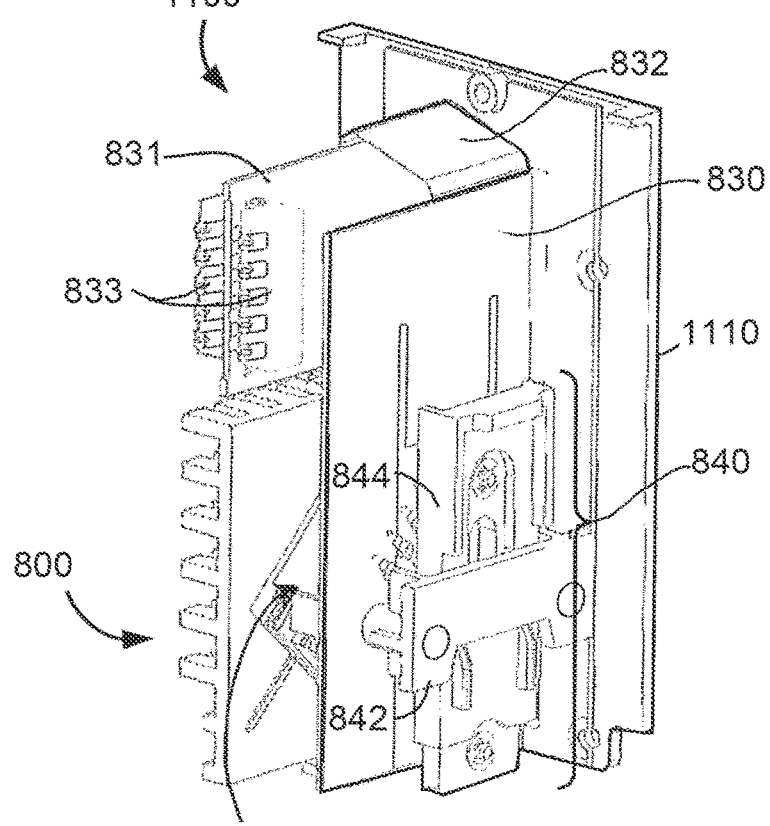
Figure 26A:
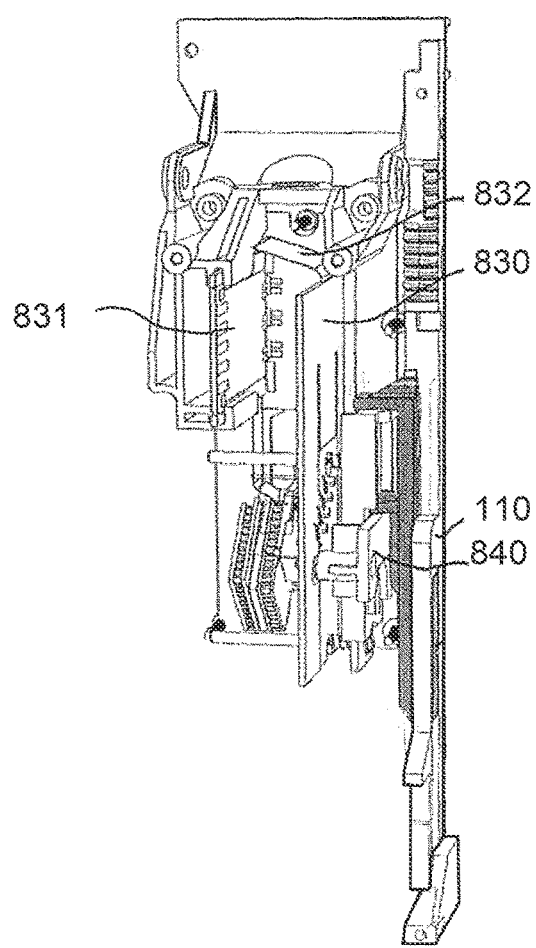
FIGS. 26A-B illustrates an exemplary thermal control device component movably coupled with a slide base actuated by a door rack of the module in accordance with some embodiments of the invention.
Figure 26B:
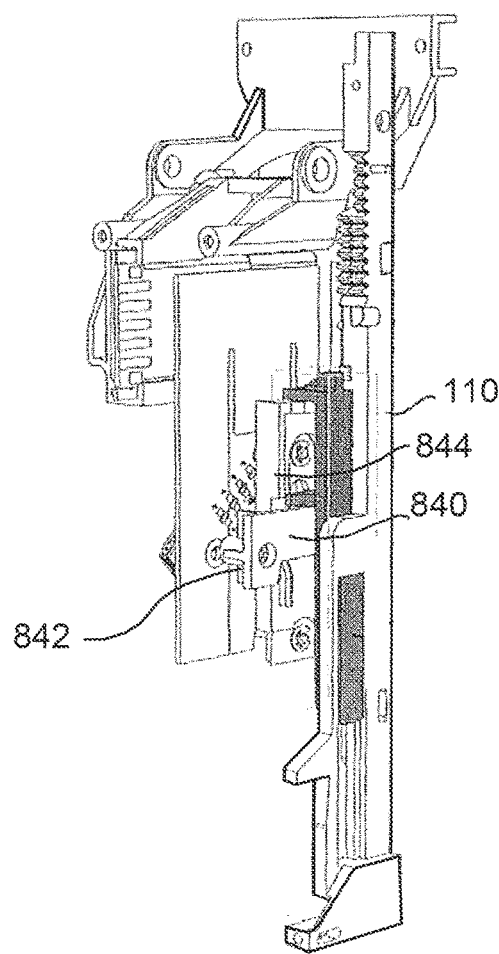

FIGS. 19A-B illustrates front and rear views of an exemplary TOS sub-assembly 1100 in accordance with some embodiments of the invention. In FIG. 19A, an exemplary reaction vessel 33 is shown inserted into the cavity opening 1111 of the front plate 1110 and the thermal control mount/heat sink 820 can be seen, as well as a cooling fan 822 (see FIG. 20B). In FIG. 19B, a rigid flex PCB configuration and thermal contact mechanism 840 allowing for lateral movement of the thermal control device prior to clamping engagement of the reaction vessel 33 can be seen. The PCBs 830 and 831 through which the thermal control device 800 and the optical component 900 are powered and controlled can be coupled through a rigid flex connection 832 that allows for lateral movement. Thermal contact mechanism 840 includes a slidable component that translates movement between an open configuration (see FIG. 24B) and a clamped configuration (see FIG. 24A) in which a TEC face 810 of the thermal control device is engaged against the side of a reaction vessel 33. In some embodiments, thermal contact mechanism 840 includes a movable and/or adjustable bracket 842 that can slide up and down along a vertically extending mount 844 to ensure proper alignment with the optical component 900 and the reaction vessel, and is movable laterally toward thermal the thermal control device to ensure suitable thermal contact with the reaction vessel 33 to facilitate efficient thermal cycling. In some embodiments, the thermal contact mechanism 840 includes a bottom support or guide 846 to facilitate insertion of the reaction vessel within the thermal contact mechanism 840.

and the In some embodiments, this movement is effected by axial movement of the door drive rack 110 as shown in FIGS. 26A-B.

Figure 20A:
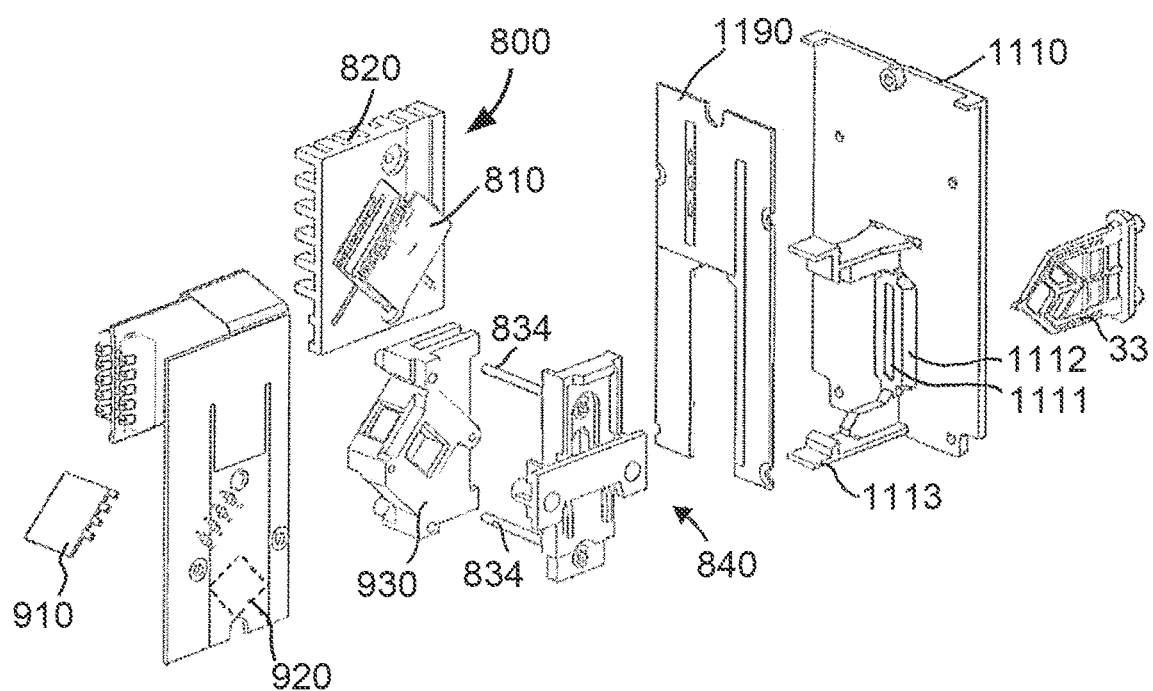
FIGS. 20A-20B illustrates exploded views of an exemplary TOS in accordance with some embodiments of the invention.
Figure 20B:
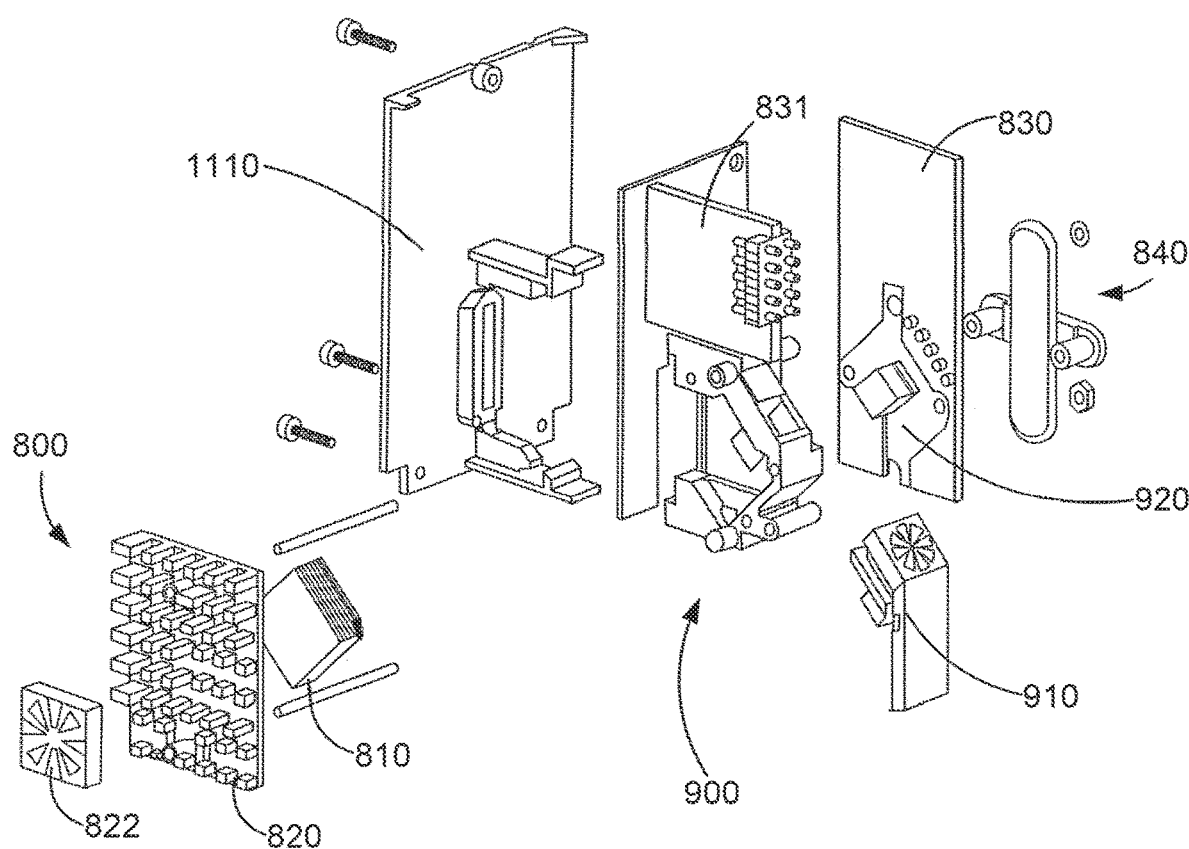

FIGS. 20A-B illustrates exploded views of an example TOS in accordance with some embodiments of the invention. As can be seen, the TOS assembly includes an optical mount 930 having windows through which the excitation component 910 and optical detection component 920 can operate when assembled. The optical mount is attached to the front plate 1110 through a bracket 1113 and at least partly surrounds the flange 1112 around the reaction vessel opening 1111. The thermal control device 800 is coupled to the optical mount 930 by two pins 834 that extend through the thermal contact mechanism 840 and two holes through the optical mount 930. The assembly may also include a sensor for detecting a proximity location, or identity of the cartridge within the system. In some embodiments, the sensor is a near field communication (NFC) sensor 1190, although it is appreciated that various other sensors can be used. It is appreciated that, in some embodiments, the NFC can be adapted to detect various differing things, including but not limited to: the location/presence of a cartridge, the type of cartridge, the particular assay, the microfluidic procedures that are unique to a particular assay, the presence of a mobile device (e.g. PDA) and various other lot specific parameters. In some embodiments, the NFC allows for a work flow associated with a particular system/cartridge, thereby obviating the need for a separate database in the cloud that the diagnostic assay system would otherwise have to access. This feature is particularly useful in a resource limited settings where internet may not be readily available.

Figure 21A:
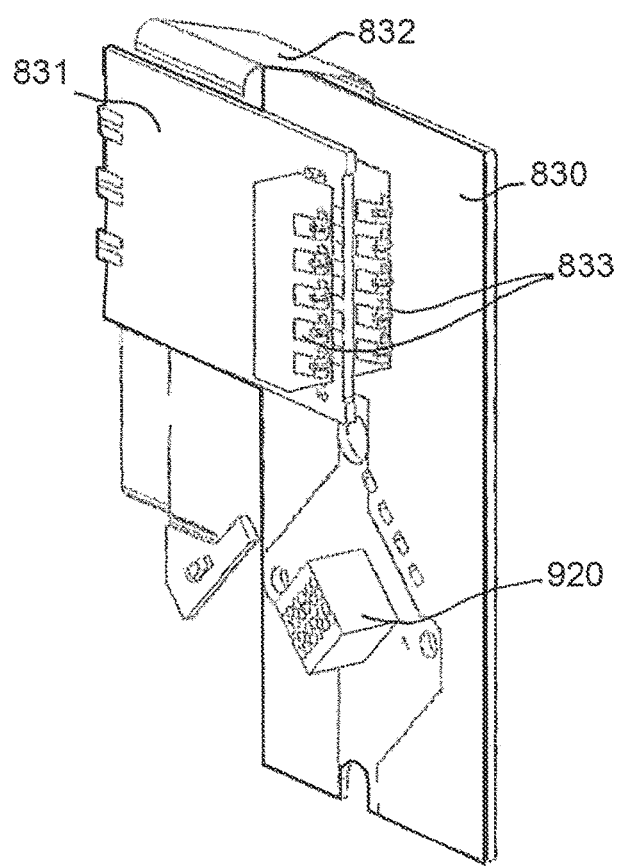
FIGS. 21A-B illustrates optical components and associated PCBs of an exemplary TOS in accordance with some embodiments of the invention.
Figure 21B:
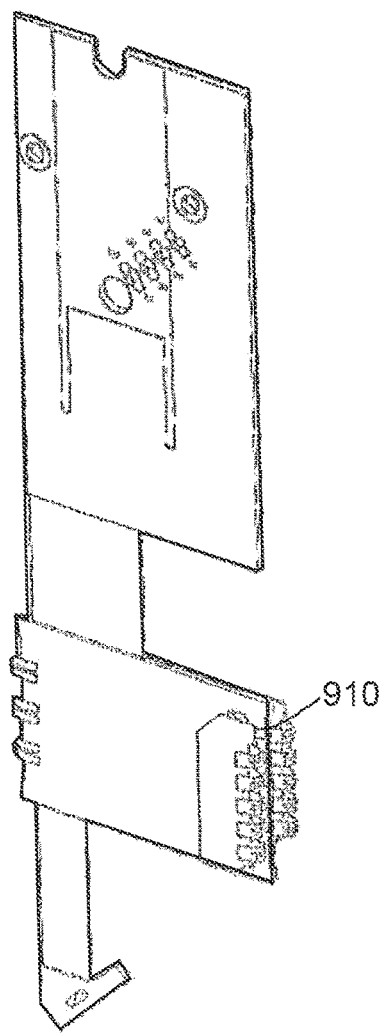
Figure 22A:
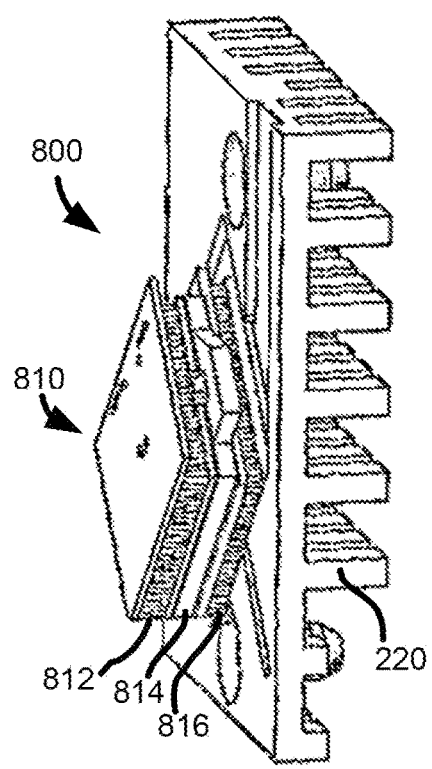
FIGS. 22A-B illustrates exemplary thermal control device components and associated PCB with a rigid flex connection in an example TOS in accordance with some embodiments of the invention.
Figure 22B:
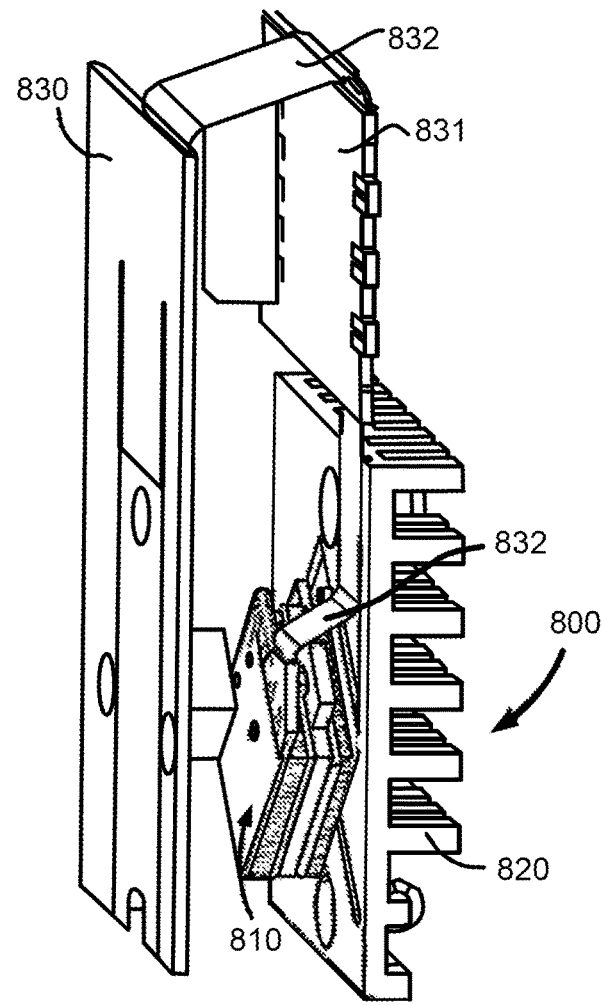

FIGS. 21A-B illustrates optical components and associated PCB of an exemplary TOS in accordance with some embodiments of the invention. The optical components include an excitation component 910, an optical detection component 920 and associated PCB components 830, 831 and electrical circuitry 833. In some embodiments, the PCBs are connected through a rigid flex connection 832 that allows for lateral movement of the thermal control device against the reaction vessel. FIGS. 22A-B illustrates thermal control device components and associated PCB with a rigid flex connection in an exemplary TOS. FIGS. 23A-B illustrates a thermal control device 800 before being attached to the optical mount 930 of an exemplary TOS. In some embodiments, the optical mount 930 includes an alignment feature 931 to ensure proper alignment between the optical component 900 and a reaction chamber portion of the reaction vessel 33. The alignment feature can include one or more features that engage with corresponding features of the reaction vessel, for example, a hole that receives a distally extending pin of the reaction tube, a bump or ridge that engages a corresponding recess of the reaction vessel, a pair of magnets, or any suitable features to facilitate alignment between the reaction vessel and the optical component 900.

Figure 24A:
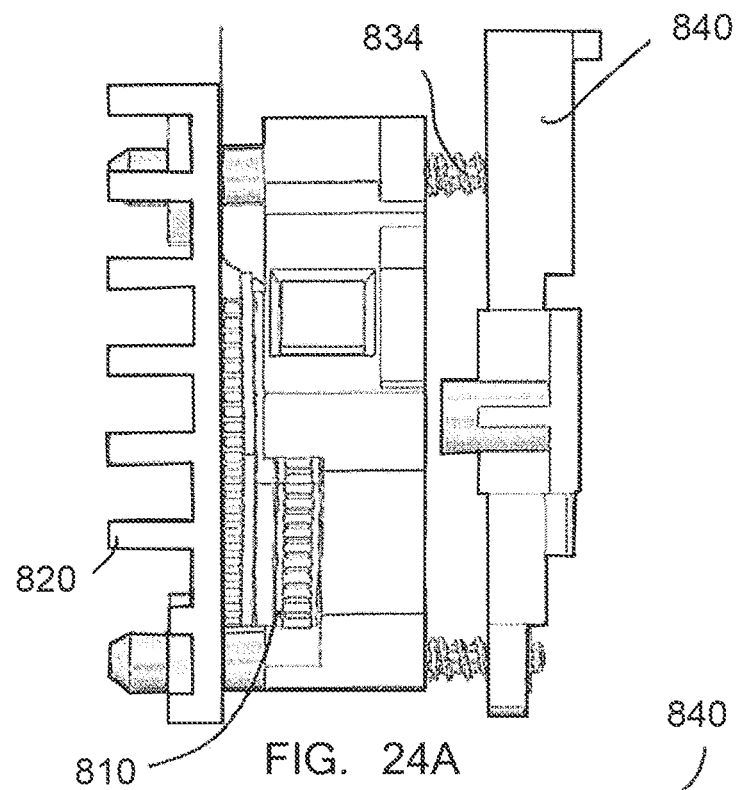
FIGS. 24A-B illustrate an exemplary thermal control device component movably coupled to an optical mount in an open configuration and a clamped configuration, respectively, in accordance with some embodiments of the invention.
Figure 24B:
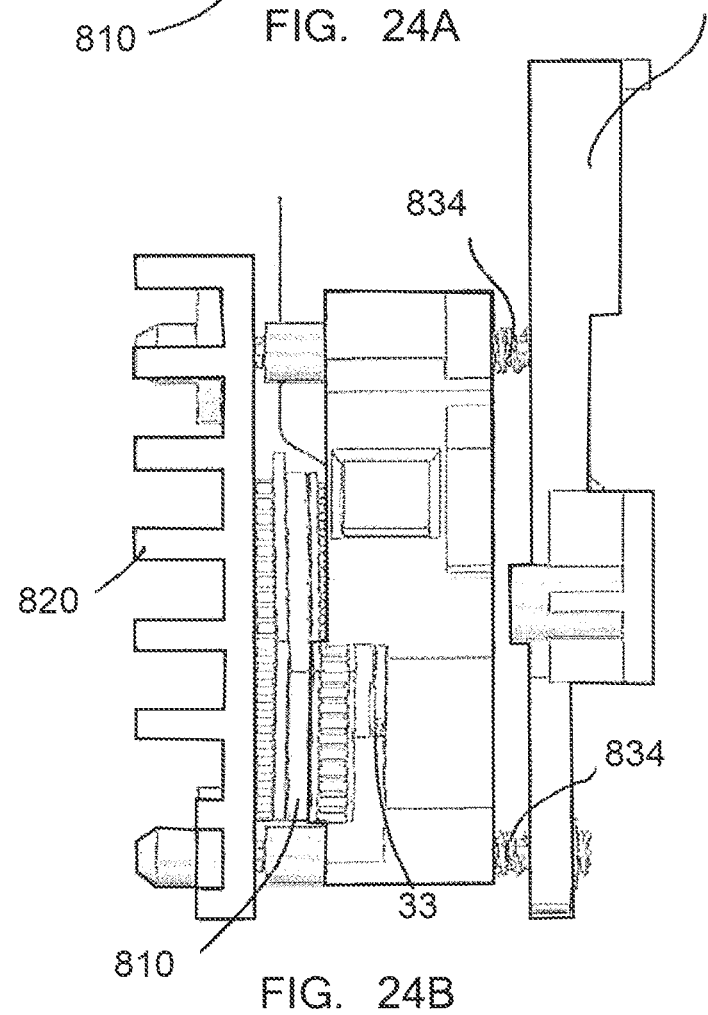
Figure 25:
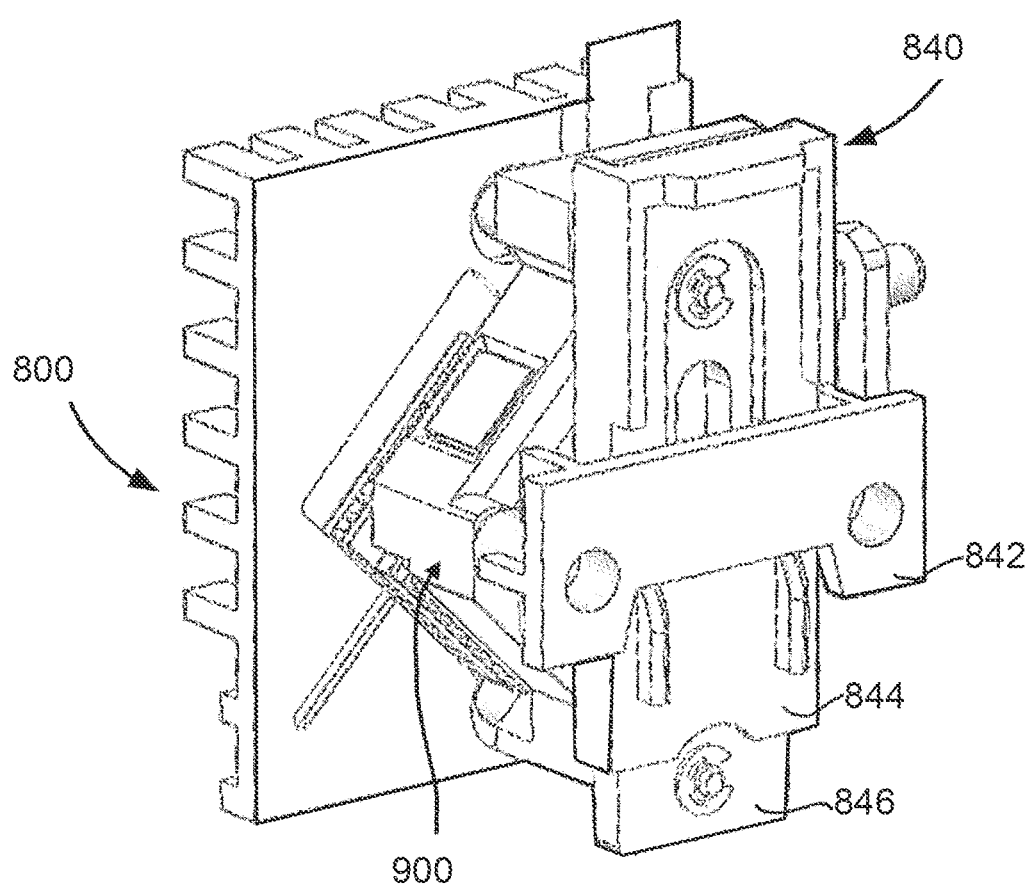
FIG. 25 illustrates an exemplary thermal control device component movably coupled to an optical mount and a slide base in accordance with some embodiments of the invention.

FIGS. 24A-24B and 25 illustrate a thermal control device component movably coupled to an optical mount and a slide base in accordance with some embodiments of the invention. In some embodiments, the thermal control mechanism 840 pressingly engages against the reaction vessel of an assay cartridge. In some embodiments, the force applied to engage the thermal control device against the reaction vessel is at least 1 lbs-F. In some embodiments the amount of force used is between 1 and 3 lb-F, typically about 1.3 lbs-F clamping, to ensure the TEC stays parallel to and in sufficient contact with a major face of the reaction vessel 33. FIGS. 26A-B illustrate operation of the door rack 110 effecting lateral movement of the thermal control device between the clamped and open positions (see FIG. 24A-B, respectively).

Figure 28:
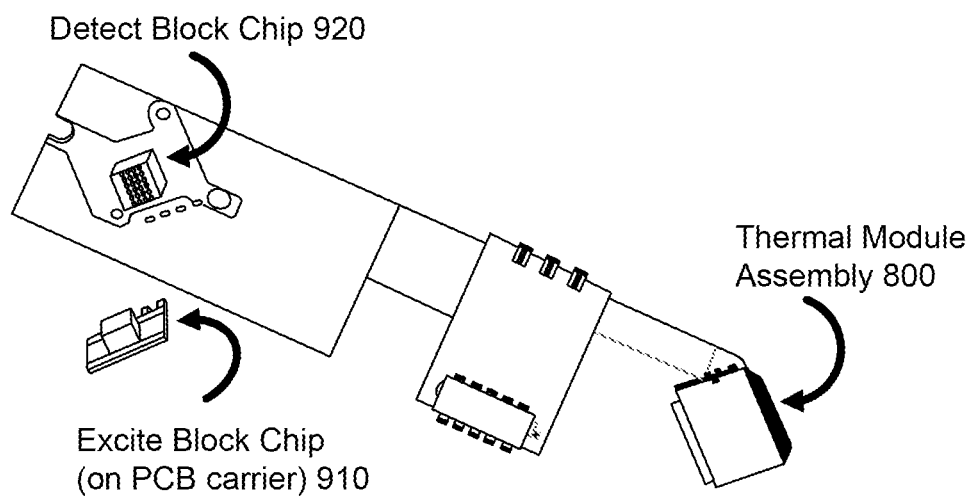
FIG. 28 illustrates an exemplary schematic of optical and thermal control components of the TOS in accordance with some embodiments of the invention.
Figure 29:
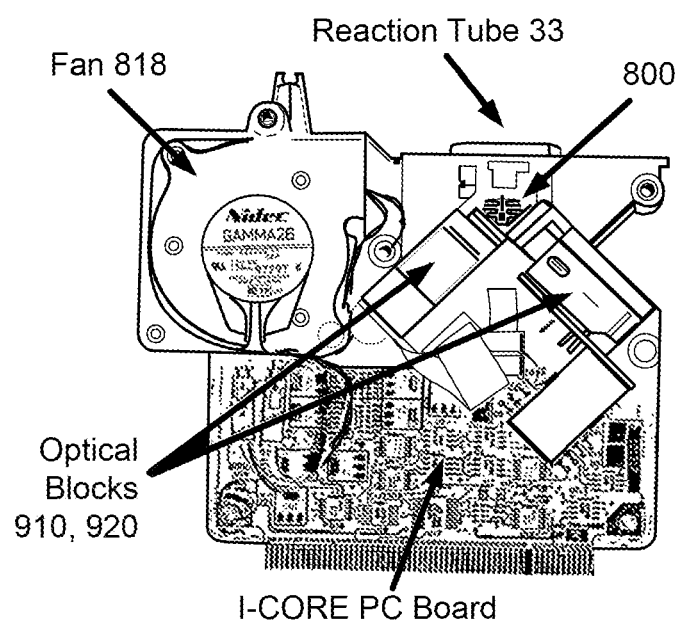
FIG. 29 illustrates an exemplary TOS for use in a diagnostic assay system in accordance with some embodiments of the invention.

FIG. 28 illustrates a schematic of the optics module and thermal module assembly 810 of the TOS in accordance with some embodiments of the invention. The optics module includes a detect block chip or detection component 920 and an excite block chip or excitation component 910 disposed on a PCB carrier. FIG. 28 illustrates an exemplary TOS for use in a diagnostic assay system as disclosed herein.

VIII. B. Optical Component

Figure 30A:
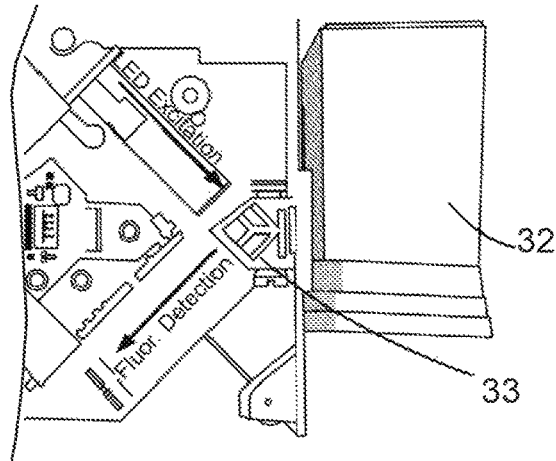
FIGS. 30A-B illustrate two exemplary optical component configurations for use with a reaction vessel in a diagnostic device in accordance with some embodiments of the invention and FIG. 30C illustrates a detailed schematic of an exemplary optical component configuration in accordance with some embodiments of the invention.
Figure 30B:
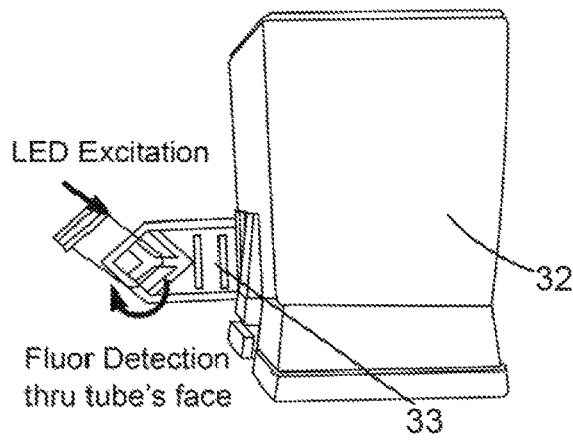

FIG. 30A illustrates an exemplary optical component configuration for use with a diagnostic assay system as disclosed herein and FIG. 30B illustrates a detailed schematic of an exemplary optical component configuration in accordance with some embodiments of the invention. In some embodiments, the optical excitation and detection means operate through a minor face (edge) of a reaction vessel of an assay cartridge while the thermal control device engages against one or more opposing major faces of the reaction vessel. In some embodiments, the thermal control device component thermally engages a major face of the reaction vessel on one side. In some embodiments, the thermal control device component thermally engages a major face of the reaction vessel on both sides. This latter configuration can be particularly useful for heating and cooling of larger fluid sample volumes. Such configurations can use ceramic plate heaters to heat and passive cooling (e.g. ambient air blown across the ceramic heaters) means to achieve the thermocycling of the fluid in the reaction vessel or can include any of the TEC configurations described herein.

Figure 30C:
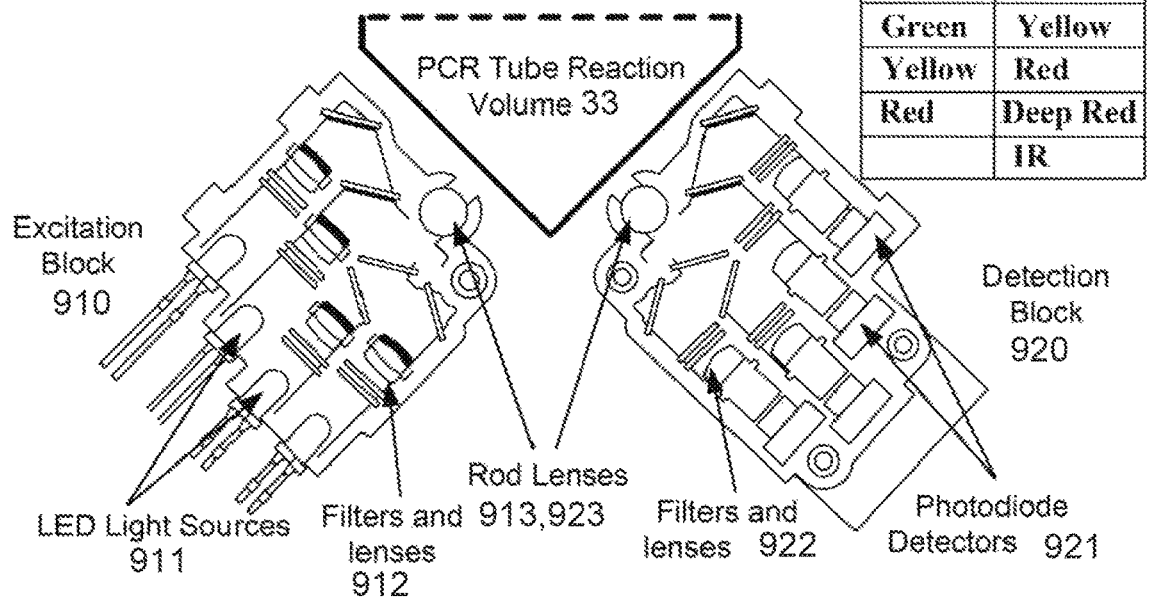

In accordance with some embodiments of the invention, a miniaturized LED excite chip that can excite the fluid sample through a minor edge of the reaction vessel, while a miniaturized detect chip collects fluorescence through a major face of the reaction vessel 33, as in the configuration shown in FIG. 30B. In addition, the dual TEC design provides controlled heating and cooling through the opposite face, which provides improved temperature control as compared to passive cooling as used in some thermocycling devices. In some reaction vessels, such as the configuration in FIG. 30A, edge-looking windows are narrow (about 1.0 mm×4.5 mm) and the small size makes traditional lensing difficult. Collecting fluorescence from a major face of the reaction vessel, as in FIG. 30B, provides a larger detection window that allows for more signal to be collected while still allowing excitation and detection to be orthogonal to each other. In some embodiments, the optical detection chip is sized to match the reaction vessel dimensions. FIG. 30C illustrates detailed view of each of an exemplary excitation block and a detection block in accordance with some embodiments of the invention. As shown, excitation block 910 includes LED light sources 911 that direct light through filters and lenses 912 and then rod lenses 913 so as to emit the desired wavelengths of light to the desired locations of the reaction vessel 33. The optical detection block 920 includes photodiode detectors 921 that detect light emitted from the reaction vessel 33, the emitted light passing through rod lenses 923, and filters and lenses 922 before being received by the photodiode detectors 921 so as to ensure detection of particular wavelengths that may indicate a reaction that corresponds to presence of the target analyte within reaction vessel 33.

In some embodiments, the optical component 900 includes an optical excitation component 910 and an optical detection component 920 positioned on an optical mount adapted to receive a planar reaction vessel 33. The optical excitation component 910 is positioned to emit excitation energy through an edge (minor face) of a planar surface of the reaction vessel 33 and the optical detection component 920 is positioned along a major planar surface of the reaction vessel. In one aspect, the optical excitation and optical detection components are orthogonal relative each other. In some embodiments, the optical components are configured to utilize lenses with a high numerical aperture. In some embodiments, the optical components are configured for operation at low numerical apertures without requiring use of lenses. In such embodiments, the light path may travel from the source, through a filter and to the detection component without requiring use of lenses to focus the light produced by excitation. Such embodiments can be configured such that the excitation and detect light paths are spatially arranged relative each other to improve detection of light produced by excitation at low numerical apertures without requiring use of lenses. Such use of spatial discrimination in detecting of excited light allows for light detection without lenses, which allows for a system of reduced size.

In fluorescent detection systems, the excitation light typically exceeds the amount of the emitted fluorescent light signal. In order to efficiently detect the emitted signal it is important to collect as much emitted light as possible. Thus, most conventional systems employ a high numerical aperture in their optical detection systems. A high numerical aperture allows for collection of more light, which in turn provides for greater resolution, while a low numerical aperture typically results in the collection of less light resulting in a lower resolution. Most conventional fluorescent optical detection systems use a configuration involving a lens and a band pass filter in the light path between the light source and the detector. The filter is typically placed between the lens and the detector such that the lens provides for collimated light passing through the filter. In the absence of a lens (and collimated light) the filter becomes much less efficient as light of high incident angles striking the band pass filter merely passes through unfiltered. The lens obviates this problem as it collimates (reducing the high incident angle beams) resulting in more efficient filtering of the excitation wavelengths.

In some embodiments of the present invention, the optical system does not include a lens. In the absence of a lens, a low numerical aperture configuration is used with the light path consisting of just the light source, a band pass filter and the detector. Using a low numerical aperture with this configuration reduces the high incident light angles (without using a lens) thus improving the efficiency of the filtering which in turn results in a strong signal of emitted light with most of the excitation wavelengths filtered out.

In some embodiments, the optics module includes UV, blue, green, yellow and red LEDs, relevant optical filters, coupling optical elements and protective glass. In some embodiments, the optics device is fully encapsulated in epoxy, which provides protection from shock and protects against dust and moisture incursion. In some embodiments, the optics excitation and detection chips are of reduced size, such as less than 10 mm in each dimension, typically about 5 mm (l)×4 mm (w)×3 mm (h).

Figure 31:
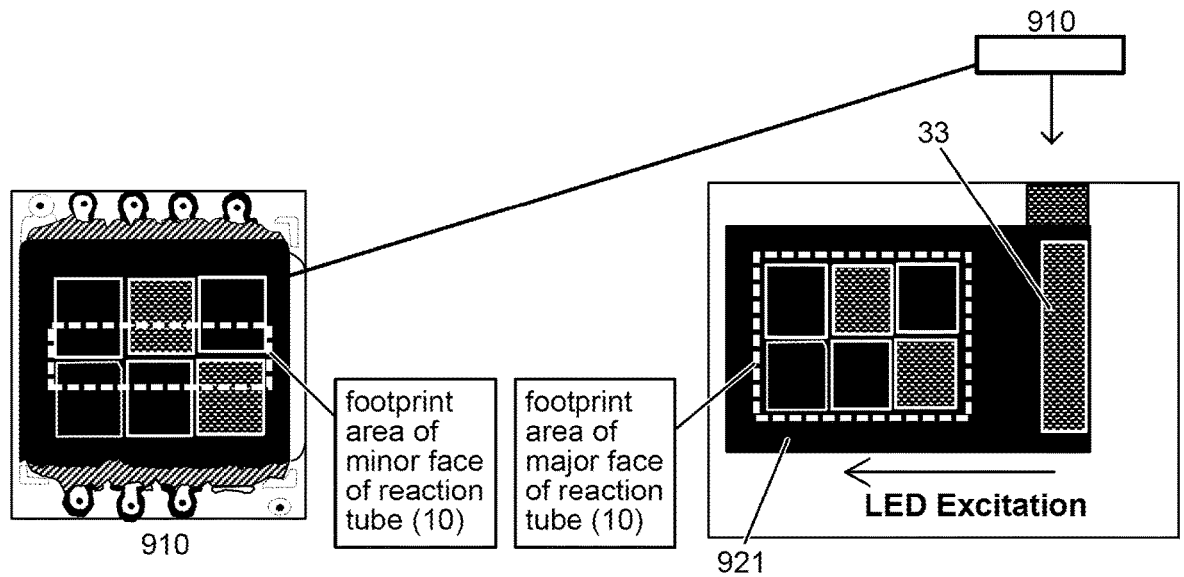
FIG. 31 illustrates exemplary detailed views of the excitation block 310 and the detection block 320 in accordance with some embodiments of the invention.

FIG. 31 illustrates detailed views of the excitation block 910 and the detection block 920 with an indication of the relative area of the adjacent reaction vessel through which light is emitted from the excite block and collected by the detect block.

Figure 32:
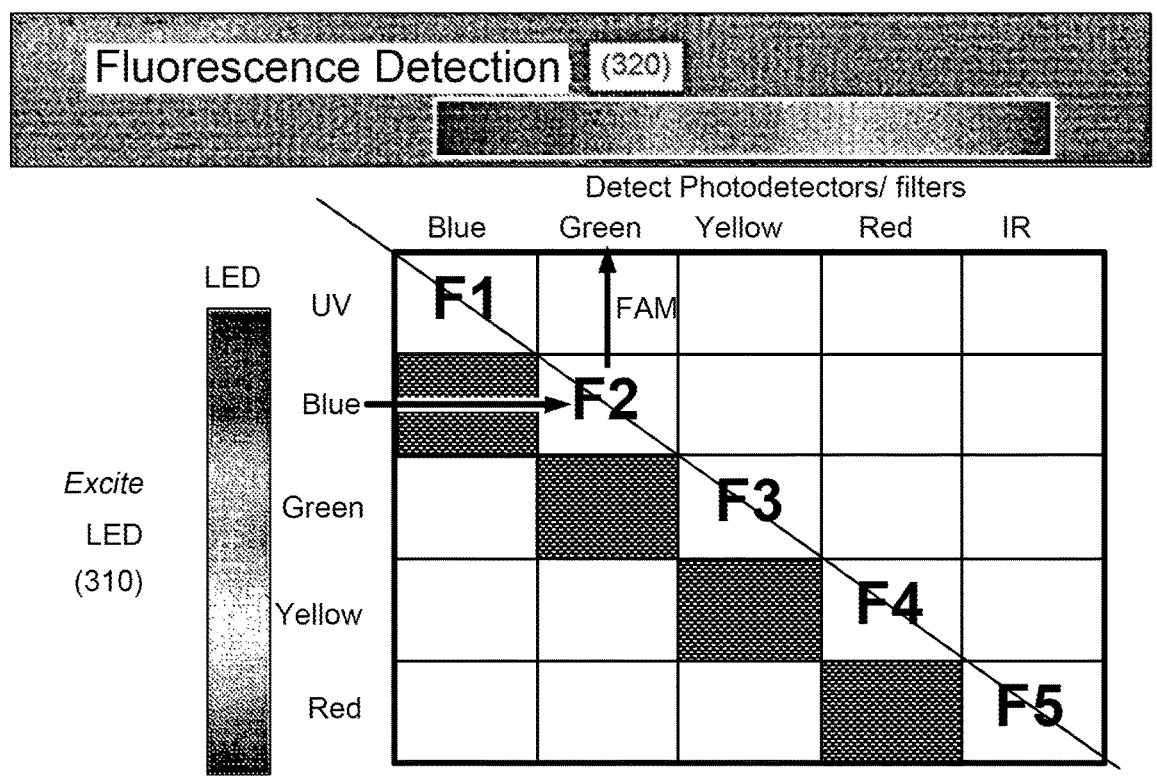
FIG. 32 illustrates fluorescence detection with the excitation and detection components of an exemplary optical component in accordance with some embodiments of the invention.

FIG. 32 illustrates fluorescence detection with the excitation and detection components of the optical component in accordance with some embodiments of the invention. As can be seen, the configuration in FIG. 32 matches the arrangement pattern for the excitation and detection blocks which relates to the use of the low numerical aperture, in accordance with some embodiments.

VIII. C. Thermal Control Device

VIII. C. 1. Overview

Figure 27:
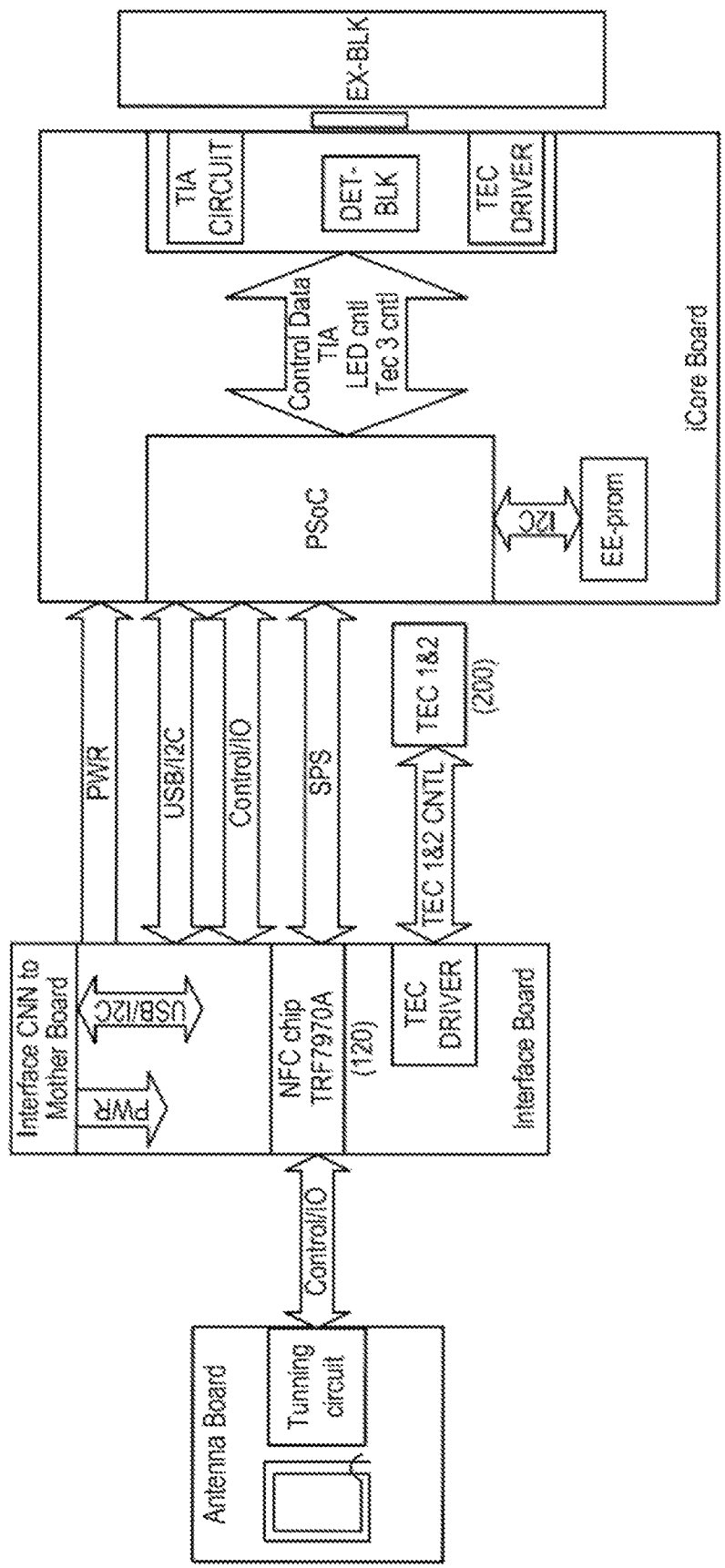
FIG. 27 illustrates an exemplary block control diagram of components of the TOS in accordance with some embodiments of the invention.

FIG. 27 illustrates a block control diagram of a thermal control device 800 in a TOS board in accordance with some embodiments of the invention. In some embodiments, the thermal control device includes dual thermoelectric coolers (TEC) with a thermal capacitor disposed there between. In some embodiments, the thermal control device employs closed loop control utilizing two thermistors to control operation of each TEC so as to optimize heating and cooling of the active surface engaged with the reaction vessel or vessel. This configuration provides lower noise, improved temperature stability, high gain and high band-width, as compared to conventional temperature control device controls. In some embodiments, one thermal control device is used to heat/cool a fluid sample through a major face of a reaction vessel. In some embodiments, a fluid sample is heated/cooled through both major faces of a reaction vessel, using a thermal control device with each major face of the reaction vessel.

In any of the embodiments described which include first and second thermoelectric coolers, the second thermoelectric cooler can be replaced with a thermal manipulation device. Such thermal manipulation device includes any of a heater (e.g., a thermoresistive heater), a cooler or any means suitable for adjusting a temperature. In some embodiments, the thermal manipulation device is included in a microenvironment common to the first thermoelectric cooler such that operation of the thermal manipulation device changes the temperature of the microenvironment relative an ambient temperature. In this aspect, the device changes the ambient environment to allow the first thermoelectric cooler to cycle between a first temperature (e.g. an amplification temperature between 60-70° C.) and a second higher temperature (e.g. a denaturation temperature of about 95° C.), cycling between these temperatures as rapidly as possible. If both the first and second temperatures are above the true ambient temperature, it is more efficient for a second heat source (e.g. thermoelectric cooler or heater) within a microenvironment to raise the temperature within the microenvironment above the ambient temperature. Alternatively, if the ambient temperature exceeds the second, higher temperature, the thermal manipulation device could cool the microenvironment to an ideal temperature to allow rapid cycling between the first and second temperatures more effectively.

In some embodiments, the thermal control device includes a first thermoelectric cooler having an active face and a reference face, a thermal manipulation device, and a controller operatively coupled to each of the first thermoelectric cooler and the thermal manipulation device. The controller can be configured to operate the first thermoelectric cooler in coordination with the thermal manipulation device so as to increase efficiency of the first thermoelectric cooler as a temperature of the active face of the first thermoelectric cooler changes from an initial temperature to a desired target temperature. The thermal manipulation devices can include a thermo-resistive heating element or a second thermoelectric cooler or any suitable means for adjusting temperature.

In some embodiments, the thermal control device further includes one or more temperature sensors coupled with the controller and disposed along or near the first thermoelectric cooler, the thermal manipulation device and/or a microenvironment common to the first thermoelectric cooler and the thermal manipulation device. The thermal manipulation device can be thermally coupled with the first thermoelectric cooler through a microenvironment defined within a diagnostic assay system in which the thermal manipulation device is disposed such that a temperature of the microenvironment can be controlled and adjusted from an ambient temperature outside of the system.

In some embodiments, the thermal control device includes a controller coupled with each of the thermoelectric cooler and the thermal manipulation device that is configured to control temperature so as to control a temperature within a chamber of a reaction vessel in thermal communication with the thermal control device. In some embodiments, the controller is configured to operate the first thermoelectric cooler based on thermal modeling of an in situ reaction chamber temperature within the reaction vessel. The thermal modeling can be performed in real-time and can utilize Kalman filtering depending on the accuracy of the model.

In some embodiments, the thermal control device is disposed within an device diagnostic assay system and positioned to be in thermal communication with a reaction vessel of an assay cartridge disposed within the system. The controller can be configured to perform thermal cycling in a polymerase chain reaction process within a chamber of the reaction vessel.

In some embodiments, the thermal control device includes a first thermoelectric cooler having an active face and a reference face, a thermal manipulation device, a thermal interposer disposed between the first thermoelectric coolers and the thermal manipulation device such that the reference face of the first thermoelectric cooler is thermally coupled with the thermal manipulation device through the thermal interposer (which can be a thermal capacitor as disclosed herein), and a first temperature sensor adapted to sense the temperature of the active face of the first thermoelectric cooler. The device can further include a controller operatively coupled to each of the first thermoelectric cooler and the thermal manipulation device. The controller can be configured to operate the thermal manipulation device in coordination with the first thermoelectric cooler to increase speed and efficiency of the first thermoelectric cooler as a temperature of the active face of the first thermoelectric cooler is changed from an initial temperature to a desired target temperature. In some embodiments, the controller is configured with a closed control loop having a feedback input of a predicted temperature based on a thermal model that includes an input from the first temperature sensor.

Various aspects of such a thermal control device are described in detail in concurrently filed, U.S. Non-Provisional application Ser. No. 15/217,902, entitled, "Thermal Control Device and Methods of Use," filed on Jul. 22, 2016, the entire contents of which are incorporated herein by reference for all purposes. It is appreciated that a thermal control device used in a TOS system in accordance with some embodiments of the invention can include any combination of elements as described therein.

VIII. C. 2. TEC Design

In some embodiments, the thermal control device includes a first TEC having an active face and a reference face; a second TEC having an active face and a reference face; and a thermal interposer disposed between the first and second TECs such that the reference face of the first TEC is thermally coupled with the active face of the second TEC through the thermal interposer. In some embodiments, the thermal interposer acts as a thermal capacitor. In some embodiments, the thermal control device includes a controller operatively coupled to each of the first and second TECs, the controller configured to operate the second TEC concurrent with the first TEC so as to increase the speed and efficiency in operation of the first TEC as a temperature of the active face of the first TEC changes from an initial temperature to a desired target temperature. In some embodiments, the first and second thermoelectric coolers are thermally coupled through a thermal capacitor with sufficient thermal conductivity and mass to transfer and store thermal energy so as to reduce time when switching between heating and cooling, thereby providing faster and more efficient thermal cycling. In some embodiments, the device utilizes a thermocouple within the first thermoelectric cooler device and another thermocouple within the thermal capacitor layer and operates using first and second closed control loops based on the temperature of the first and second thermocouple, respectively. In order to utilize the stored thermal energy in the thermal capacitor layer, the second control loop may be configured to lead or lag the first control loop. By using one or more of these aspects described herein, embodiments of the present invention provide a faster, more robust thermal control device for performing rapid thermal cycling, preferably in about two hours or less, even in problematic high temperature environments described above.

In some embodiments, the thermal control device includes a thermal capacitor formed of a thermally conductive material of sufficient mass to store thermal energy sufficiently to facilitate increased speed in switching between thermal cycles and efficiency in heating and cooling of a TEC. In some embodiments, the thermal capacitor includes a material having higher thermal mass than that of the active and reference faces of the first and second TECs, which can be formed of a ceramic material. In some embodiments, the thermal capacitor is formed of a layer of copper with a thickness of about 10 mm or less, (e.g., about 10, 9, 8, 7, 6, 5, 4, 3, 2, or 1 mm, or less). This configuration allows for a thermal control device of a relatively thin, planar construction so as to be suitable for use with a reaction vessel in a nucleic acid analysis device of reduced size.

In some embodiments, the thermal control device includes a first temperature sensor adapted to sense the temperature of the active face of the first TEC; and a second temperature sensor adapted to sense a temperature of the thermal capacitor. In some embodiments, the first and second temperature sensors are coupled with the controller such that operation of the first and second TECs is based, at least in part, on an input from the first and second temperature sensors to the controller, respectively. In some embodiments, the second temperature sensor is embedded or at least in thermal contact with the thermally conductive material of the thermal capacitor. It is appreciated that in any of the embodiments described herein the temperature sensor may be disposed in various other locations so long as the sensor is in thermal contact with the respective layer sufficiently to sense temperature of the layer.

In some embodiments, the thermal control device includes a controller configured with a primary control loop into which the input of the first temperature sensor is provided, and a secondary control loop into which the input of the second temperature sensor is provided. The controller can be configured such that a bandwidth response of the primary control loop is timed faster (or slower) than a bandwidth response of the secondary control loop. Typically, both the primary and secondary control loops are closed-loop. In some embodiments, the controller is configured to cycle between a heating cycle in which the active face of the first TEC is heated to an elevated target temperature and a cooling cycle in which the active face of the first TEC is cooled to a reduced target temperature. The controller can be configured such that the secondary control loop switches the second TEC between heating and cooling modes before the first control loop is switched between heating and cooling so as to thermally load the thermal capacitor. In some embodiments, the secondary control loop maintains a temperature of the thermal capacitor within about 40° C. from the temperature of the active face of the first TEC. In some embodiments, the secondary control loop maintains a temperature of the thermal capacitor within about 5, 10, 15, 20, 25, 30, 35, 40, 45, or 50 degrees C. from the temperature of the active face of the first TEC. The controller can be configured such that efficiency of the first TEC is maintained by operation of the second TEC such that heating and cooling with the active face of the first TEC occurs at a ramp rate of about 10° C. per second. Non-limiting exemplary ramp rates that can be achieved with the instant invention include 20, 19, 18, 17, 16, 15, 14, 13, 12, 11, 10, 9, 8, 7, 6, 5, 4, 3, 2, or 1° C. per second. In some embodiments, the elevated target temperature is about 90° C. or greater and the reduced target temperature is about 40° C. or less. In some embodiments, the elevated temperature is about 95° C. and the reduced target temperature is in a range from about 60° C. to about 75° C., including all temperatures in between the ends of the range.

In some embodiments, the thermal control device further includes a heat sink coupled with the reference face of the second TEC to prevent thermal runaway during cycling. The thermal control device may be constructed in a generally planar configuration and dimensioned to correspond to a planar reaction chamber portion of a reaction vessel of an assay cartridge. In some embodiments, the planar size has a length of about 45 mm or less and a width of about 20 mm or less, or a length of about 40 mm by about 12.5 mm, such as about 11 mm by 13 mm, so as to be suitable for use with a reaction vessel in a miniature PCR analysis device. The generally planar configuration can be configured and dimensioned to have a thickness from an active face of the first TEC to an opposite facing side of the heat sink of about 20 mm or less. Advantageously, in some embodiments, the thermal control device can be adapted to engage with a reaction vessel for thermal cycling of the reaction vessel on a single side thereof to allow optical detection of a target analyte from an opposing side of the reaction vessel during thermal cycling.

In some embodiments, methods of controlling temperature are provided herein. Such methods include steps of: operating a first TEC having an active face and a reference face to heat and/or cool the active face from an initial temperature to a target temperature; and operating a second TEC having an active face and a reference face so as to increase efficiency of the first TEC as the temperature of the active face of the first TEC changes from the initial temperature to the desired target temperature, the active face of the second TEC being thermally coupled to the reference face of the first TEC through a thermal capacitor. Such methods can further include steps of: operating the first TEC comprises operating a primary control loop having a temperature input from a temperature sensor at the active face of the first TEC, and operating the second TEC comprises operating a secondary control loop having a temperature input from a temperature sensor within the thermal capacitor. In some embodiments, the method further includes:

cycling between a heating mode in which the active face of the first thermoelectric device heats to an elevated target temperature and a cooling mode in which the active face is cooled to a reduced target temperature; and storing thermal energy from thermal fluctuations between the heating and cooling modes in the thermal capacitor, the thermal capacitor comprising a layer having increased thermal conductivity as compared to the active and reference faces of the first and second thermoelectric cooling devices, respectively.

In some embodiments, methods of controlling temperature in thermal cycling include: cycling between a heating mode and a cooling mode of the second thermoelectric device concurrent with cycling between the heating and cooling modes of the first thermoelectric device thereby maintaining efficiency of the first thermoelectric device during cycling. In some embodiments, the controller is configured such that a bandwidth response of the primary control loop is faster than a bandwidth response of the secondary control loop. The controller can further be configured such that cycling is timed by the controller to switch the second thermoelectric device between modes before switching of the first thermoelectric device between modes so as to thermally load the thermal capacitor. In some embodiments, the elevated target temperature is about 95° C. or greater and the reduced target temperature is about 50° C. or less. In some embodiments, methods of controlling temperature further include: maintaining a temperature of the thermal capacitor within about 40° C. from the temperature of the active face of the first TEC by controlled operation of the second TEC during cycling of the first TEC so as to maintain an efficiency of the first TEC during cycling. In some embodiments, the efficiency of the first TEC is maintained by operation of the second TEC such that heating and/or cooling with the active face of the first TEC occurs at a ramp rate of within 10° C. per second or less. Such methods may further include: operating a heat sink coupled with the reference face of the second TEC during cycling with the first and second TECs so as to prevent thermal runaway.

In some embodiments, methods of thermal cycling in a polymerase chain reaction process are provided herein. Such methods may include steps of: engaging a thermal control device with a reaction vessel having a fluid sample therein for performing a polymerase chain reaction for amplifying a target polynucleotide such that the active face of the first TEC thermally engages the reaction vessel; and thermal cycling the thermal control device according to a particular protocol for amplifying the target polynucleotide contained in the fluid sample. In some embodiments, engaging the thermal control device with the reaction vessel comprises engaging the active face of the first TEC against one side of the reaction vessel such that an opposite side remains uncovered by the thermal device to allow optical detection from the opposite side. In some embodiments, each of the heating mode and cooling mode use one or more operative parameters, wherein the one or more operative parameters are asymmetric between the heating and cooling mode. For example, each of the heating mode and cooling mode has a bandwidth and a loop gain, wherein the band width and the loop gains of the heating mode and cooling mode are different.

In some embodiments, methods of controlling temperature with a thermal control device are provided. Such methods include steps of: providing a thermal control device a first and second TEC with a thermal capacitor there between, wherein each of the first and second TECs have an active face and a reference face; heating the active face; cooling the active face; heating the reference face; and cooling the reference face. In some embodiments, each of heating the active face and cooling the active face is controlled by one or more operative parameters. In some embodiments, a magnitude of the one or more operative parameters is different during heating the active face as compared to cooling the active face.

In some embodiments, methods include reliability testing between multiple thermal control devices by use of an alternating fixture. Such methods include steps of: alternating thermal cycling among the thermal control device and a second or more thermal control devices, to effect thermal cycling of a second or more reaction vessels by operating a fixture that alternatingly positions the thermal control device and the second or more thermal control devices at an active location at which thermal cycling of the respective reaction vessel is performed. In some embodiments, the fixture is a rotatable hub with the thermal control device and the two or more thermal control devices distributed circumferentially about an outside of the hub such that operating the fixture comprises rotating the hub.

VIII. C. 2. a. Example TEC Design Configurations

Figure 33A:
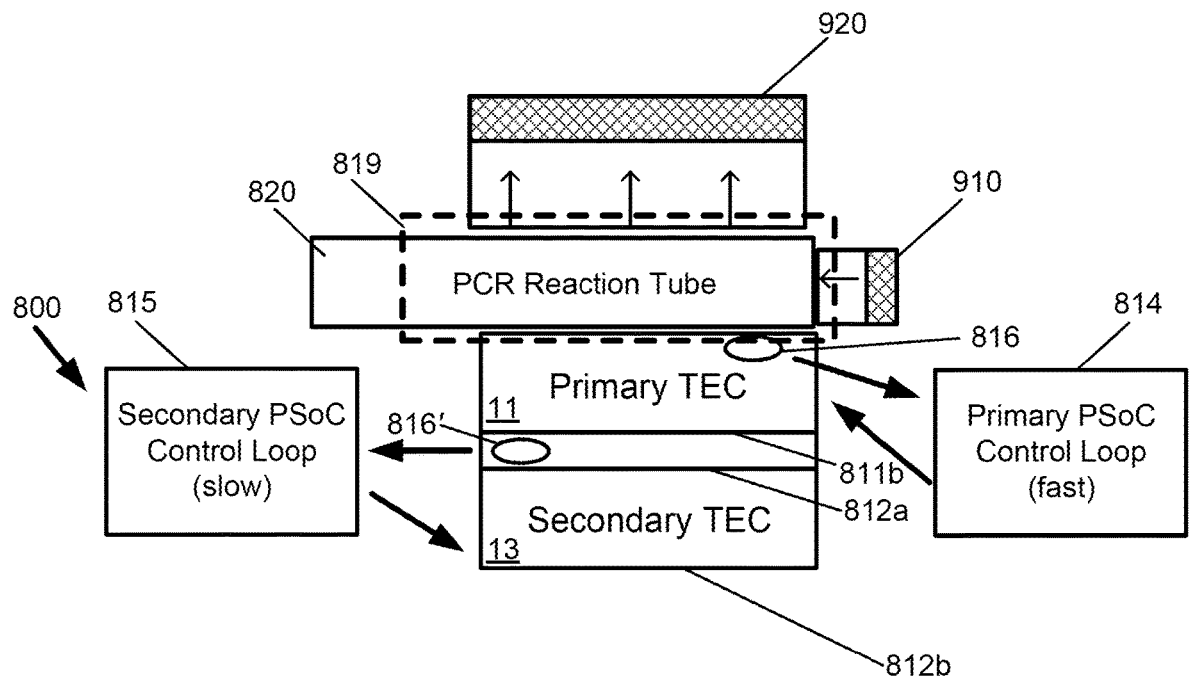
FIG. 33A illustrates a schematic of a thermal control device in accordance with some embodiments of the invention.
Figure 33B:
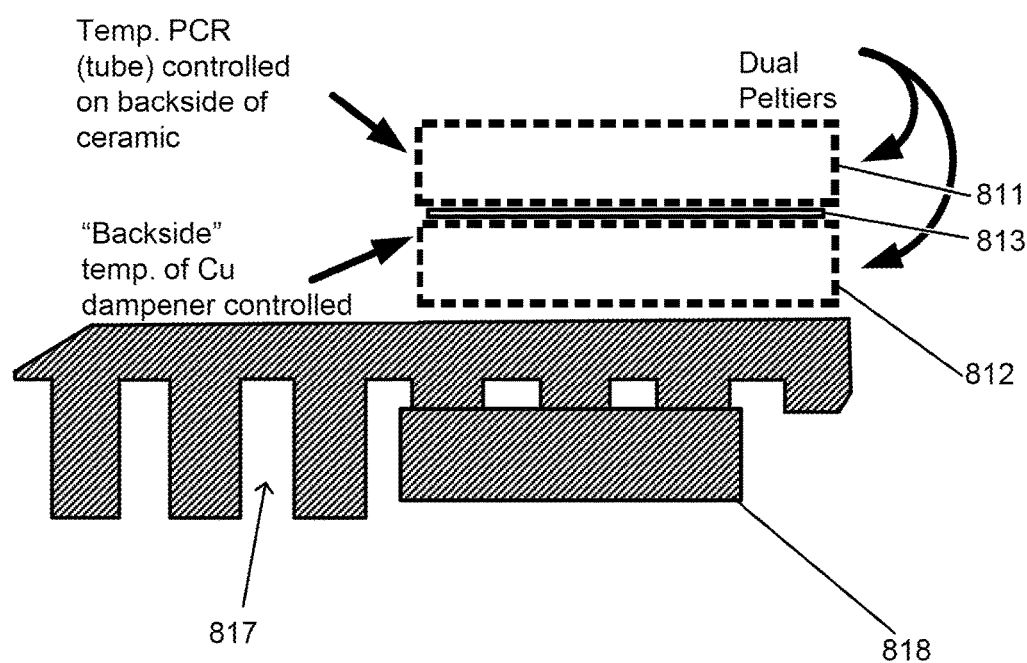
FIGS. 33B-C illustrates models of an exemplary thermal control device in accordance with some embodiments of the invention.

FIG. 33A shows an exemplary thermal control device that includes a first TEC 811 (primary TEC) and a second thermal manipulation device, such as secondary TEC 812 or thermo-resistive element) thermally coupled through a thermal capacitor 813, also referred to as a thermal interposer. The TECs are configured such that an active face 811*a* of the first TEC 811 is thermally coupled with a reaction vessel 33 to facilitate controlling thermal cycling therein. The device can optionally include a coupling fixture 819 for mounting the device on the tube. In some embodiments, the device can be secured to a fixture that positions the device adjacent the tube. The opposing reference face 811*b* of the first TEC is thermally coupled with an active face 812*a* of the second TEC 812 through the thermal capacitor layer. This configuration may also be described as the reference face 811*b* being in direct thermal contact with one side of the thermal capacitor layer 813 and the active face 812*a* being in direct thermal contact with the opposite side of the thermal capacitor layer 813. In some embodiments, the reference face 812*b* of the second TEC is thermally coupled with a heat sink 817 and/or a cooling fan 818, such as shown in the embodiment of FIG. 33B. In this embodiment, the thermal control device 800 is configured such that it is thermally coupled along one side of a planar portion of the reaction vessel 33 so as to allow optical excitation from another direction (e.g. a side of the tube) with an optical excitation means 910, such as a laser, and optical detection from another direction (e.g. an opposite side of the tube) with an optical detection means 920.

A thermocouple 816 is included in the first TEC 811 at or near the active face 811*a* to allow precise control of the temperature of the reaction vessel. The temperature output of this thermocouple is used in a primary control loop 814 that controls heating and cooling with active face 11*a*. A second thermocouple 816' is included within or near the thermal capacitor layer and an associated temperature output is used in a second control loop 814' that control heating and cooling with the active face 812*a* of the second TEC. In one aspect, the first control loop is faster than the second control loop (e.g. the second control loop lags the first), which accounts for thermal energy transferred and stored within the thermal capacitor layer. By use of the these two control loops, the temperature differential between the active face

811a and the reference face 811b of the first TEC 811 can be controlled so as to optimize and improve efficiency of the first TEC, which allows for faster and more consistent heating and cooling with the first TEC, while the thermal capacitor allows for more rapid switching between heating and cooling, as described herein and demonstrated in the experimental results presented below.

Instead of bonding a standard heat-sink to the ceramic plate opposite the reaction vessel, another (secondary) TEC is used to maintain a temperature within about 40° C. of the active face of the primary TEC. In some embodiments, two PID (Proportional Integral Derivative gain) control loops are used to maintain this operation. In some embodiments, non-PID control loops are used to maintain the temperature of the active face of the primary TEC. Typically, a fast PID control loop drives the primary TEC to a predetermined temperature setpoint, monitored by a thermistor mounted to the underside of the ceramic plate in contact with the reaction vessel. This loop operates with maximum speed to ensure the control temperature can be quickly and accurately reached. In some embodiments, a second, slower PID control loop maintains the temperature for the bottom face of the primary TEC to maximize thermal efficiency (experimentally determined to be within ~40° C. from the active face temperature). As discussed above, non-PID control loops can also be used to maintain the temperature of the TEC to maximize thermal efficiency. In some embodiments, it is advantageous to dampen the interaction between the two control loops to eliminate one loop from controlling the other. It is further advantageous to absorb and store thermal energy from the first and/or second TEC by use of the thermal capacitor layer to facilitate rapid switching between heating and cooling.

Two non-limiting exemplary ways to achieve rapid and efficient switching between heating and cooling as used in some embodiments of the invention are detailed herein. First, the bandwidth response for the secondary control loop is intentionally limited to be much lower than the fast primary loop, a so-called "lazy loop." Second, a thermal capacitor is sandwiched between two TECs. While it is desirable for the entire thermal control device to be relatively thin to allow use of the device on a reaction chamber portion of a reaction vessel, it is appreciated that the thermal capacitor layer may be thicker so long as it provides sufficient mass and conductivity to function as a thermal capacitor for the TECs on either side. In some embodiments, the thermal capacitor layer is a thin copper plate of about 1 mm thickness or less. Copper is advantageous because of its extremely high thermal conductivity, while 1 mm thickness is experimentally determined to sufficiently dampen the two TECs while providing sufficient mass for the thin layer to store thermal energy so as to act as a thermal capacitor. While copper is particularly useful due to its thermal conductivity and high mass, it is appreciated that various other metals or materials having similar thermal conductivity properties and high mass can be used, preferably materials that are thermally conductive (even if less than either TEC) and with a mass the same or higher than either TEC to allow the layer to operate as a thermal capacitor in storing thermal energy. In another aspect, the thermal capacitor layer may contain a second thermistor which is used to monitor the "backside" temperature (e.g. reference face) used by the secondary PID control loop. Both control loops can be digitally implemented within a single PSoC (Programmable System on Chip) chip which sends control signals to two bipolar Peltier current supplies. It will be appreciated by the skilled artisan that in some embodiments, non-PSOC chips can be used for control, e.g., field programmable gate arrays (FPGAs) and the like are suitable for use with the instant invention. In some embodiments, the dual-TEC module includes a heat-sink to prevent thermal runaway, which can be bonded to the backside of the secondary TEC using, e.g., thermally-conductive silver epoxy. Alternative bonding methods and materials suitable for use with the invention are well known to persons of skill in the art.

FIG. 33B shows a schematic of dual-TEC design. Temperature of the PCR reaction vessel (measured by a thermistor, (16) (ellipse) is governed by the primary TEC and controlled by a loop in PSoC firmware. Optimal thermal efficiency of the Primary TEC is maintained by a second thermistor (816') (ellipse) in thermal contact with a copper layer, which feeds into a secondary PSoC loop, controlling a second TEC.

VIII. C. 2. b. Initial Dual-TEC Fabrication

Figure 33C:
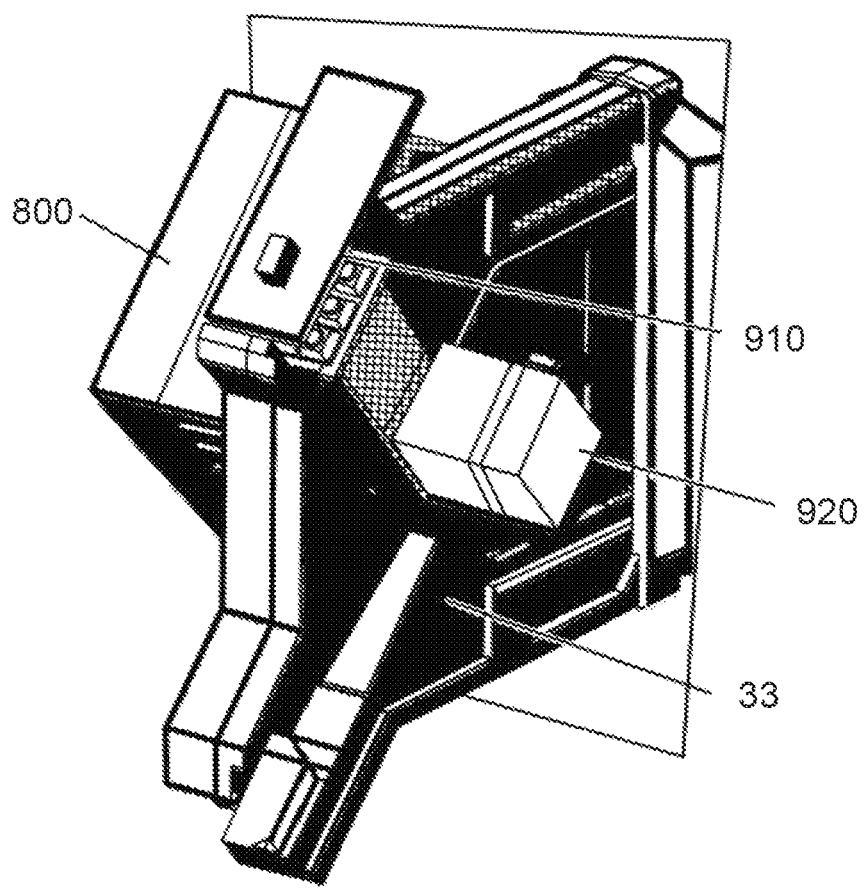

FIG. 33C shows an example dual-TEC heating/cooling module with a thermal control device 800 thermally engaged against one major face of the reaction vessel, an optical excite block adjacent a minor face (e.g. edge) of the reaction vessel, and an optical detect block 920 against an opposing major face of the reaction vessel 33. In some embodiments, both Primary and Secondary TECs (Laird, OptoTEC HOT20,65,F2A,1312, datasheet below) measure 13 (w)×13 (l)×2.2 (t) mm, and have a maximum thermal efficiency=60%. In some embodiments, the planar area affected by the TEC module is matched to the GX reaction vessel. In some embodiments, it is configured to accommodate reaction vessels ranging from 25 μl to 100 μl.

FIG. 33B shows an exemplary dual-TEC module for single-sided heating and cooling of a reaction vessel in a chemical analysis system. It is appreciated that this design could be modified to provide the dual-TEC on both sides for double-sided heating in some embodiments. As can be seen, the heat-sink includes a mini-fan to flush heat and maintain TEC efficiency. The primary TEC (top) cycles temperature in the reaction vessel, monitored by a thermistor mounted to the under-side of the ceramic in contact with the tube. The "backside" TEC maintains the temperature of an interstitial copper layer (by use of a thermistor) to ensure optimal thermal efficiency of the primary TEC. A heat-sink with integrated mini-fan keeps entire module at thermal equilibrium.

In some embodiments, a small thermistor with +/−0.1° C. temperature tolerance is bonded to the underside of top face of the primary TEC using silver epoxy. This thermistor probes the temperature applied to the reaction vessel and is an input for the primary control loop in the PSoC, which controls the drive current to the primary TEC. The bottom surface of the primary TEC is bonded to a 1 mm-thick copper plate with silver epoxy. The copper plate has a slot containing a second TR136-170 thermistor, potted with silver epoxy to monitor "backside temperature," the signal input for the secondary control loop in the PSoC. The secondary TEC, controlled by the secondary control loop, is then sandwiched between the copper plate and an aluminum heat-sink. The heat-sink is machined to an overall thickness=6.5 mm, keeping the entire package <13 mm thick, and a planar size=40.0(l)×12.5(w) mm, necessitated by space constraints within an instrument of reduced size. A 12×12 mm Sunon Mighty Mini Fan (datasheet below) is glued within an inset machined into the heat-sink where the TECs interact with the heat-sink. Note the mini-fan does not need to directly cool the heat-sink; a quiet, durable, cheap, low-voltage (3.3V max) brushless motor is sufficient to maintain heat-sink performance by removing hot surface air from the aluminum/air interface using shear flow, as opposed to direct air cooling (as in some conventional analysis devices).

Testing of prototype units can be used to determine whether heating/cooling speed, thermal stability, robustness with increased ambient temperature, and overall system reliability is sufficient to meet engineering requirement specifications. Thermal performance has been shown acceptable such that the design goals are met for an exemplary reduced size system: smaller size, robust, and inexpensive (fewer parts needed than with two-sided heating/cooling). Further, single-sided heating/cooling enables more efficient optical detection through the side of the reaction vessel.

FIG. 33C shows a CAD drawing of the dual-TEC heating/cooling module, as well as the LED Excite- and Detect-Blocks, and the reaction vessel within an exemplary system. The reaction vessel is thermal-cycled on one side (first major face of the reaction vessel) and fluorescence detected through the opposite side (second major face of the reaction vessel). LED illumination remains through the edge (minor face) of the reaction vessel.

VIII. C. 2. c. Initial Heating/Cooling Performance

Heating and cooling performance of the exemplary TEC assembly was measured using a custom fixture that securely clamps the TEC assembly against one surface of a reaction vessel. Care was taken to thermally isolate the TEC assembly from the fixture by making it of thermally insulating Delrin. To mimic a thermal load of a PCR, the reaction vessel was filled with a fluid sample which was in secure contact with a fluorescent detect block on the tube surface opposite the TEC assembly. It should be noted the temperature on the top TEC surface contacting the tube in this geometry was independently measured to be equal or higher than the temperature measured on the primary TEC thermistor. Therefore, it is reasonable to use the read temperature of the primary TEC thermistor to initially characterize thermal performance of the dual-TEC heating/cooling system. Any mismatch between thermistor and reaction vessel temperature can be characterized and adjusted for using feedback loops between the primary TEC thermistor and the temperature of the fluid sample in the reaction vessel.

In some embodiments, a clamping fixture is used to secure the thermal control device to a reaction vessel for thermal characterization. In one example, a reaction vessel can be filled with a fluid sample and secured to make thermal contact between the heating/cooling module and one face of the reaction vessel. The other face of the tube can be clamped against a fluorescent detect block. An LED excite block illuminates the solution through the edge of the tube. In some embodiments both excitation and detection are done through minor faces of the tube.

In some embodiments, a PSoC control board employs PID control to maintain a temperature setpoint of the primary TEC thermistor and to provide dual-polarity drive current to the TEC devices (positive voltage when heating, negative voltage when cooling), and to power the mini-fan. This PID loop was tuned to maximize performance of the primary TEC. A script was written to cycle the set-point of the tube between high and low temperature extremes characteristic of PCR thermo-cycling. Specifically, the low temperature set-point=50° C., with a dwell time 12 sec, beginning once the measured temperature is within +/−0.1° C. for a 1 sec. Similarly, the high-temperature set-point=95° C. for 12 sec, beginning once the temperature is maintained +/−0.1° C. from the setpoint for 1 sec. The script cycled between 50° C. and 95° C. ad infinitum.

The secondary control loop was also maintained within the same PSoC chip, reading the temperature of the secondary thermistor in thermal contact with the copper dampening/thermal capacitor layer (see FIG. 33A) and acting upon the secondary TEC. A different set of PID tuning parameters was found to properly maintain system thermal performance by controlling the temperature of this copper layer, so-called the "backside" temperature. This control loop had a significantly lower bandwidth than the primary TEC control loop, as expected. The PSoC and associated program also allow multiple set-points of backside temperature, which is useful in maximizing ramp rate performance by keeping the primary TEC operating under optimally efficient thermal conditions.

Figure 34:
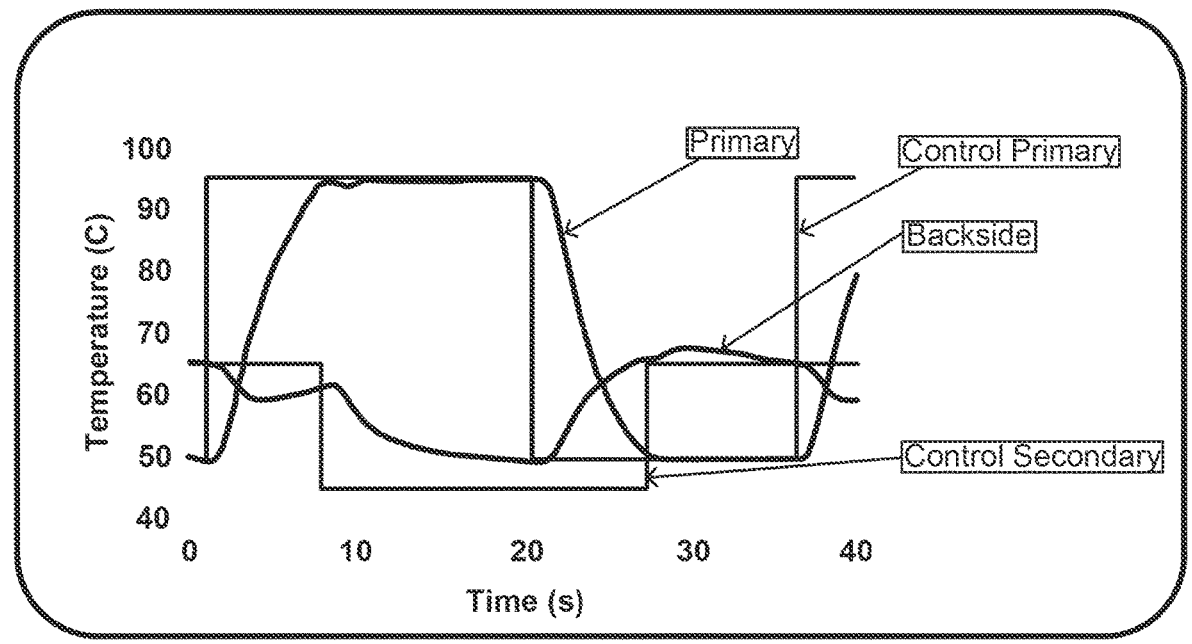
FIG. 34 shows a thermal cycle under closed loop control in accordance with some embodiments of the invention.
Figure 35:
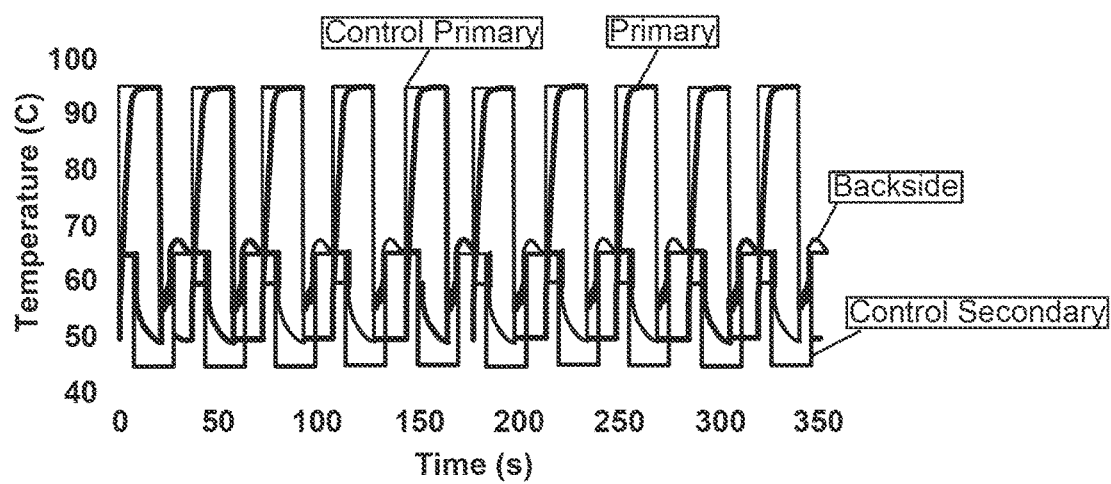
FIG. 35 shows ten successive thermal cycles over a full range of PCR thermo-cycling in accordance with some embodiments of the invention.

FIG. 34 shows an exemplary thermal cycle from a reaction vessel temperature, the traces measured for a thermal cycle from 50° C. →95° C. →50° C. (Primary trace) under closed-loop control. Closed-loop heating and cooling rates are −7° C./sec. The control primary is the desired temperature set-point of the thermal cycle (the square function between 0 seconds and 20 seconds elapsed time) and the primary trace is the measured temperature of the tube. As can be seen, the actual thermal cycle lags the desired thermal cycle indicated by the control primary function. It was determined that the thermal efficiency of the primary TEC was highest with a temperature differential between the tube and the backside of no higher than 30° C., so the backside temperature was controlled to be 65° C. when heating to maximum temperature (tube 95° C.) and 45° C. when cooling the tube to 50° C. (backside trace). Once the primary TEC has ramped to higher temperature, the backside temperature could be slowly and controllably driven to a lower temperature in anticipation of the next thermal cycle shown starting at about 37 seconds elapsed time). This scheme is analogous to using the backside TEC to properly load a "thermal spring" acting upon the primary TEC, and is applicable for use with PCR systems, because the thermal profile to be applied for a particular PCR assay is known a priori by an assay designer. Note the closed-loop ramp rate for stable and repeatable heating and cooling is 6.5 seconds for the 45° C. range, as shown for ten successive thermal cycles, as shown in FIG. 35, corresponding to a true closed loop ramp rate −7° C./sec for both heating and cooling. Performance is maintained throughout multiple cycles over the full PCR thermo-cycling range.

VIII. C. 2. d. Early and Near-term Reliability Experiments

A typical PCR assay has about 40 thermal cycles from the anneal temperature (~65° C.) to the DNA denaturation temperature (~95° C.) and back to the anneal temperature. For assessing reliability, an exemplary thermal control module was cycled between 50° C. (on the order of the minimum temperatures used for PCR experiments) and 95° C., with a 10 sec wait time at each temperature to enable system thermal equilibrium.

Figure 36A:
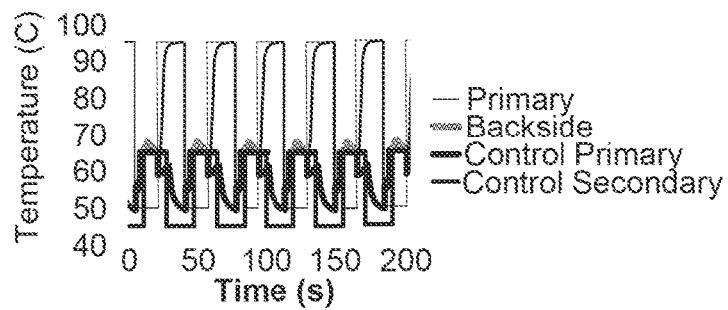
FIG. 36A shows thermo-cycling performance for five cycles at the beginning of thermal cycling and after two days of continuous thermal cycling.
Figure 36A:
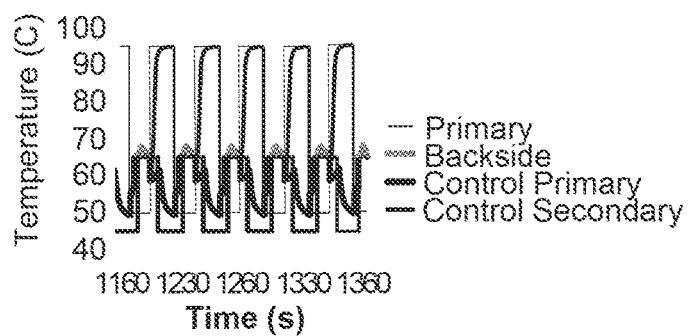
Figure 36B:
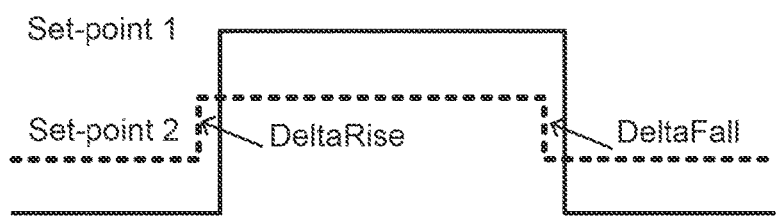
FIG. 36B shows a control diagram of set points used in control loops in accordance with some embodiments of the invention

FIG. 36A shows a comparison of the first and final 5 cycles of a 5,000 cycle test. Note the time axis of the trace on the right is from a small data-sampling range; 5,000 cycles took approximately 2 days. This module has since been cycled over 10,000 times with maintained performance. As can be seen, thermo-cycling performance for cycles 1-5 (left) remains constant after 5,000 cycles (cycles 4,995-5,000 at right) and there is no change in the thermal performance between the initial and final cycles. This is encouraging for two reasons. First, closed-loop parameters for rapid heating/cooling are quite stable with repeated thermal cycling. Even small thermal instability leads to drift in measured temperature curves for both the primary and backside TECs, quickly escalating to thermal runaway (which would induce an over-current shutdown fault in the firmware). Properly-tuned systems did not display this behavior, demonstrating the robustness of the system. Second, the thermal efficiency of the module is stable over 5,000 cycles. Indeed, this unit has subsequently been cycled >10,000 times without catastrophic or gradual erosion of performance. FIG. 36B shows thermo-cycling performance for five cycles at the beginning of thermal cycling and after two days of continuous thermal cycling.

VIII. D. Thermal Modeling Approach for Controlling Thermal Cycling

In another aspect, the thermal control device can be configured to control temperature based on thermal modeling. This aspect can be used in thermal control device configured for one-sided heating or two-sided heating. In some embodiments, such devices include a first thermoelectric cooler and another thermal manipulation device, each being coupled to a controller that controls the first thermoelectric cooler in coordination with the thermal manipulation device to improve control, speed and efficiency in heating and/or cooling with the first thermoelectric cooler. It is appreciated, however, that this thermal modeling aspect can be incorporated into the controls of any of the configurations described herein.

Figure 37:
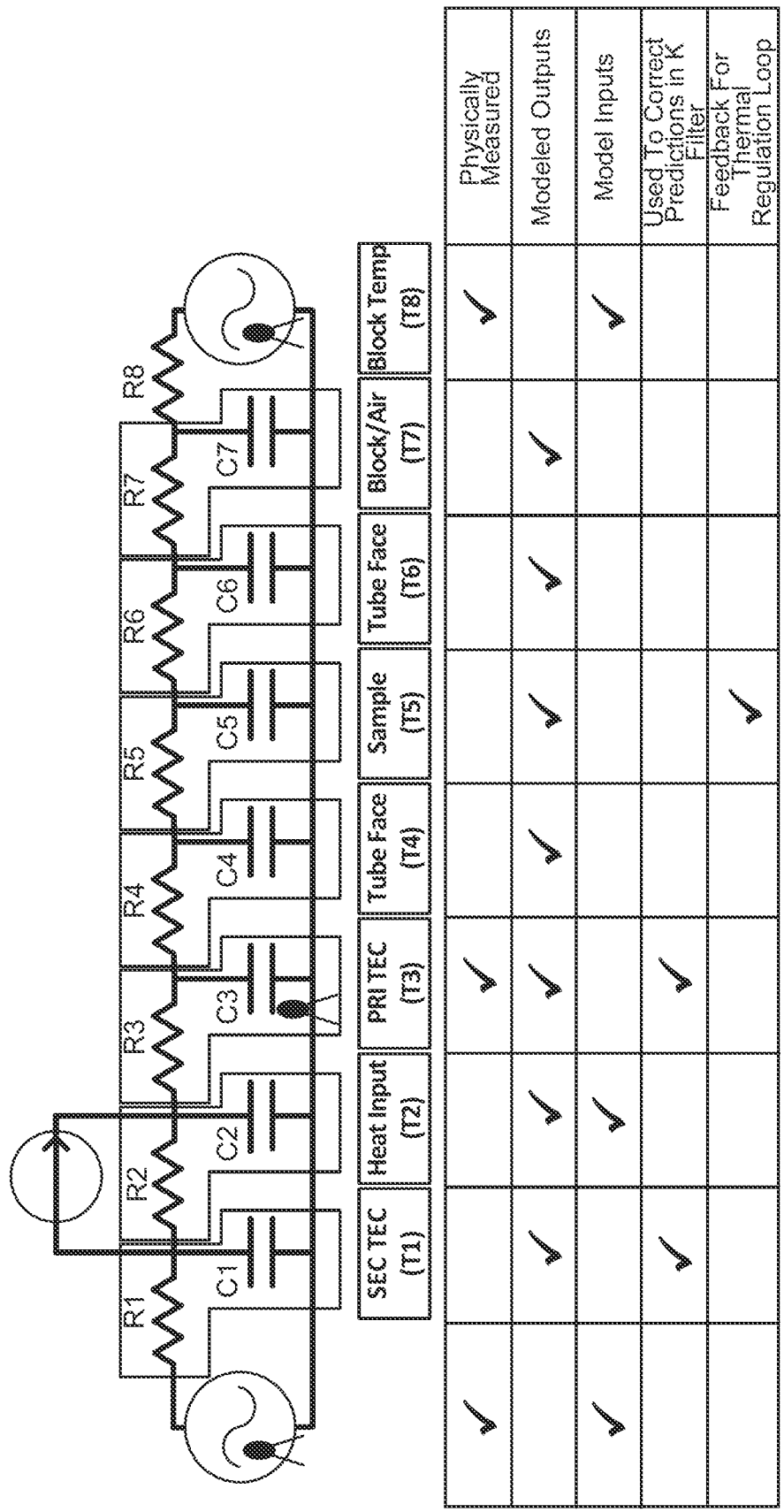
FIG. 37 shows a diagram of set points used in control loops in accordance with some embodiments of the invention.

An example of such an approach is illustrated in the state model diagram shown in FIG. 37. This figure illustrates a seven state model for use with a single-sided version of the thermal control device. This model applies electrical theories to model real world thermal system of the temperature that include the temperatures of the thermoelectric cooler faces, the reaction vessel or vessel, and the fluid sample within the reaction vessel. The diagram shows the seven states of the model and the three measured states used in the Kalman algorithm to arrive at an optimal estimation of the reaction vessel contents assuming it is water.

In the circuit model of FIG. 37, capacitors represent material thermal capacitance, resistors represent material thermal conductivity, voltage at each capacitor and source represents temperature, and the current source represents thermal power input from the front side thermoelectric cooler (TEC), adjacent to the tube face. In this embodiment, inputs to the model are the backside TEC temperature which can be predicted from model T1-T7, the front side thermoelectric cooler heat input (Watts), and the "Block" temperature which lies adjacent to the opposite vessel or tube face. This completes the model portion of the algorithm. As previously noted, Kalman algorithms typically use a model in conjunction with measured sensor signal/signals that are also part of the model outputs. Here, the measured thermistor signals converted to temperature are used for the front side thermoelectric cooler, and also for the backside thermoelectric cooler. For the case of the backside measured temperature, it is not an output of the model, but it is assumed that they are the same. One reason for this assumption is that the R1 is negligible in terms of overall thermal conductance.

VIII. C. 2. e. Alternative TEC Designs

Variability in module construction can cause slight differences in device performance. For example, current modules are hand-assembled, with machined heat-sinks and interstitial copper layers, and all components are bonded together by hand using conductive epoxy. Variation in epoxy thickness or creation of small angles between components within the module's sandwich construction cause different thermal performance. Most significantly, thermistors are also attached to the ceramic using thermal epoxy. Small gaps between the thermistor and ceramic lead to errors between the control and measured temperatures. Finally, it is very time-consuming to solder the small wires to make electrical contacts for the two TECs, two thermistors, and the fan power leads.

In some embodiments, the thermal device includes a heating and cooling surface (e.g. TEC device as described herein) on each major face (opposing sides) of the reaction vessel. In such embodiments, optical detection can be performed along the minor face (e.g. edge). In some embodiments, optical detection is performed along a first minor face and optical excitation is performed along a second minor face that is orthogonal to the first minor face. Such embodiments may be particularly useful where heating and cooling of larger volumes are needed (100-500 µl fluid samples).

In some embodiments, the thermal control device modules use a custom Peltier device that contains an integrated surface-mount thermistor mounted onto the underside of the ceramic plate in contact with the reaction vessel. A tiny, 0201 package thermistor (0.60 (l)×0.30 (w)×0.23 (t) mm) can be used to minimize convection inside the Peltier device leading to temperature variation by limiting the part thickness. Also, because thermal contact and position of surface-mount thermistors can be precisely controlled, these parts will have very consistent, characterizable differences between the measured and the actual ceramic temperature.

In some embodiments, the thermal control device can include custom Peltiers designed to be fully integrated into a heating/cooling module using semi-conductor mass-production techniques ("pick and place" machines and reflow soldering). The interstitial copper substrate can be substituted for a Bergquist thermal interface PC board (1 mm-thick copper substrate), which have precisely controlled copper thickness and pad dimensions. The Bergquist substrates will also provide pad leads for the backside thermistor and all electrical connections into and out of the module. The backside Peltier will remain a device similar to what is currently used. Finally, the entire TEC assembly can be encapsulated in silicone to make it water resistant. In some embodiments, an aluminum mounting bracket can also double as a heat-sink.

IX. Diagnostic Platform

Figure 38:
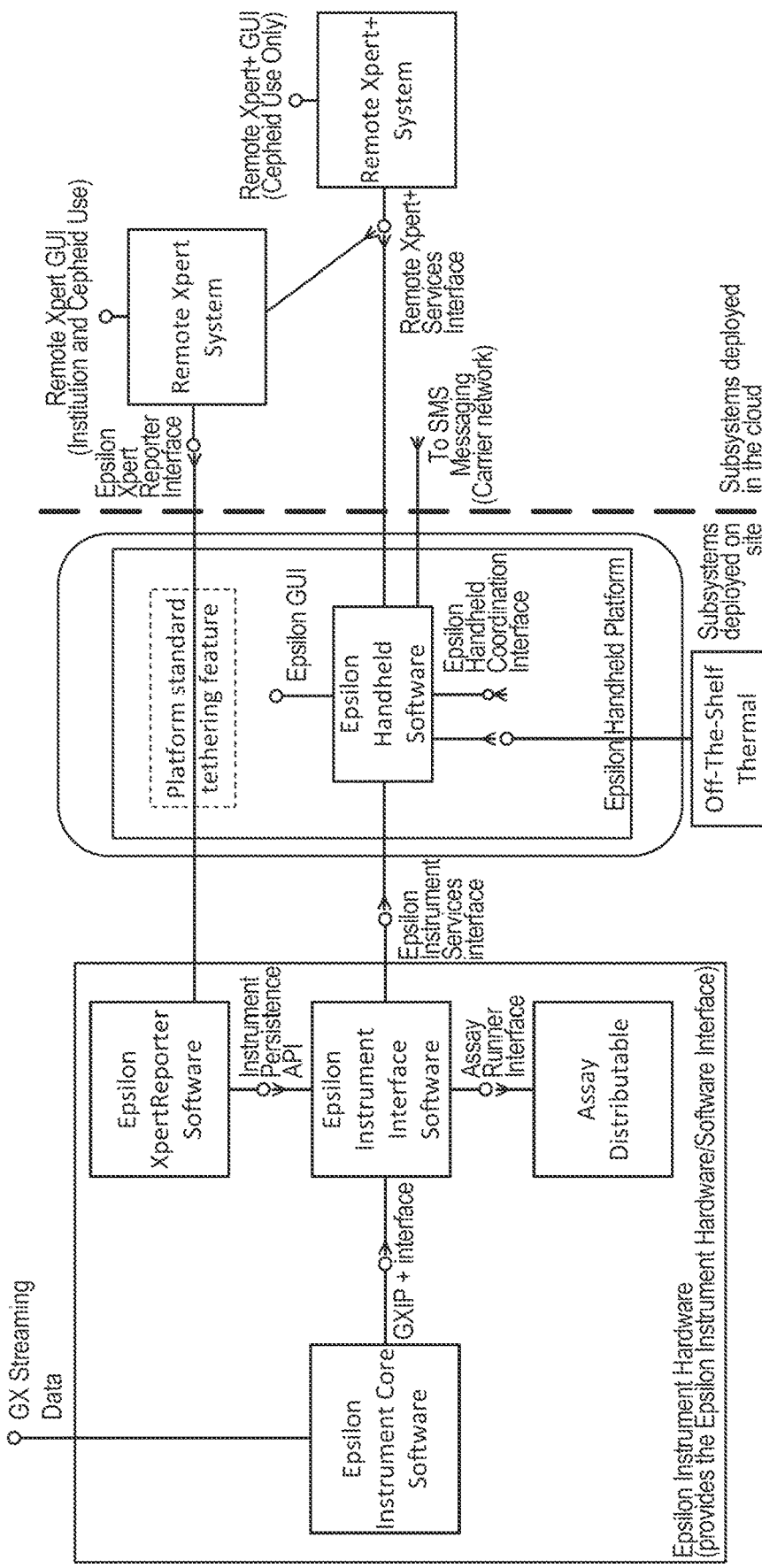
FIG. 38 is an exemplary illustration of the software architecture of a diagnostic assay system according to some embodiments of the invention.

FIG. 38 is a simplified block diagram illustrating an architectural overview of a diagnostic assay system, according to some embodiments of the invention. As with all FIGS shown herein, various embodiments may differ from the examples shown. For example, some embodiments can combine, separate, add to, and/or omit components shown in FIG. 38. Furthermore, the functionality of each of the components can be provided by one or more devices (e.g., computing devices) disposed in one or more geographical locations.

Although the figures may refer to an "Epsilon Instrument," "Epsilon Handheld Platform," and specific remote services, various embodiments that fall within the scope of the invention are not so limited. The techniques described herein are described more generally and can be utilized by any variety of medical devices, mobile or other computing devices, and remote servers. Moreover, specific software components and functionality described herein may be replaced with similarly-functioning software of various types. A person of ordinary skill in the art will recognize some variations to the embodiments illustrated herein and described below.

As illustrated in FIG. 38, the diagnostic assay system can generally include three types of components: a diagnostic device (the "Epsilon Instrument Hardware," also referred to herein and in the figures as an "instrument" or "diagnostic device module" or "diagnostic device"), a mobile device (the "Epsilon Handheld Platform"), and remote services (referring to the illustrated "Remote Xpert System" and "Remote Xpert+ System" collectively). More detailed descriptions of these components are provided below. The diagnostic device and the mobile device can be co-located at a point of care, such as a health clinic, hospital, or other facility, while the remote services can be located at one or more remote locations. Depending on desired functionality, and as indicated above, embodiments may employ multiple diagnostic devices, mobile devices, and/or remote services.

Diagnostic device illustrated in FIG. 38 comprises the illustrated Epsilon Instrument Hardware and the various software components illustrated therein, including the Epsilon Instrument Core Software, Epsilon XpertReporter Software, Epsilon Instrument Interface Software, and Assay distributable. These components can communicate with each other using various interfaces and application programming interfaces (APIs) as illustrated. As mentioned earlier, the diagnostic device can comprise a diagnostic assay system having a combination of testing and computing components configured to conduct diagnostic assays and provide resulting data to remote services via the mobile device. In some embodiments, the diagnostic device may additionally process and/or store the assay data from one or more assay results. Components may be implemented, at least in part, using a combination of software and hardware, which can be incorporated into a computer system (such as that described in relation to FIG. 53).

In some embodiments, the diagnostic device can enable hands-off processing of patient samples (specimens) and provide both summarized and detailed test results data to the remote services. Interface software (shown as the "Epsilon Instrument Interface Software") can enable the diagnostic device to communicate with mobile device software (shown as the "Epsilon Handheld Software") executed on the mobile device. Communication may be done wirelessly using any of a variety of wireless technologies, such as near-field communication (NFC), Bluetooth™, Wi-Fi, and the like.

By establishing this communication with the mobile device, the interface software can thereby enable a user of the mobile device to control various features of the diagnostic device. For example, using a graphical user interface (GUI) provided on a display of the mobile device, the user may be able to manage device settings of the diagnostic device; initiate, pause, or cancel tests conducted by the diagnostic device; specify the remote services to which the diagnostic device sends data; specify the type, content, and/or format of the data; and the like. According to some embodiments, the mobile device may additionally enable a user to access medical and/or other data stored on the diagnostic device. In some embodiments, however, the accessed data may not be stored on the mobile device, thereby helping ensure that the security of the data is not compromised if the mobile device is lost or stolen. This feature is advantageous helping the system meet and comply with various privacy laws, regulations and other standards.

The level of control provided to a user by the interface software via the mobile device, may be dependent on a level of authorization provided by the user and/or mobile device. A user with a higher level of authorization can, for example, access features of the diagnostic device to which a user with a lower level of authorization does not have access. The interface software may provide the authorization and/or authentication of the user and/or mobile device prior to and/or during communication by requiring, for example, login information or similar unique data to help ensure security of the system.

The diagnostic device may communicate with a plurality of mobile devices, and may do so at the same time (or at substantially the same time). As such, this can enable multiple users to control the diagnostic device. To do so, the interface software may provide authorization and/or authentication for each of the plurality of mobile devices. In some embodiments, where a diagnostic device is in active communication with a plurality of mobile devices, one of the mobile devices may be designated as the primary mobile device through which all data is sent to the remote services. In other words, in some embodiments, although a diagnostic device can be controlled by a plurality of mobile devices, the diagnostic device can also be tethered to a single, primary mobile device through which the diagnostic device routes data to the remote services.

The mobile device can comprise a mobile electronic device, such as a smartphone, tablet computer, laptop, and the like. The mobile device software can be executed as an application on the mobile device, and can further be agnostic of the operating system (OS) of the mobile device. As such, any of a wide variety of mobile devices can be able to function as the mobile device described in embodiments herein once the mobile device software is installed on the mobile device and proper authentication is provided. As illustrated in FIG. 38, the mobile device can also be connected with a printing device, such as an off-the-shelf thermal printer.

In some embodiments, the mobile device software can enable authorization and/or authentication of the mobile device with a plurality of diagnostic devices, such that a user can control a plurality of diagnostic devices at once with a single mobile device. In addition to providing control of the diagnostic device via the mobile device software, the mobile device can further enable the diagnostic device to communicate with the remote services (e.g., provide data to the remote services) via a tethering feature that enables data communicated from the diagnostic device to the mobile device (e.g., via, NFC, Bluetooth, Wi-Fi, etc.) to be relayed to the remote services using the connectivity of the mobile device to a wide area network (WAN), which may utilize cellular (e.g., third generation (3G), long-term evolution (LTE), etc.), satellite, and/or other wireless technologies.

More generally, techniques described herein can provide for a diagnostic assay system in which one or more diagnostic assays can be controlled with a mobile device using local area network (LAN)-based functionality on a peer basis. That same protocol can be utilized for WAN communication to remote services discretely on the mobile device. Thus, for this latter functionality, the mobile device can become self-contained router. Although embodiments described herein describe the use of a mobile or "handheld" device, other embodiments can utilize computing systems that may not be considered mobile or handheld, such as a personal computer. Features of the mobile device and other computing devices described herein are described in more detail below in reference to FIG. 53.

According to some embodiments, the tethering feature can provide connectivity between the diagnostic device and the remote services without any persistent data being stored on the mobile device. In other words, the mobile device may not know anything about the data that is being transferred. In some embodiments, for example, the mobile device can receive sensitive encrypted data, such as patient data, from the diagnostic device that is simply passed along to the remote reporting system without being stored or decrypted by the mobile device. In such embodiments, the security of the data will therefore not be compromised if the mobile device is lost or stolen, thereby adding another layer of privacy protection to the system which may help the system comply with governing privacy laws, regulations, or other standards. Moreover, the functionality of the diagnostic assay system can be restored in a relatively simple manner by replacing the lost or stolen mobile device. With such functionality, the techniques described herein can be utilized not just in a laboratory, but also out in the field (e.g., an Ebola clinic in a remote region in Africa) where a mobile device may be more susceptible to loss or theft.

Referring again to FIG. 38, the remote services can be executed in the "cloud" by one or more servers, which can be located at one or more locations remote from the mobile device and/or diagnostic device. The remote services can gather data from one or more diagnostic devices, synthesize the data, and store the data in a database. The remote services can gather data not only from one or more diagnostic devices at a single location (e.g., communicating via a particular mobile device), but also gather information more broadly from diagnostic devices at various facilities in various different geographical locations, thereby being able to provide large-scale epidemiological data and determine other valuable health and disease information among one or more populations.

Additionally or alternatively, the remote services can aggregate and process data and provide a viewing entity (such as a governmental agency) a secure portal (accessible, for example, via the Internet) through which the processed data can be accessed in various forms (e.g., lists, graphs, geographic maps, and the like). The form by which the processed data is viewed is in accordance with the viewing entity's level of authorization. Again, the data sent to and processed by the remote services can be encrypted (or otherwise securely transferred) and/or manipulated in a manner that is compliant with laws, regulations, standards, and/or other applicable governing requirements.

It will be understood that components illustrated in FIG. 38 can communicate with each other using the wireless technologies mentioned above either directly or as part of one or more larger data communication networks, such as the LAN and/or WAN described in the above embodiments. The data communication network(s) can comprise any combination of a variety of data communication systems, for example, cable, satellite, wireless/cellular, or Internet systems, or the like, utilizing various technologies and/or protocols, such as radio frequency (RF), optical, satellite, coaxial cable, Ethernet, cellular, twisted pair, other wired and wireless technologies, and the like. The data communication network(s) can comprise packet- and/or circuit-type switching, and can include one or more open, closed, public, and/or private networks, including the Internet, depending on desired functionality, cost, security, and other factors.

The remaining description and figures illustrate various aspects of the embodiment of the diagnostic assay system illustrated in FIG. 38. Although particular hardware and software components are described with respect to the disclosed embodiment, a person of ordinary skill in the art will recognize that, in some embodiments, some such components can be substituted, replaced, omitted, and/or otherwise altered as compared to other embodiments. For example, programmable systems on a chip (PSoC) can be replaced with multiple components to provide substantially the same functionality. A person of ordinary skill in the art will be familiar with various mixed signal and/or analog microcontrollers that are suitable for use with the invention. Representational State Transfer (REST) interfaces may be replaced and/or used in conjunction with other data structures and/or protocols where appropriate, such as Create, Read, Update and Delete (CRUD); Domain Application Protocol (DAP); Hypermedia as the Engine of Application State (HATEOAS); Open Data Protocol (OData); RESTful API Modeling Language (RAML); RESTful Service Description Language (RSDL); and the like.

IX. B. Epsilon Instrument Core Software

As illustrated in FIG. 38, in some embodiments the Epsilon instrument core software (also referred to as diagnostic assay system software) can include a variety of software modules. Suitable modules that can be included in the instrument core software can include a Cellcore operating system module, a hardware state machine module (HSM), an iCORE software module, a valve software module, a syringe/door software module, and/or an ultrasonic horn software module. In some embodiments, the Cellcore operating system module is a version of linux and supporting services running on the Cellcore processor. In some embodiments, the HSM module can include all diagnostic device specific software running on the Cellcore processor and outside of a Java Virtual Machine (JVM). In some embodiments, the iCore Software module includes all software running on the iCore PSoC. In some embodiments, the Valve Software module includes all software running on the Valve PSoC. In some embodiments, the Syringe/Door Software module includes all software running on the Syringe/Door PSoC. In some embodiments, the Horn Software module includes all software running on the Horn PSoC.

In some embodiments the Epsilon instrument interface software can include an Epsilon instrument REST interface module and an Epsilon Assay Runner Software module.

In some embodiments, the Epsilon Xpert Reporter Software operates as a client of the Remote Xpert Software and runs on the Cellcore processor of the Epsilon instrument Hardware in the same JVM as the Epsilon Instrument Interface Software.

The Epsilon Instrument Hardware can be the physical subsystem that performs assays. In some embodiments, this subsystem may only include the hardware of the instrument, with the software running on the instrument as a separate subsystem.

IX. C. Mobile Device

As illustrated in FIG. 38, in some embodiments the mobile device can include a variety of software modules. For example, embodiments of the illustrated Epsilon Handheld Software can comprise an Android application, executed by the mobile device, specifically designed to support the system illustrated in FIG. 38 when deployed in the field context. In some embodiments, an application for another operating system can be utilized. In some embodiments, the software can include all of the necessary features to support performing tests on patients in the field utilizing the diagnostic device, and/or features to facilitate the Cepheid Service Department (or a service department of another provider) remotely supporting these instruments.

In some embodiments, the mobile device can comprise an off-the-shelf Android handheld target platform, selected to support the field context.

IX. D. Remote Xpert+System

In some embodiments, the Remote Xpert+System illustrated in FIG. 38 can comprise a collection of web applications exposed as services to be used by Remote Xpert System and the Epsilon Handheld Software. REST and/or similar services (as previously described) can be used for internal communication within Remote Xpert+. In some embodiments, a limited number of services of the Remote Xpert+System can be exposed to external systems, such as the Remote Xpert and Epsilon Handheld Software. According to some embodiments, a primary role of Remote Xpert+ can be to allow central management of users, institutions, commands, and kits.

IX. E. Remote Xpert System

In some embodiments, the Remote Xpert System illustrated in FIG. 38 can comprise a collection of web applications used by institutions to manage their instruments and clinical data. Such institutions can include, for example, national or international agencies (e.g., the World Health Organization), emergency response organizations, universities, hospitals, and the like. In some embodiments, the Remote Xpert software can further include parsing software to parse incoming and/or outgoing data.

IX. F. Assay Distributable

In some embodiments, components of an embodiment of the assay distributable of the diagnostic device illustrated on FIG. 38 can include an assay header (summary information used to manage the assay), an assay definition (which can be, for example, a received file), and/or assay UI tailoring (which defines the assay specific UI such as specific sample preparation presentation instructions. Such tailoring can be limited to areas identified by the UI design, such as sample preparation steps and/or assay specific help screens). In some embodiments, the assay distributable may optionally include assay specific software, which can allow the incorporation of new algorithms as needed for future assays. This can require that the software executing assays supports this type of extension. Additionally, in some embodiments, the assay distributable may include localized handheld assay resources, as needed. This can include various resources used to implement the UI for a specific assay. Examples include localized strings for supported languages, new graphic resources such as icons if any, and/or any help files required (e.g. Portable Document Format (PDF) of the package insert or training videos). It can be further noted that, in some embodiments, the localized resources may need to be separated into an "assay language pack" or kit due to size constraints (e.g. localized training videos) and regional variations.

IX. G. External Interfaces—Diagnostic Device

In some embodiments, the diagnostic device illustrated on FIG. 38 can include one or more external interfaces. For example, the Epsilon Handheld App GUI can be a user interface on the mobile device that acts as the user interface of the diagnostic device as well. The Remote Xpert GUI can be a web-based user interface provided by Remote Xpert. The Remote Xpert+GUI can be a web-based user interface provided by Remote Xpert+. In some embodiments, this GUI may be accessible only by the entity providing and/or maintaining the Remote Xpert+. Additionally or alternatively, external interfaces can include SMS messaging, which can be used to report results to an institution clearing house, and can be provided by the carrier via the mobile device operating system. The diagnostic device can include a data streaming interface (the GX Streaming Data interface illustrated in FIG. 38) that enables a personal computer (PC) or other computing device to provide a visualization of the data, which can aide in development and debugging. As such, this interface may not be used when deployed in the field, in some embodiments.

IX. H. Internal Interfaces—Diagnostic Device

In some embodiments, the diagnostic device illustrated on FIG. 38 can include one or more internal interfaces. For example, the Epsilon Instrument Hardware/Software interface can comprise an interface between the instrument hardware and the Epsilon Instrument Core Software. The GXIP+interface can comprise an interface provided by the Epsilon Instrument Core Software and used by certain software in both the clinical setting context and in the field use context. The Assay Runner Interface can be provided by the Epsilon Instrument Interface Software and used by the Epsilon Assay Runner Software or similar assay software. The Instrument Persistence API can comprise an interface provided by the Epsilon Instrument Interface Software and used by the Epsilon Xpert Reporter Software.

IX. I. Mobile Device Interfaces

In some embodiments, the mobile device can include a variety of interfaces. For example, the Epsilon Instrument Services interface can comprise the primary interface provided by the Epsilon Instrument Interface Software. For the field use context, this can be the interface used by the Epsilon Handheld Software to perform tests, get instrument status updates, and other normal operations.

The Thermal Printer Interface can comprise an interface provided by the optional thermal printer, which can be an off-the-shelf model with a Wi-Fi network connection. This can enable the Epsilon Handheld Software to print tests results on the printer either automatically or at the request of a user after a test result is available. In some embodiments, printers utilizing other technologies (e.g., ink, inkjet, etc.) can be used.

The Android Platform API can comprise interfaces provided by the Android Operating System used to access services of the mobile device hardware and the network. As indicated previously, alternative embodiments may include equivalent or similar components for alternative operating systems.

The coordination interface, which is illustrated in the embodiment of FIG. 38, provides for coordination between mobile devices when multiple mobile devices are simultaneously active at a particular location, which may happen at busy sites when more than one user is working or when there is a spare mobile that is active. The coordination interface can be implemented to cross-connect all the modules to the user interface functional control layer on the mobile device. The purposes and functions allow multiple instruments to be controlled and monitored via the mobile device as autonomous units, and provide workflow coordination between the devices for the operator to use the correct instruments for running a given diagnostic. Peer-to-peer, Wi-Fi-managed instruments can have an assured specific control per device and maintain the chain of custody and critical patient identification parameters. The resulting functionality enables a X:Y ratio of mobile devices to diagnostic devices, where X is any number of mobile devices, and Y is any number of diagnostic devices. In some embodiments, X and Y may be the same number.

IX. J. Remote Service Interfaces

As shown in FIG. 38, the remote services can include various interfaces, in some embodiments. For example, the Epsilon Xpert Reporter Interface can comprise a collection of REST services that expose the following capabilities: clinical data upload and/or instrument synchronization. The Remote Xpert+Services Interface can comprise collection of REST services that expose the following capabilities: kit management, user management, institution & site management, remote service commands, and/or instrument synchronization.

IX. K. Clinical Laboratory Improvement Amendments (CLIA)-Waived Applications

In some embodiments, the core software interface of the diagnostic device of FIG. 38 can be utilized in a Clinical Laboratory Improvement Amendments (CLIA)-waived application. Here, the diagnostic device can provide information to proprietary software executed on a personal computer via an Ethernet connection. Alternative embodiments can employ other computing hardware, software, and/or physical or wireless connections. Additional details regarding the GXIP+interface are provided below.

IX. L. Diagnostic Device—Software Components

Figure 39:
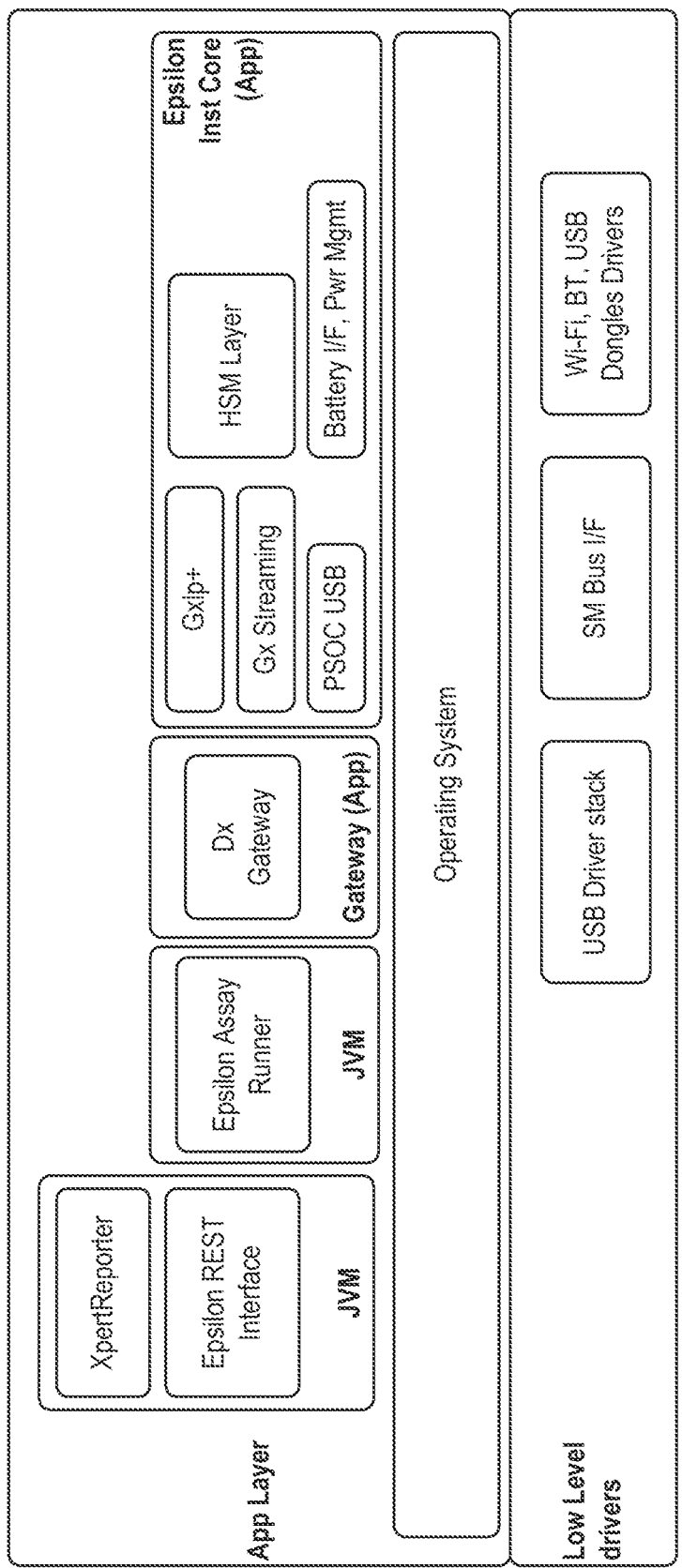
FIG. 39 provides a logical view of software executed by the diagnostic device, according to some embodiments of the invention.

FIG. 39 provides a logical view of software executed by the diagnostic device, according to an embodiment. As illustrated, the software can include low level drivers including the universal serial bus (USB) driver stack, SM Bus I/F, and Wi-Fi, Bluetooth, and USB dongle drivers. The application layer includes the operating system, as well as other applications. These applications can include a JVM having XpertReporter and Epsilon Rest Interface components, a JVM having an Epsilon Assay Runner component, a gateway application having a DX Gateway component, and/or an Epsilon Instrument Core application having GxIp+, Gx Streaming, PSoC USB, HSM Layer, and Battery I/F and Power Management components.

Figure 40:
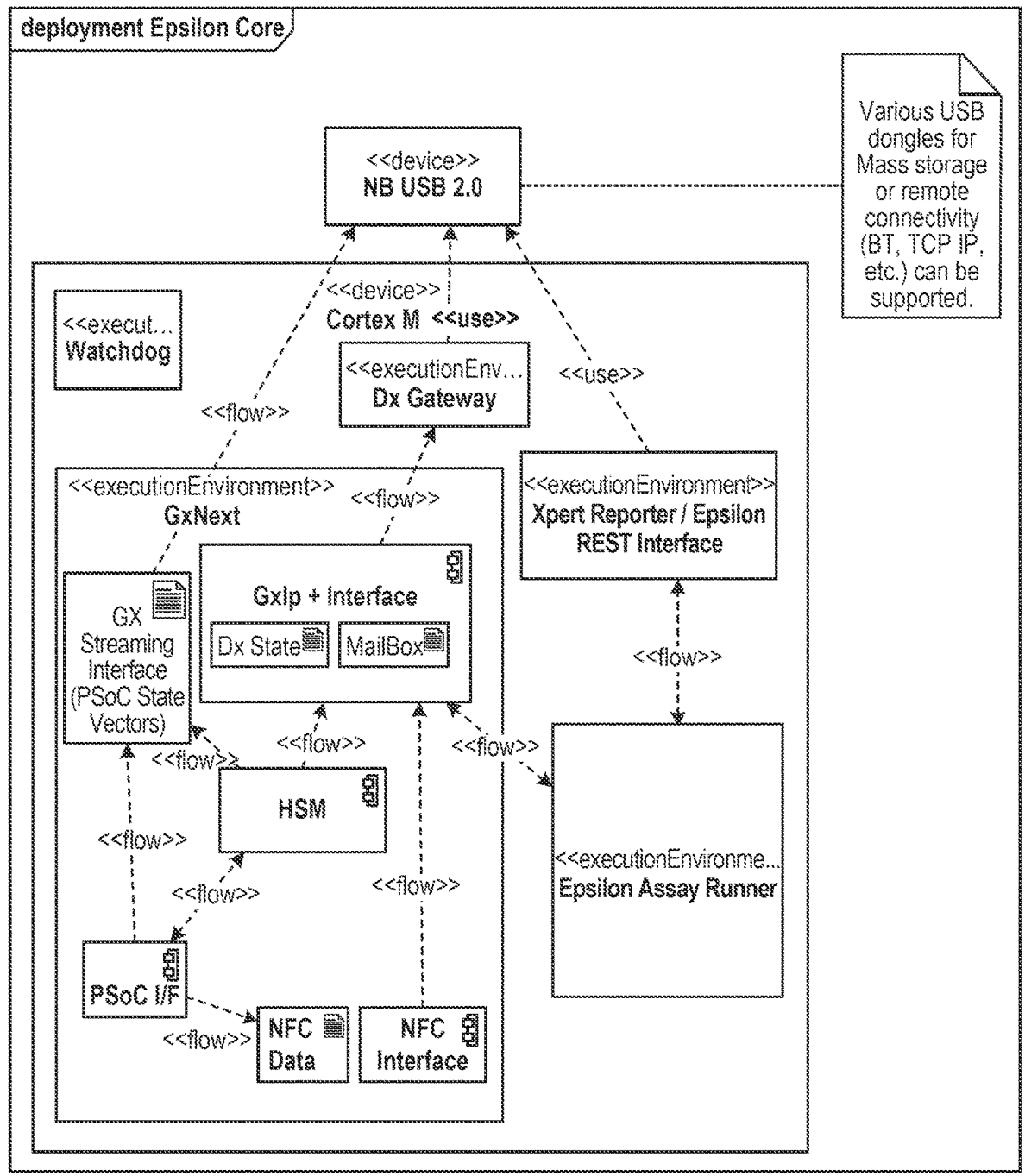
FIG. 40 is a block diagram of the diagnostic assay system (Epsilon Instrument Core Architecture), according to some embodiments of the invention.

FIG. 40 is a block diagram of the Epsilon Instrument Core Architecture, according to some embodiments. The block diagram illustrates the interaction of various subcomponents of the Epsilon Instrument Core Architecture including the NFC Interface, GxIp+Interface, HSM. PSoC I/F, Gx Streaming interface, Xpert Reporter/Epsilon REST Interface, Epsilon Assay Runner, Dx Gateway, and NB USB, as described herein.

In some embodiments, the GxIp+interface can be the primary component supporting the GxIp protocol and can implement the required Dx business logic. The business logic can be ported from 683xx legacy code as a basis for the "Northbound" instrument interface to ensure conformity in how assays and commands are executed. In some embodiments, the GxIp+Interface can further contain the adaptive layer connecting the "Northbound" Legacy GxIp Commands and the "Southbound" Epsilon PSoC Command interface. For the HBDC context, this can be the Dx equivalent interface used by the Epsilon Instrument Interface Software to run and monitor assays.

In some embodiments, the Gateway interface can be the component supporting the GxIp 'Discovery' protocol. Once discovery is complete, this component can act as a router for remote GxIp based components and the GxIp+interface. In some embodiments, the Gateway interface can be the discovery interface on the Epsilon Instrument.

In some embodiments, the GxStreaming interface can be the primary component supporting streaming of Epsilon Core state vectors to a remote client. During development this interface can be used to support the Engineering Visualization Tool (VT) for monitoring and tuning PSoC performance, sonication and fluorimeter equivalence monitoring with respect to the Legacy system. In some embodiments the GxStreaming interface allows streaming of state swap data to the mobile device.

FIGS. 41-1 to 41-4 are diagrams illustrating various states of the HSM component, according to some embodiments. As used in this disclosure, the HSM can comprise the primary component managing the core instrument state as well as the legacy DX compatible sub-states. Additionally, the HSM can interact with the GxIp component to enable or disable GxIp commands depending on the current instrument core state. As illustrated in FIG. 104, high-level states can include, in some embodiments, POST—Power On Self Test, RECOVERY, IDLE, WAITING_FOR_CART, LOADING_CART, CARTRIDGE_LOADED, RUNNING_ASSAY, ABORTING, and CARTRIDGE_PRELOAD. It will be understood by a person of ordinary skill in the art that the names of these states are provided as non-limiting examples, and names and functionality of such states can vary, depending on desired functionality.

Figure 42:
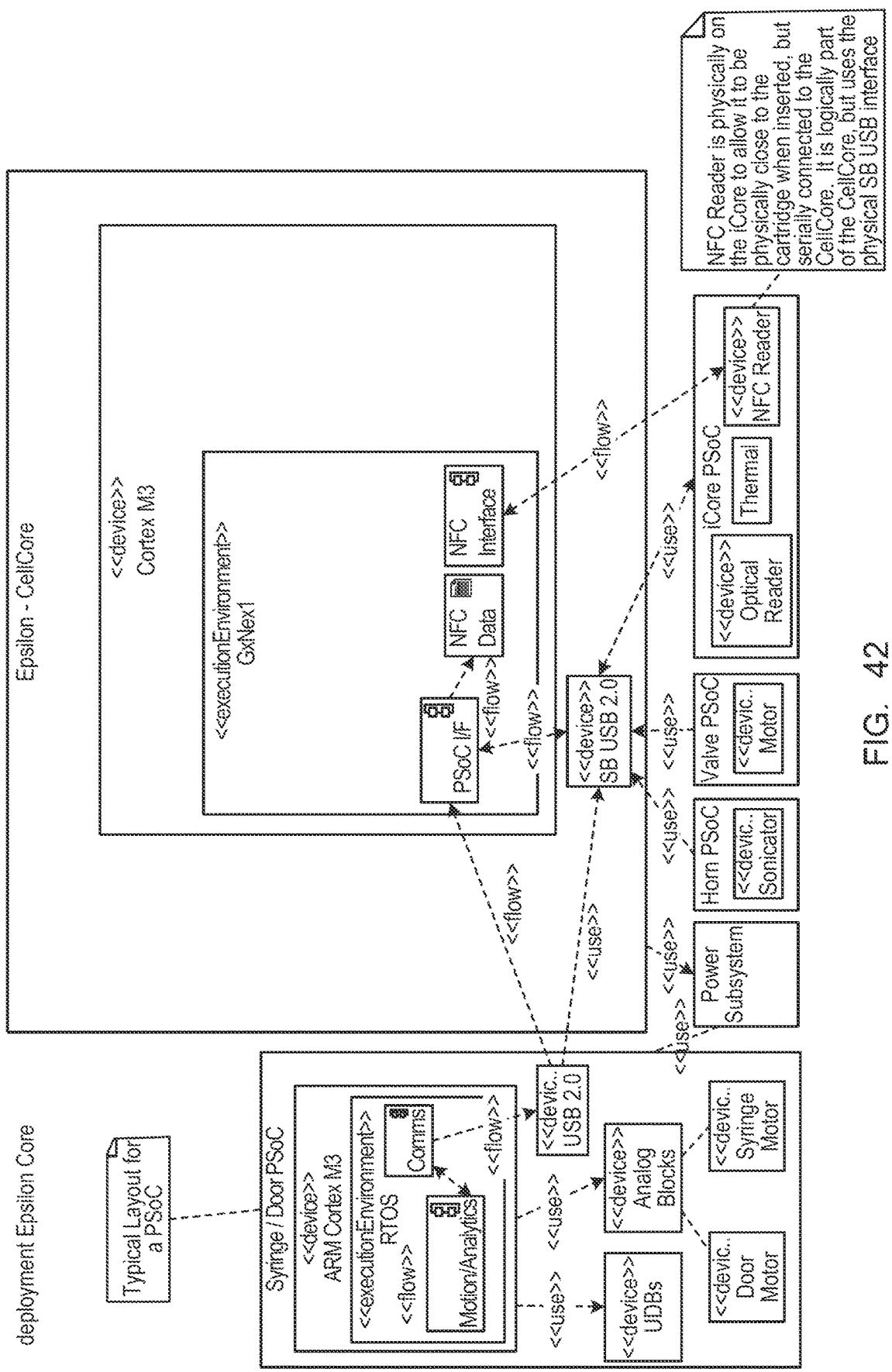
FIG. 42 is a diagram illustrating instrument core internal components and interfaces, according to some embodiments of the invention.

FIG. 42 is a diagram illustrating instrument core internal components and interfaces, according to some embodiments. The PSoC USB, for example, is an internal interface that can be a primary component supporting the "Southbound" interface to the PSoC Components (Horn, Door, Syringe, Valve, and ICORE). The component can use USB 2.0 to create a 'data-backplane' between the Cell Core and each PSOC. In some embodiments, during boot-up, PSoCs can be enumerated boot loadable endpoints, allowing new firmware to be programed on each PSoC. In some embodiments, during normal operations, PSoCs can be enumerated as a command endpoint and a State Swap end point. Here, State Swap can afford high speed PSoC data virtualization on the Cell Core, allow monitoring and/or analysis of high speed PSoC data on the Cell Core, and/or support the Gx Streaming component on the Cell Core.

In some embodiments, instrument PSoC external interfaces can include Comms_Task, which can be a primary PSoC component supporting the "Southbound" interface between the PSoC and the Cell Core. It can further be a main component Pn the PSoC to create a "data-backplane" between the Cell Core and each PSoC. Additionally or alternatively, the Comms_Task can be common to all PSoCs can create and manage the Command and State Swap USB endpoint interface.

In some embodiments, the Analytics Task can comprise another PSoC external interface, which can be a primary PSoC component supporting the PSoCs command handling. In some embodiments, the Analytics Task can include common handling for common commands shared by all PSoCs.

Instrument PSoC external interfaces can further include ISRs, according to some embodiments of the invention. ISRs can allow for common handling for time on PSoCs, and/or specific priority processes for supporting background trajectory.

IX. M. Mobile Device—Software Components

Figure 43:
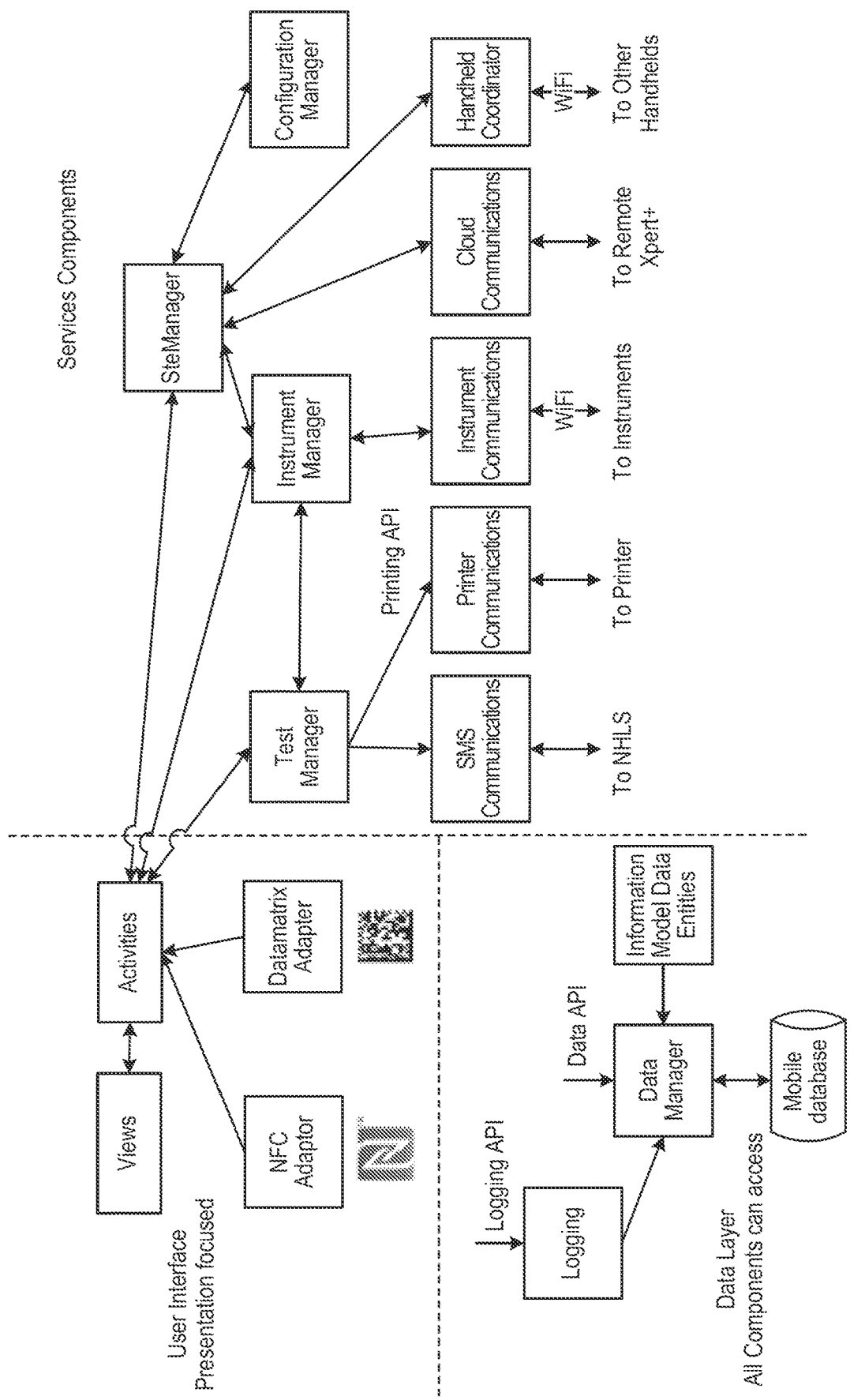
FIG. 43 is a block diagram illustrating software components executed on a mobile device, according to some embodiments of the invention.

FIG. 43 is a block diagram illustrating software components executed on a mobile device, according to some embodiments of the invention. Here, the User Interface can follow common Android (or other OS) design patterns. Activities can be the components that control the flow through the user interface and which views are visible at any time. Views can be the set of components that present information to the user. In some embodiments, most of the business logic can be contained in the Services Components shown in FIG. 43.

In some embodiments, the User Interface can present the specific workflow required to run cartridge-based diagnostics on a standalone module and assure accuracy and granularity of patient data correlated with a specific diagnostic result. This includes automated chain of custody from sample logging through a cartridge and into the instrument database.

According to some embodiments, the Data Layer can include a Data Manager that provides all database persistence in the application. In some embodiments, the Mobile Database can be SQLite and can be encrypted using SQLCipher. The mobile database can include authorized users, credentials, and/or logging information. Because the mobile device can act as a self-contained mobile router for diagnostic data transport, the data in the database can provide credentials and authentication to initiate and terminate the transport connections. Additional information regarding establishing these connections is provided below. In some embodiments, the Data Layer can further provide two API's to the rest of the system: a Data API for normal database objects, and a Logging API for logging key events. These APIs allow the mobile diagnostic device to connect with the remote database and transparently move the diagnostic and other descriptive data via the mobile device from the diagnostic device to the contextually correct Internet instance of RemoteXpert.

As illustrated in FIG. 43, embodiments may include a Site Manager, which manages the state of the site and can keep a list of known users, known diagnostic devices, known mobile devices, known assays, and/or known printers. When the mobile device is connected to the internet, the Site Manager can coordinate with Remote Xpert+ to manage remote service command for the site. The site manager can further interact with peer mobile devices as necessary to manage site state, and/or handle user authentication.

Some embodiments can further include a Cloud Communications, which can provide access to the Remote Xpert+ Services, and/or a Configuration Manager, which manages the current configuration of the mobile device. In other words, the Cloud Communications component can establish and manage a bi-directional communication link with one or more remote services (e.g., the Remote Xpert+ as illustrated on FIG. 38). The communications can be established via one or more APIs that can to parse, interpret, and transmit data (e.g., in a proprietary format) into a standard readable format.

As further illustrated in FIG. 43, embodiments may include an Instrument Manager, which manages the current list of instruments (medical diagnostic devices), and monitors the state of all the instruments at the site. The Instrument Manager can further provide the ability to perform operations on the diagnostic device(s). Such operations can include, for example, run a test using an assay, install an assay, install a software upgrade, perform diagnostics, and/ or synchronize time reference. The Instrument Manager can further select an instrument when requesting a test and/or handle errors reported by an instrument. According to some embodiments, the Instrument Communications can encapsulate the communication with the REST API of the medical diagnostic device.

Some embodiments may further include a Test Manager that can manage the list of active tests, manage the workflow of performing a test, report results of the test after it is complete, and/or "archive" the test when no longer active. In some embodiments, SMS Communications can encapsulate the reporting of results via SMS to an institutional clearing house. In some embodiments, Printer Communications can encapsulate the ability to print reports on a local thermal printer.

Generally speaking, functionality of the mobile device can be dependent on available software development kits (SDKs) and APIs for various platforms. For example, for Android SDK and APIs, the application functionality is limited by the public APIs of the Android SDK. Even so, the Android SDK and APIs may be used to provide access to NFC, Camera, GPS, SMS Messaging, and/or the network.

Some embodiments may use SQLite and SQLCipher, which is the standard database on Android. For instance, SQLCipher is referenced by the Open Web Application Security Project (OWASP) as the preferred way to secure data on the phone. Nonetheless alternative embodiments may utilize other platforms, such as iOS, Windows Mobile, and the like. Additionally or alternatively, other data structures and/or query languages may be utilized, such as SQL, HTSQL, jOOQ, and the like.

Some embodiments can provide for a third party remote support application which enables remote display and, if available, remote control of the mobile device provided by a third party application. In some embodiments, versions of the mobile device software can use a related SDK to provide remote control of the application.

Among other things, the invention provides for the consolidation of the control of diagnostic device(s), management of the device(s), and LAN and WAN connectivity functions (LAN to WAN routing, as previously described) on the mobile device, which are not employed by traditional medical diagnostic industry controls and communications. The segmentation of local control of the devices (the LAN layer) and communication with each of the diagnostic instruments can be done on a peer-to-peer level (e.g., via Wi-Fi) and manages the data flow for each instrument—both for the UI control functional interface and then the data path interface up the RemoteXpert in the cloud.

The use of NFC on the mobile device, the NFC Adapter shown in FIG. 43, can be used to control chain of custody for patient samples. The medial data provided to the claim can enable traceability of these functions, which can be stored in a central cloud repository. NFC can tie a cartridge containing a patient sample simultaneously to a separate NFC signal from the diagnostic device to assure matching for the custody and reporting accuracy requirements.

FIG. 43 further illustrates the instrument communications component, which can establish a peer-to-peer Wi-Fi connection between the mobile device and the diagnostic device. The instrument communications component can enable multiple mobile devices to communicate with one another. In some embodiments, the Handheld Coordinator can provide coordination among multiple mobile devices via Wi-Fi.

IX. N. Remote Diagnostics Reporting Service—Software Components

Figure 44:
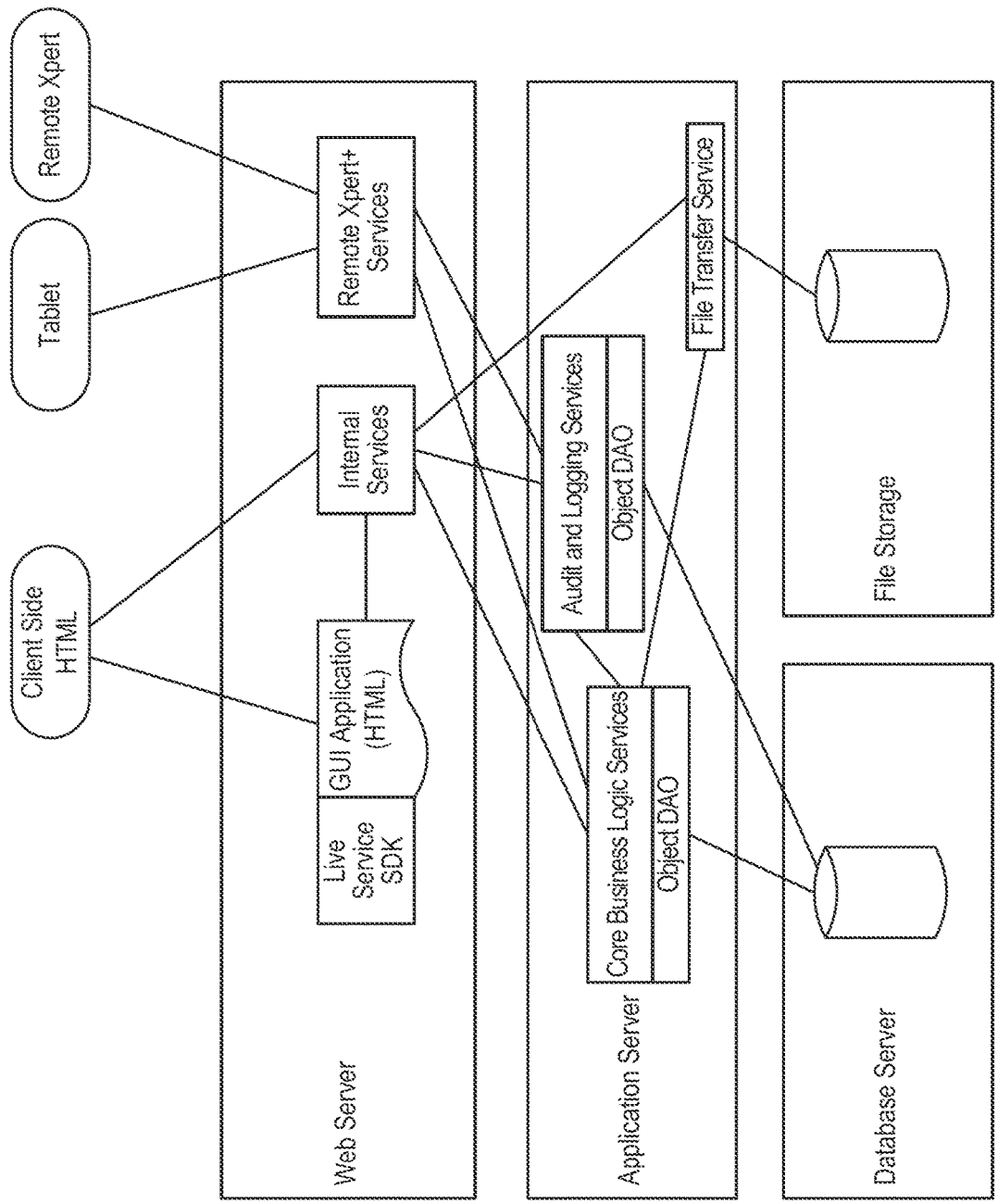
FIG. 44 is a block diagram illustrating software components executed by a remote diagnostics reporting service, according to some embodiments of the invention.

FIG. 44 is a block diagram illustrating software components executed by a remote diagnostics reporting service for medical diagnostics and epidemiology, according to some embodiments of the invention. The remote diagnostics reporting service comprises, among other things, a web server, application server, database server, and file storage.

According to some embodiments, the logical components of the remote diagnostics reporting service illustrated in FIG. 44 can be described as follows. The Remote Xpert+ Services can comprise REST web services to be used by the mobile device and Remote Xpert. The GUI Application can comprise a web application to be used by an entity providing service and support to the diagnostic assay system. The Private Services can comprise REST web services to be used by the GUI application. The Core Business Logic Services can comprise REST web services containing all business logic. The Audit and Logging Service can comprise REST web services containing all logging and auditing capabilities. Finally, the File Transfer Service can comprise a REST web service to abstract the file storage solution.

Among other benefits, the diagnostics reporting service illustrated in FIG. 44 enables automated remote diagnostics reporting from a Class 2 or Class 3 medical diagnostic device into a remote database and presentation layer. Additionally, layered authentication allows real time remote control for debugging and diagnostics on a remote Class 2 or Class 3 medical diagnostic device across a WAN connection. This can be a service consolidation of discrete functions including real time diagnostics and time series data specifically for application in a PCR based diagnostic environment.

IX. O. Setup of a Diagnostic Assay System—Workflow

An example workflow for a setup of a molecular diagnostic assay system such as the system shown on FIG. 38 can include the following stages. It will be understood that although specific wireless technologies (e.g., GSM, CDMA, Wi-Fi, etc.) are mentioned in the example embodiments provided below, additional or alternative technologies may be used, depending on desired functionality.

First, mobile devices can be commissioned to work in the diagnostic assay system. Here, mobile devices utilize an internet connection (e.g., a cellular connection, Wi-Fi, etc.). For cellar connections (e.g., GSM, CDMA, etc.), the mobile devices may need to be provisioned by a carrier. Additionally, mobile devices can be configured via Remote Xpert+, which can entail downloading an initial set of users, determining an authorized set of assays, and being assigned to a site.

Second, the Wi-Fi Network can be configured. Here, a mobile device can be selected to become Wi-Fi hotspot (e.g., the bridge between LAN and WAN networks), and other mobile devices can connect with the Wi-Fi hotspot. In some embodiments, all diagnostic devices can use a single mobile device acting as a Wi-Fi hotspot to access the Remote Xpert directly. Additionally or alternatively, one or more additional mobile devices can connect via Wi-Fi to the mobile device acting as the hotspot. If the mobile device acting as the hotspot fails, runs out of power, or is lost, a second mobile device can be used in its place.

Third, the diagnostic devices can be configured. In some embodiments, this process can involve sharing Wi-Fi information (e.g., SSID and passphrase) and/or other information with the mobile device. The mobile device can also get identifying information form the diagnostic devices, such as MAC address, serial number, etc. Such information sharing can be conducted using peer-to-peer NFC. Additional diagnostic devices can be added in the manner above. If physical ordering is important, the UI of the mobile device can allow a user to specify where the new instrument is to be placed.

IX. P. Data Flows of the Diagnostic Assay System

Figure 45:
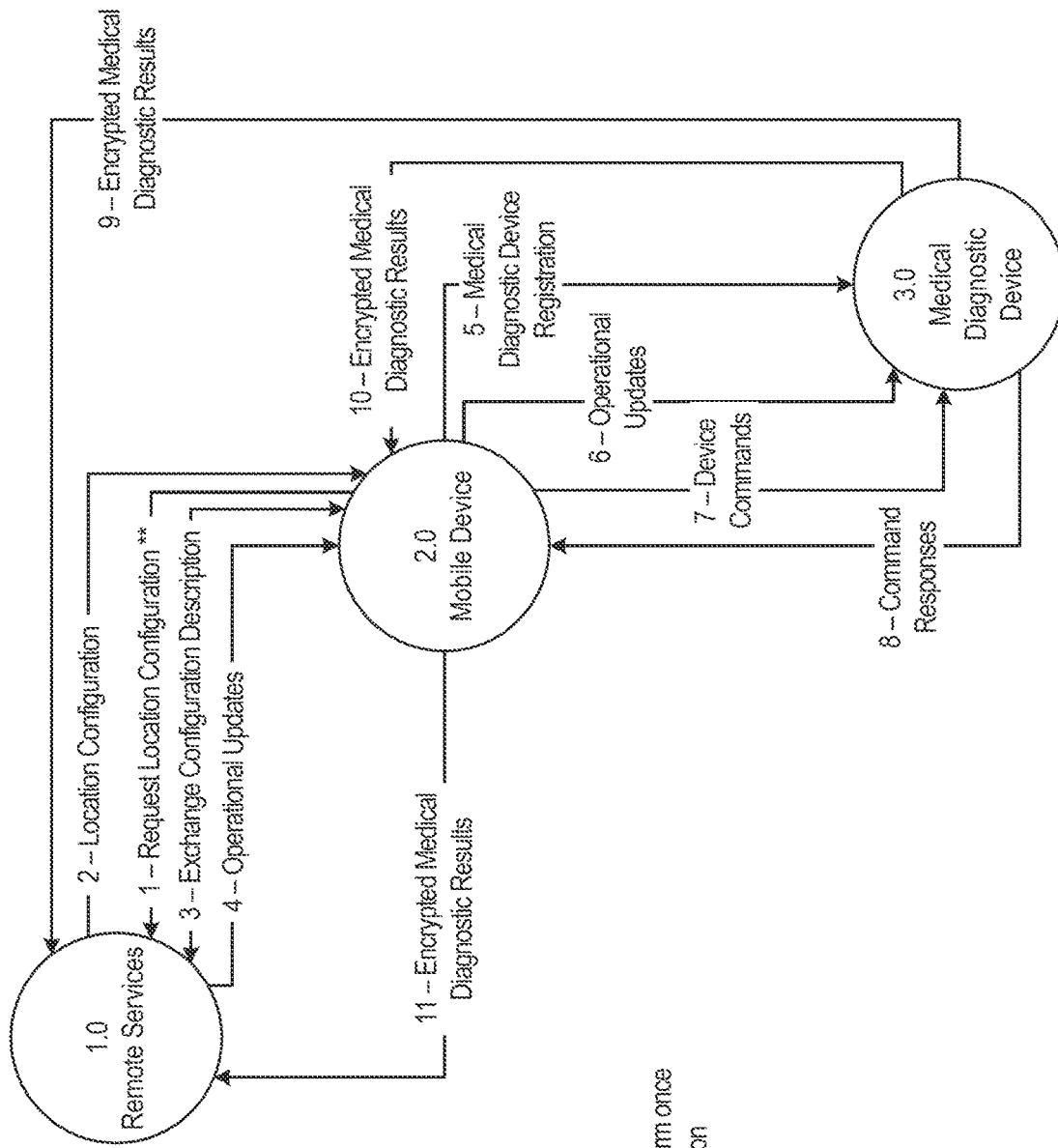
FIG. 45 is a data flow diagram illustrating top level data flow in a diagnostic assay system, according to some embodiments of the invention.
Figure 46:
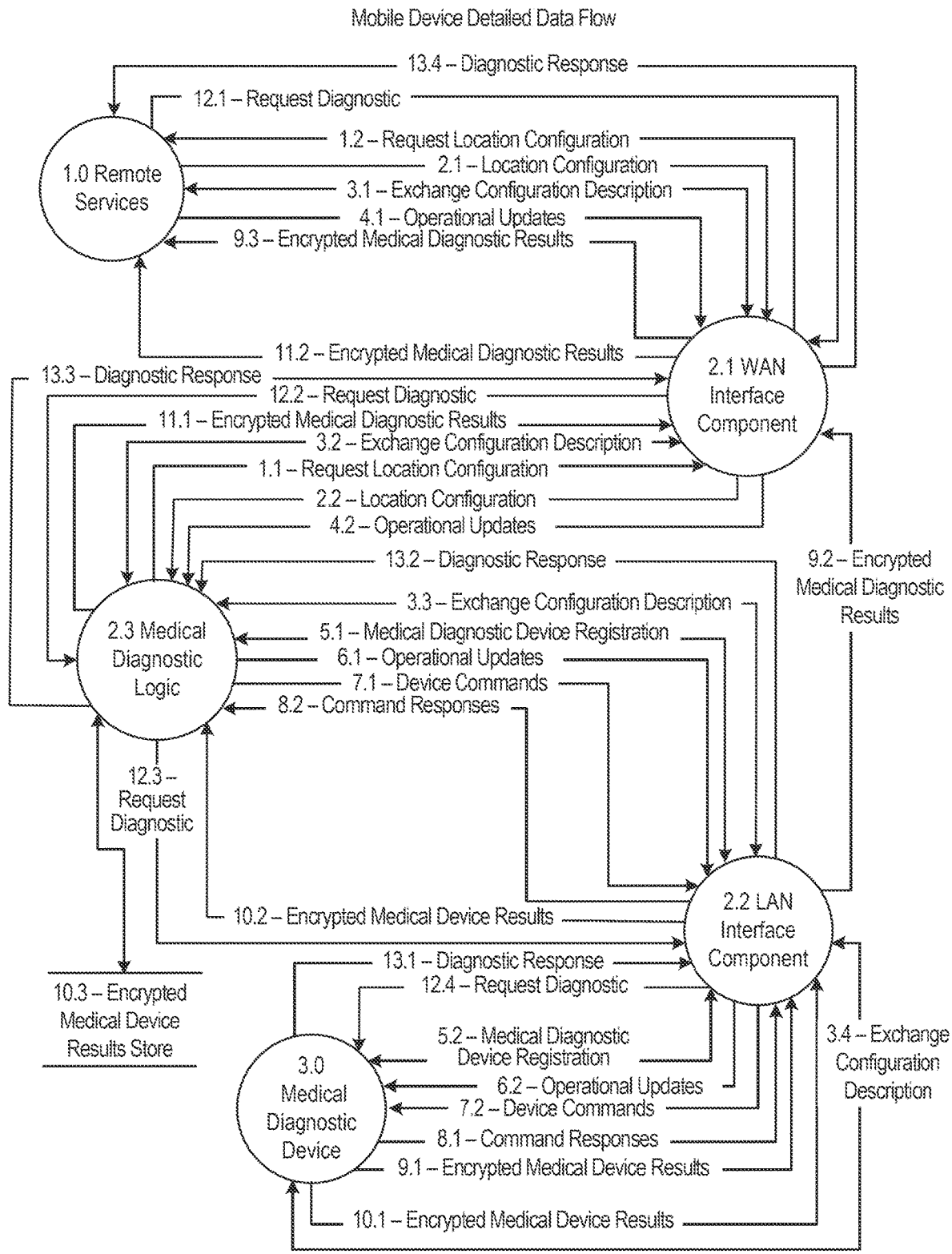
FIG. 46 is a data flow diagram illustrating an embodiment of a more detailed data flow than FIG. 45, in which components of the mobile device are separately portrayed.

FIGS. 45-46 are data flow diagrams illustrating different aspects of a diagnostic assay system, according to some embodiments of the invention. As with other figures provided herein, FIGS. 45-46 are provided as non-limiting examples. Alternative embodiments can include additional functionality to that shown in the figure, and/or the functionality shown in the figure may be omitted, combined, separated, and/or performed simultaneously. Means for performing the functionality of the blocks may include one or more hardware and/or software components, such as those shown in FIGS. 38 and 53. A person of ordinary skill in the art will recognize some variations.

IX. Q. Diagnostic Assay System Top Level Data Flow

FIG. 45 is a data flow diagram illustrating top level data flow in a diagnostic assay system, such as the one illustrated in FIG. 38. Here, the components of the diagnostic assay system-remote services, mobile device, and diagnostic device—are portrayed as circles, and data flow is portrayed as arrows.

The data flow can initiate with the mobile device sending the remote services a request for location configuration (1). The request can be made when the mobile device is at a new site where the diagnostic device is located. As indicated in FIG. 45, the request may only need to be performed once per location.

The remote services then responds with location configuration (2), and the remote services and mobile device exchange configuration description (3). As previously indicated, this involve downloading, from the remote services to the mobile device, an initial set of users, determining an authorized set of assays, and more. The remote services can also provide operational updates (4) to the mobile device.

The mobile device can then engage in a configuration process with the diagnostic device. In this process, the mobile device provides diagnostic device registration (5) an operational updates (6) to the diagnostic device.

Once configured, the diagnostic device can receive operational instructions from the mobile device. The mobile device can then provide device commands (7) to the diagnostic device, which may be based on user input. As indicated previously, such commands can include, for example, run a test using an assay, install an assay, install a software upgrade, perform diagnostics, and/or synchronize time reference. The diagnostic device can provide command responses (8), such as acknowledgements, status updates, and the like.

Where device commands (7) result in executing medical diagnostics, the diagnostic device can then provide encrypted medical diagnostic results (9) to the remote services. As indicated previously, the mobile device may provide a hotspot through which the diagnostic device may send the encrypted medical diagnostic results (9). However, the mobile device may not decrypt or store the data. As such, according to some embodiments, the mobile device acts simply as a conduit through which the encrypted medical diagnostic results (9) can be reported to the remote services. In some embodiments, encrypted medical diagnostic results (10) can be sent to the mobile device and stored. (As previously discussed, in some embodiments, the data may not be stored on the mobile device. In such embodiments, the mobile device can send the data to another device—e.g., a storage device on the LAN, a computer, etc.—for storage.) Depending on desired functionality, the encrypted medical diagnostic results (10) sent to the mobile device may be the same or different than those sent to the remote services.

IX. R. Mobile Device Detailed Data Flow

FIG. 46 is a data flow diagram illustrating a more detailed data flow in which components of the mobile device-WAN interface component, medical diagnostic logic, and LAN interface component—are separately portrayed.

Similar to the flow of FIG. 45, the flow shown in FIG. 46 can begin with a configuration process between the mobile device and remote services. Here the medical diagnostic logic sends a request for location configuration (1.1) to the WAN interface component, which then sends a request for location configuration (1.2) to the remote services. The remote services respond by providing location configuration (2.1) to the WAN interface component, which provides the location configuration (2.2) to the medical diagnostic logic. Configuration description is then exchanged between the remote services and WAN interface component (3.1), the WAN interface component and medical diagnostic logic (3.2), medical diagnostic logic and LAN interface component (3.3), and LAN interface component and medical diagnostic device (3.4). Operational updates are then passed from the remote services to the WAN interface component (4.1) and from the WAN interface component to the medical diagnostic logic (4.2).

The diagnostic device configuration can include medical diagnostic device registration (5.1), (5.2), using the medical diagnostic logic, LAN interface component, and the device. These components further pass operational updates (6.1), (6.2) from the medical diagnostic logic to the diagnostic device.

Device commands (7.1), (7.2) can then be sent from the medical diagnostic logic to the diagnostic device, and command responses (8.1), (8.2) can be sent back from the diagnostic device to the medical diagnostic logic.

Encrypted device results (9.1), (9.2) may be sent from the diagnostic device to the LAN interface component and then straight to the WAN interface component without passing through the medical diagnostic logic. The encrypted diagnostic results (9.3) can then be sent to the remote services. As previously discussed, the encrypted diagnostic results (10.1), (10.2) may be separately sent to a medical diagnostic logic, which can then send them to an encrypted diagnostic results store (10.3). Depending on desired functionality, this store may be separate from the mobile device. Encrypted diagnostic results (11.1), (11.2) may also be sent from the medical diagnostic logic the remote services, via the WAN interface component.

In some embodiments, the remote services may request a diagnostic. As illustrated the remote services request a diagnostic (12.1), (12.2), (12.3), (12.4) which is relayed to the diagnostic device. This can prompt a diagnostic response (13.1), (13.2), (13.3), (13.4) that is relayed back to the remote services.

IX. S. Work Flows of the Diagnostic Assay System

FIGS. 47-52 are flow charts illustrating the functions of different aspects of a diagnostic assay system, such as the one illustrated in FIG. 38, according to some embodiments of the invention. As with other figures provided herein, FIGS. 47-52 are provided as non-limiting examples. Alternative embodiments may include additional functionality to that shown in the figure, and/or the functionality shown in the figure may be omitted, combined, separated, and/or performed simultaneously. Means for performing the functionality of the blocks may include one or more hardware and/or software components, such as those shown in FIG. 38 AND 53. A person of ordinary skill in the art will recognize some variations.

IX. T. Location Configuration Network Work Flow

Figure 47:
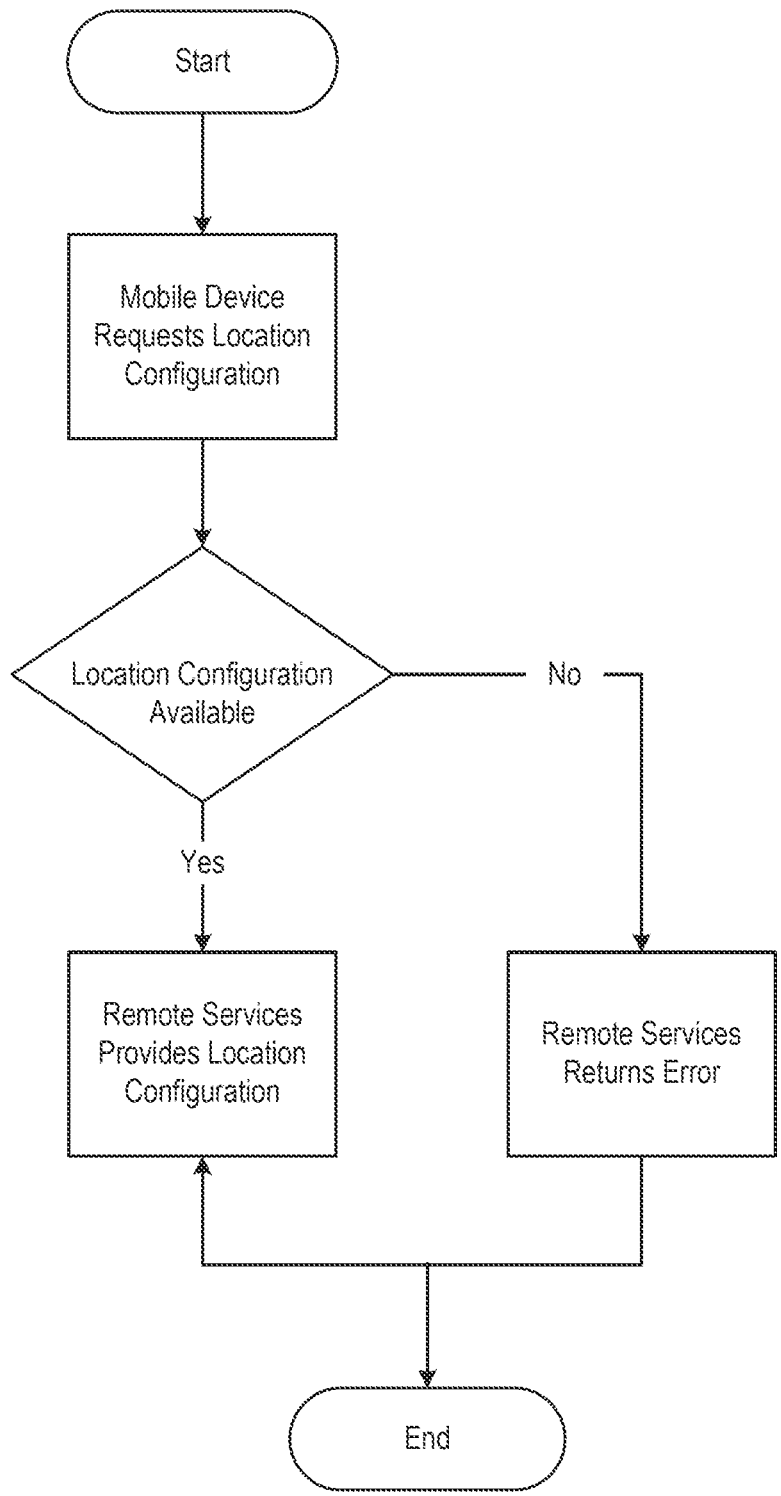
FIG. 47 is a data flow diagram illustrating the process for a location configuration of a diagnostic assay system, according to some embodiments of the invention.

FIG. 47 is a data flow diagram illustrating the process for a location configuration of a diagnostic assay system, according to an embodiment. Means for performing one or more blocks illustrated in FIG. 47 can include the remote services as described herein.

The process can start when a mobile device requests location configuration. As previously explained, example data flows for such a request are illustrated in FIGS. 45 and 46. If the location configuration is available, it is provided by the remote services. If not, the remote services return an error.

IX. U. Operational Updates Network Work Flow—Mobile Device

Figure 48:
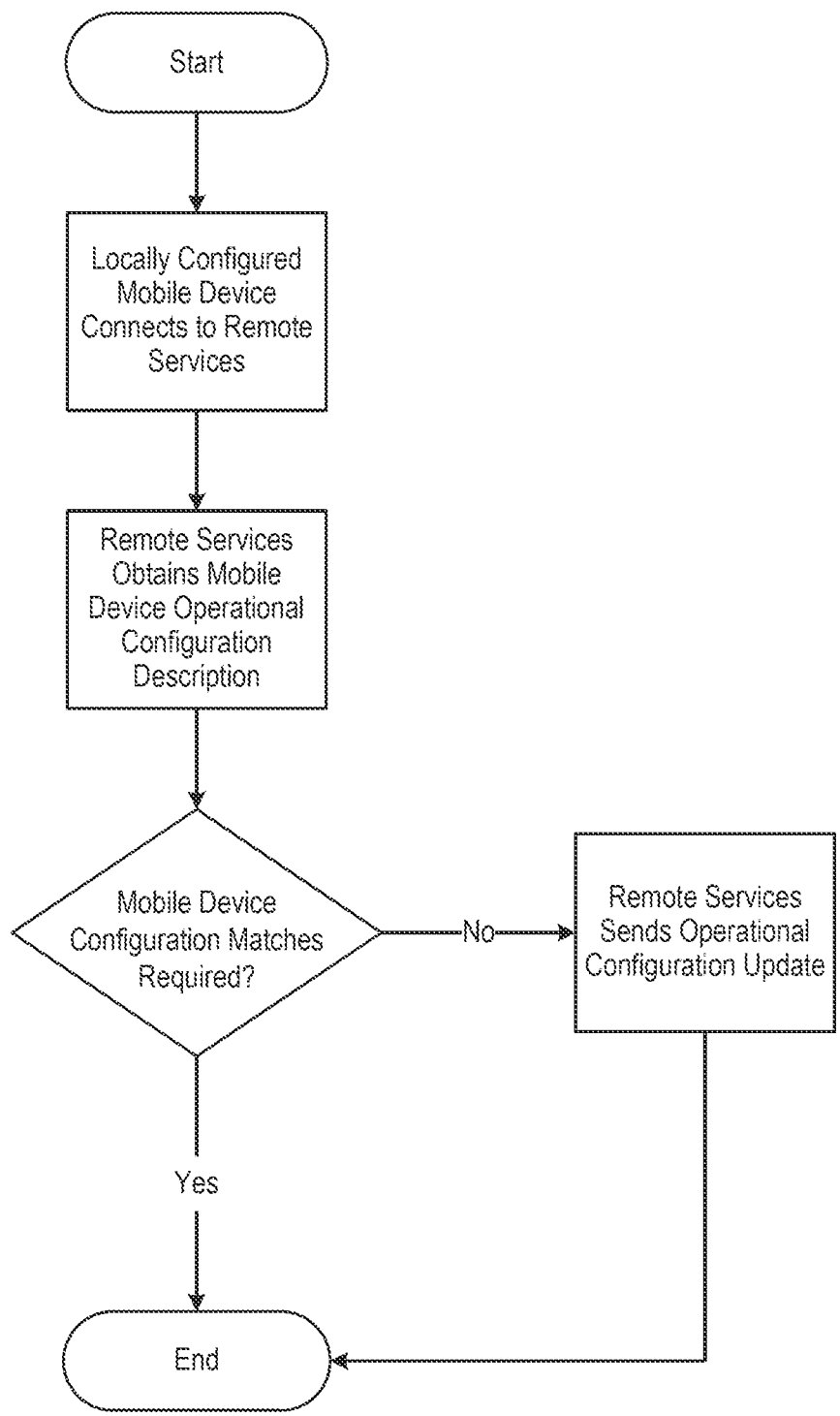
FIG. 48 is a data flow diagram illustrating the process for providing operational updates to a mobile device in a diagnostic assay system, according to some embodiments of the invention.

FIG. 48 is a data flow diagram illustrating the process for providing operational updates to a mobile device in a diagnostic assay system, according to some embodiments of the invention. Means for performing one or more blocks illustrated in FIG. 48 can include the remote services and/or mobile device as described herein.

The process can start when a locally configured mobile device connects to remote services. The remote services then obtain a description of the mobile device operational description. If the description matches the required mobile device configuration, the process can then end. Otherwise, the remote services send the mobile device an operational configuration update.

IX. V. Operational Updates Network Work Flow—Diagnostic Device

Figure 49:
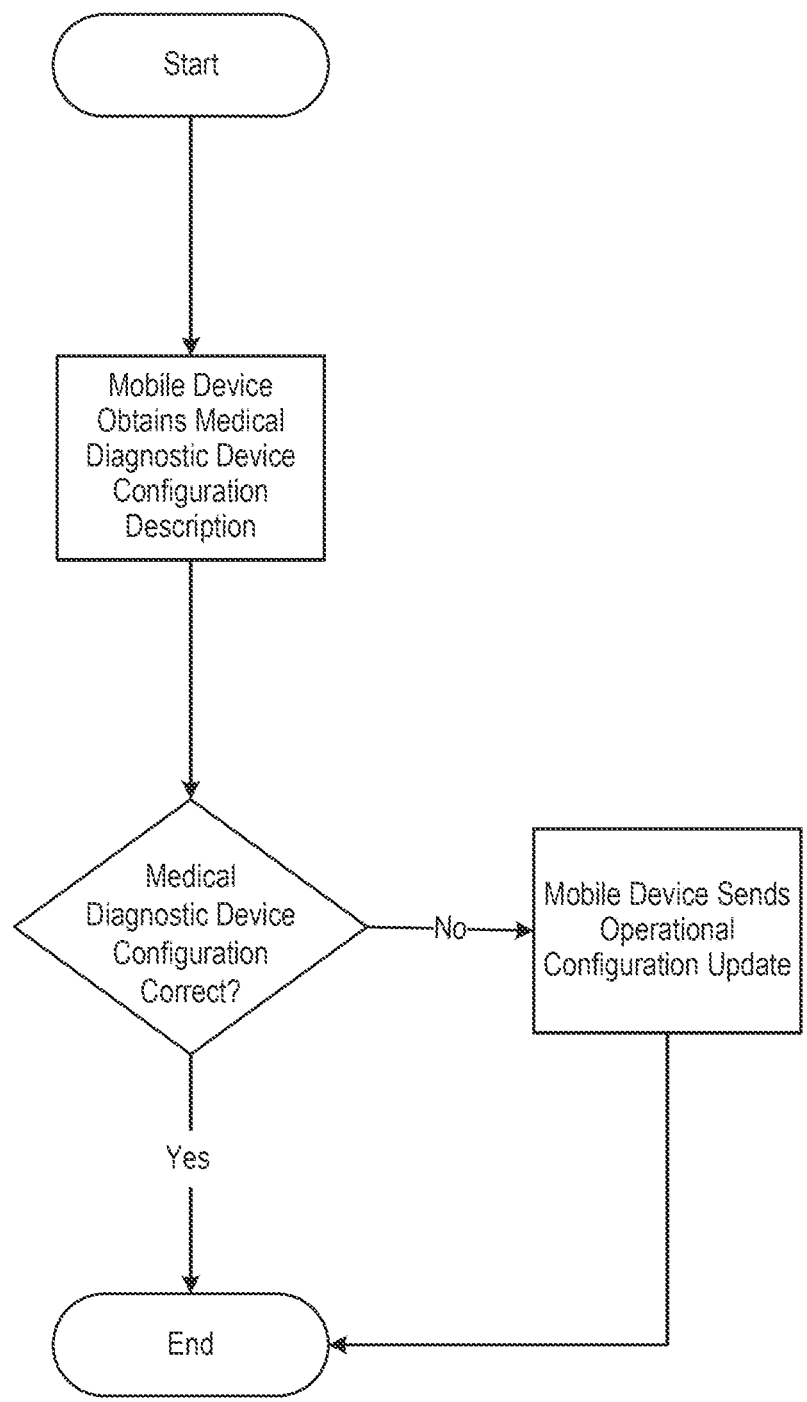
FIG. 49 is a data flow diagram illustrating the process for providing operational updates to a diagnostic device in a diagnostic assay system, according to some embodiments of the invention.

FIG. 49 is a data flow diagram illustrating the process for providing operational updates to a diagnostic device in a diagnostic assay system, according to some embodiments. Means for performing one or more blocks illustrated in FIG. 49 can include the mobile device and/or diagnostic device as described herein.

The process can start when the mobile device obtains a diagnostic device configuration description from the diagnostic device. If the diagnostic device configuration is correct, the process can end. Otherwise, the mobile device can send an operational configuration update to the diagnostic device.

IX. W. Remote Diagnostics Network Work Flow

Figure 50:
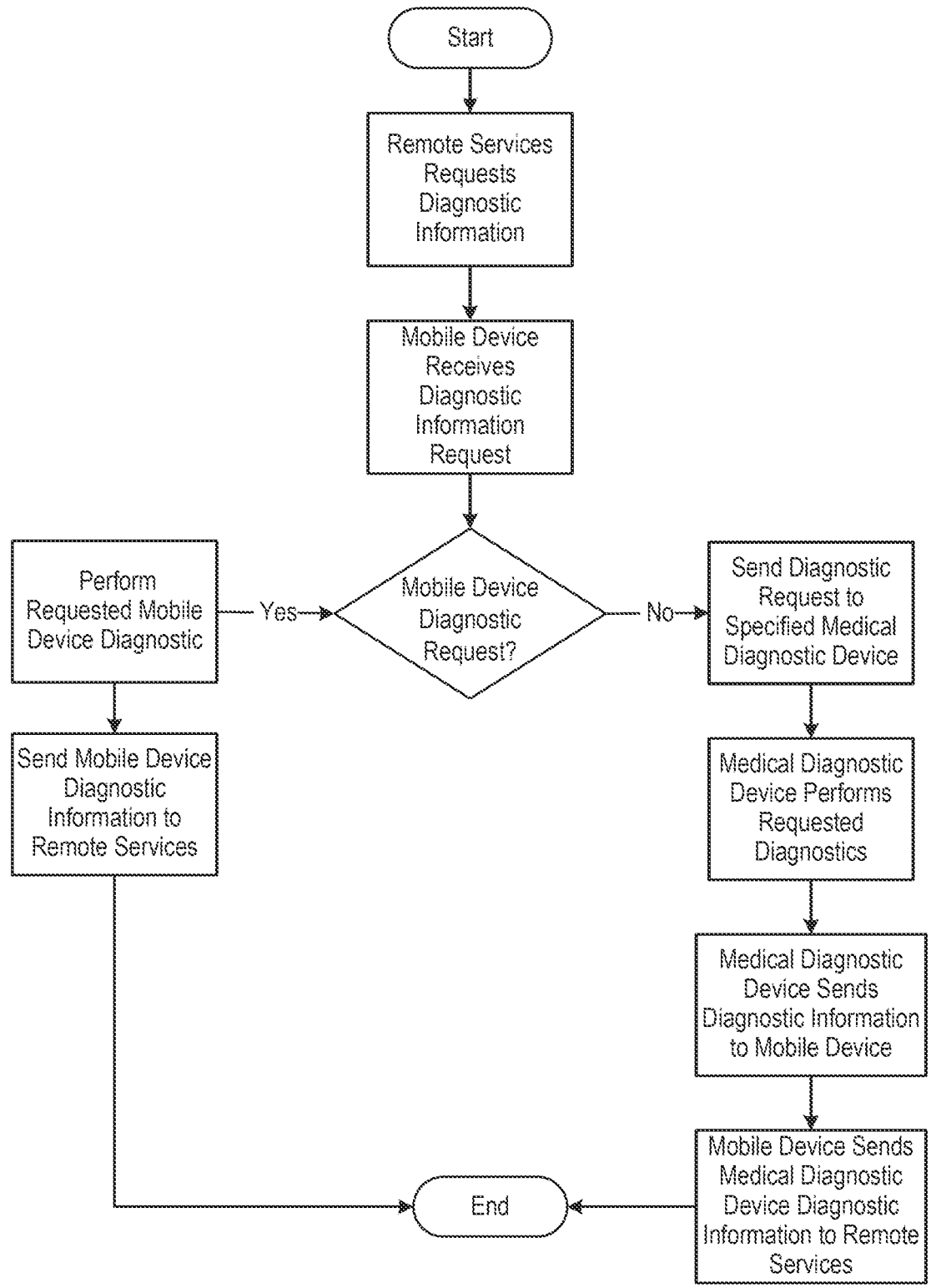
FIG. 50 is a data flow diagram of such a process in a diagnostic assay system, according to some embodiments of the invention.

As discussed above in relation to FIG. 46, remote services can request diagnostic information remotely. FIG. 50 is a data flow diagram of such a process in a diagnostic assay system, according to an embodiment. Means for performing one or more blocks illustrated in FIG. 50 can include the remote services, mobile device, and/or diagnostic device as described herein.

The process can start when remote services requests diagnostic information. The mobile device receives the diagnostic information request. If the diagnostic request is for the mobile device, the mobile device will perform the requested mobile device diagnostic and send the mobile device diagnostic information to the remote services. Otherwise, the diagnostic request is sent by the mobile device to the specified diagnostic device (which may be one of several at the site and/or communicatively linked with the mobile device). The diagnostic device then performs the requested diagnostics, and sends the diagnostic information to the mobile device. Finally, the mobile device sends the diagnostic device diagnostic information to the remote services.

IX. X. Medical Diagnostic Device Commands Network Work Flow

Figure 51:
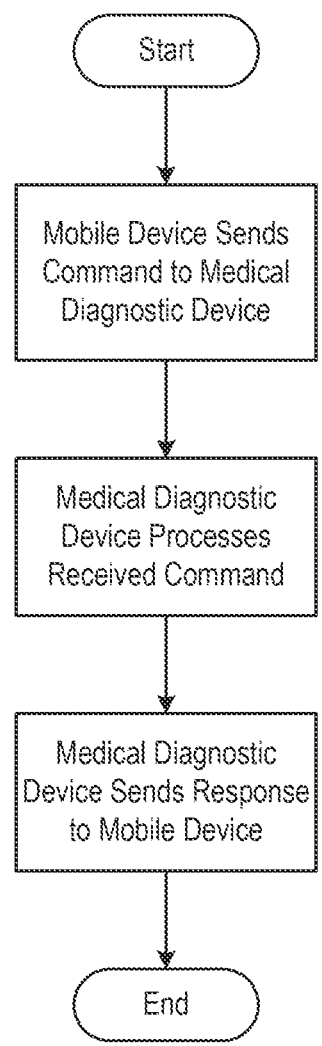
FIG. 51 is a data flow diagram illustrating the process for providing diagnostic device commands in a diagnostic assay system, according to some embodiments of the invention.

FIG. 51 is a data flow diagram illustrating the process for providing diagnostic device commands in a diagnostic assay system, according to some embodiments of the invention. Means for performing one or more blocks illustrated in FIG. 51 can include the mobile device and/or diagnostic device as described herein.

The process can start with the mobile device sending a command to a diagnostic device. The diagnostic device then processes the received command. Finally, the diagnostic device sends the response to the mobile device.

IX. Y. Diagnostic Device Registration Network Work Flow

Figure 52:
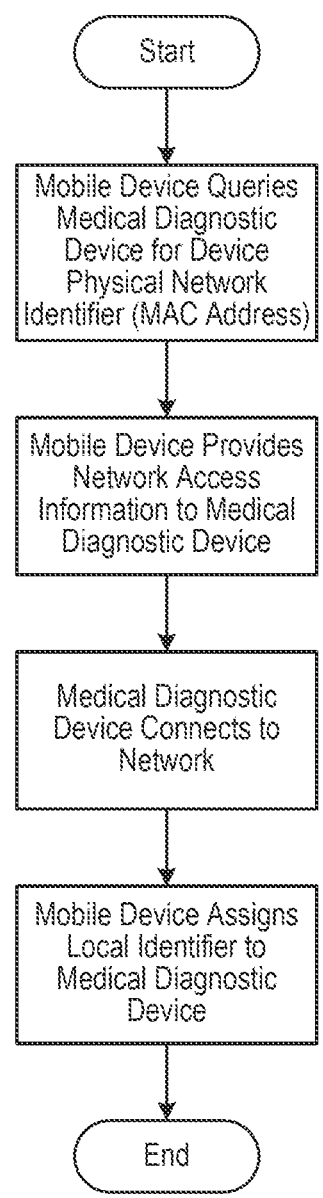
FIG. 52 is a data flow diagram illustrating the process for providing medical diagnostic device registration on a network of a diagnostic assay system, according to some embodiments of the invention.

FIG. 52 is a data flow diagram illustrating the process for providing diagnostic device registration on a network of a diagnostic assay system, according to some embodiments of the invention. Means for performing one or more blocks illustrated in FIG. 52 can include the mobile device and/or diagnostic device as described herein.

The process can start when the mobile device queries the diagnostic device for device physical network identifier, such as a MAC address. The mobile device then provides network access information to the diagnostic device as previously described herein. Such information can include an SSID, username, and the like. In some embodiments, as previously described, the communication between the mobile device and diagnostic device to this point may be via NFC and/or other wireless technologies. The diagnostic device then connects to the network, and the mobile device assigns a local identifier to the diagnostic device.

IX. Z. Computer System

Figure 53:
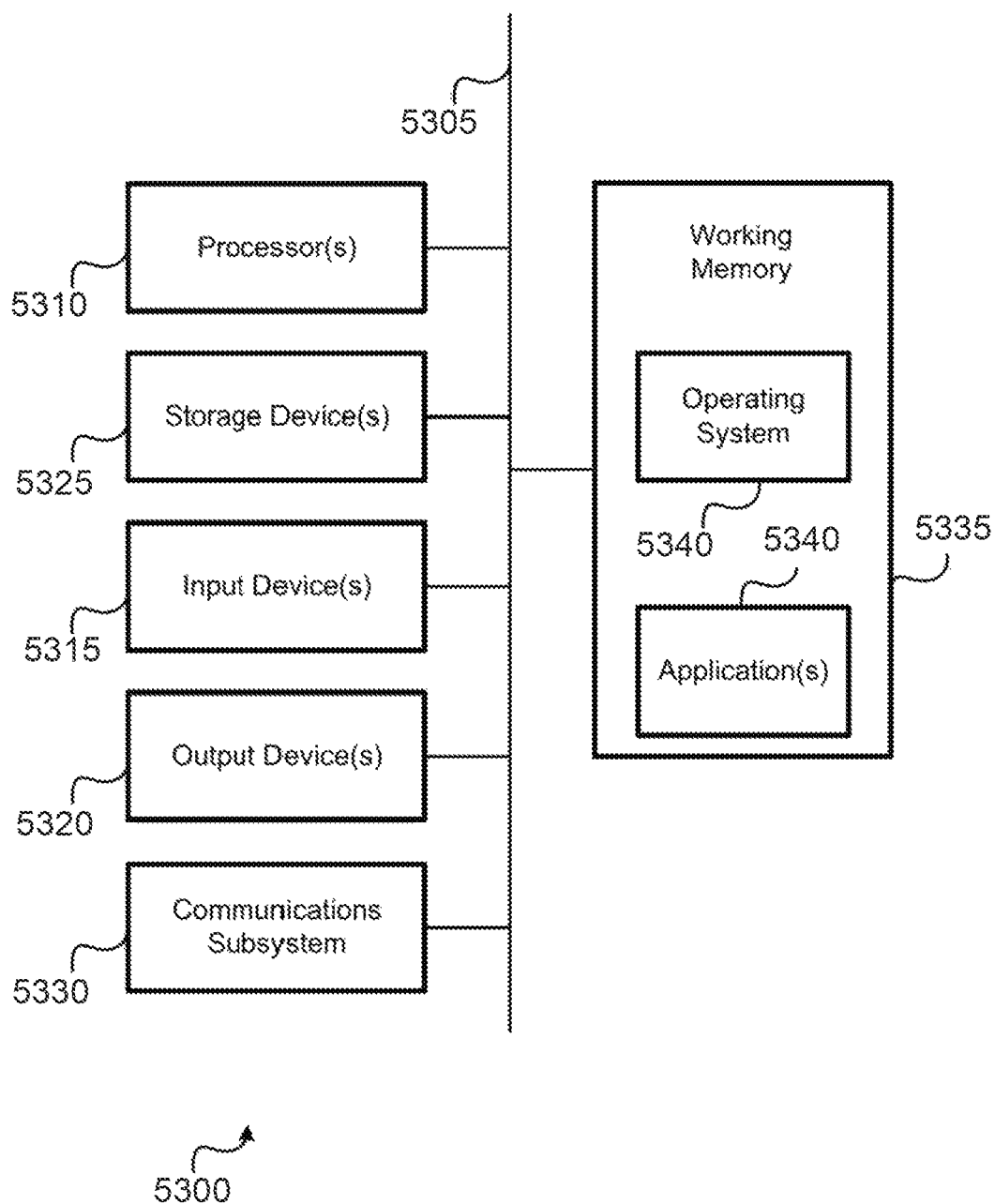
FIG. 53 is an illustration of a computer system, according to some embodiments of the invention, which can be incorporated, at least in part, into devices and components of the diagnostic assay system described herein.

FIG. 53 is an exemplary illustration of a computer system 5300, which can be incorporated, at least in part, into devices and components of the diagnostic assay system shown on FIG. 38, including the diagnostic device (Epsilon Instrument), mobile device (Epsilon Handheld Platform), and/or or remote services (Remote Xpert System and Remote Xpert+System). FIG. 53 provides a schematic illustration of a computer system 5300 that can perform the methods provided by various embodiments of the invention. It should be noted that FIG. 53 is meant only to provide a generalized illustration of various components, any or all of which can be utilized as appropriate.

The computer system 5300 is shown comprising hardware elements that can be electrically coupled via a bus 5306 (or may otherwise be in communication, as appropriate). The hardware elements can include a processing unit, such as processor(s) 5310, which can include without limitation one or more general-purpose processors, one or more special-purpose processors (such as digital signal processing chips, graphics acceleration processors, and/or the like), and/or other processing means; one or more input devices 5315, which can include without limitation a mouse, a keyboard, a camera, a microphone, a touchscreen, medical testing hardware and/or diagnostic components, and/or the like; and one or more output devices 5320, which can include without limitation a display device, a printer, and/or the like.

The computer system 5300 can further include (and/or be in communication with) one or more non-transitory storage devices 5325, which can comprise, without limitation, local and/or network accessible storage, and/or can include, without limitation, a disk drive, a drive array, an optical storage device, a solid-state storage device, such as a random access memory ("RAM"), and/or a read-only memory ("ROM"), which can be programmable, flash-updateable, and/or the like. Such storage devices can be configured to implement any appropriate data stores, including without limitation, various file systems, database structures, and/or the like.

In some embodiments, the computer system 5300 can include a communications subsystem 5330, which can include without limitation a modem, a network card (wireless or wired), an infrared communication device, a wireless communication device, and/or a chipset (such as an NFC transceiver, a Bluetooth device, an 802.11 device, a Wi-Fi device, a WiMax device, cellular communication transceiver, etc.), and/or the like. The communications subsystem 5330 can include one or more input and/or output communication interfaces to permit data to be exchanged with a network, other computer systems (e.g., using peer-to-peer communication, as described herein), and/or any other electrical devices described herein. In some embodiments, the computer system 5300 will comprise a working memory 5335, which can include a RAM or ROM device, as described above.

The computer system 5300 can comprise software elements, shown as being currently located within the working memory 5335, including an operating system 5340, device drivers, executable libraries, and/or other code, such as one or more application programs 5345, which can comprise computer programs provided by various embodiments (e.g., the mobile device software, interface software, etc.), and/or can be designed to implement methods and/or software architecture, as described herein. Merely by way of example, methods and/or architecture provided in the other figures appended hereto, might be implemented as code and/or instructions executable by a computer (and/or a processing unit within a computer); in an aspect, then, such code and/or instructions can be used to configure and/or adapt a general purpose computer (or other device) to perform one or more operations in accordance with the described methods.

A set of these instructions and/or code can be stored on a non-transitory computer-readable storage medium, such as the storage device(s) 5325 described above. In some embodiments, the storage medium can be incorporated within a computer system, such as computer system 5300. In some embodiments, the storage medium can be separate from a computer system (e.g., a removable medium, such as an optical disc), and/or provided in an installation package, such that the storage medium can be used to program, configure, and/or adapt a general purpose computer with the instructions/code stored thereon. These instructions can take the form of executable code, which is executable by the computer system 5300 and/or can take the form of source and/or installable code, which, upon compilation and/or installation on the computer system 5300 (e.g., using any of a variety of generally available compilers, installation programs, compression/decompression utilities, etc.), then takes the form of executable code.

It will be apparent to those skilled in the art that substantial variations can be made in accordance with specific requirements. For example, customized hardware can be used, and/or particular elements can be implemented in hardware, software (including portable software, such as applets, etc.), or both. Connection to other computing devices such as network input/output devices can be employed.

Some embodiments can employ a computer system (such as the computer system 5300) to perform methods in accordance with some embodiments of the invention. In some embodiments, some or all of the procedures of such methods are performed by the computer system 5300 in response to processor(s) 5310 executing one or more sequences of one or more instructions (which can be incorporated into the operating system 5340 and/or other code, such as an application program 5345) contained in the working memory 5335. Such instructions can be read into the working memory 5335 from another computer-readable medium, such as one or more of the storage device(s) 5325. Merely by way of example, execution of the sequences of instructions contained in the working memory 5335 can cause the processor(s) 5310 to perform one or more procedures of the methods described herein. Additionally or alternatively, portions of the methods described herein can be executed through specialized hardware.

The terms "machine-readable storage medium" and "computer-readable storage medium," as used herein, refer to any storage medium that participates in providing data that causes a machine to operate in a specific fashion. In some embodiments implemented using the computer system 5300, various computer-readable media can be involved in providing instructions/code to processor(s) 5310 for execution and/or can be used to store and/or carry such instructions/code. In some embodiments, a computer-readable storage medium is a physical and/or tangible storage medium. Such a medium can take the form of a non-volatile media or volatile media. Non-limiting examples of non-volatile media can include, optical and/or magnetic disks, such as the storage device(s) 5325. Non-limiting examples of volatile media can include, without limitation, dynamic memory, such as the working memory 5335.

Non-limiting common forms of physical and/or tangible computer-readable media can include, for example, a floppy disk, a flexible disk, hard disk, magnetic tape, or any other magnetic medium, a CD-ROM, any other optical medium, a RAM, a PROM, EPROM, a FLASH-EPROM, any other memory chip or cartridge, or any other medium from which a computer can read instructions and/or code.

Various forms of computer-readable media can be involved in carrying one or more sequences of one or more instructions to the processor(s) 5310 for execution. Merely by way of example, the instructions may initially be carried on a magnetic disk and/or optical disc of a remote computer. A remote computer can load the instructions into its dynamic memory and send the instructions as signals over a transmission medium to be received and/or executed by the computer system 5300.

The communications subsystem 5330 (and/or components thereof) generally will receive signals, and the bus 5306 then can carry the signals (and/or the data, instructions, etc. carried by the signals) to the working memory 5335, from which the processor(s) 110 retrieves and executes the instructions. The instructions received by the working memory 5335 can optionally be stored on a non-transitory storage device 5325 either before or after execution by the processor(s) 5310.

IX. Aa. Process Flow of Managing a Diagnostic Assay System

Figure 54:
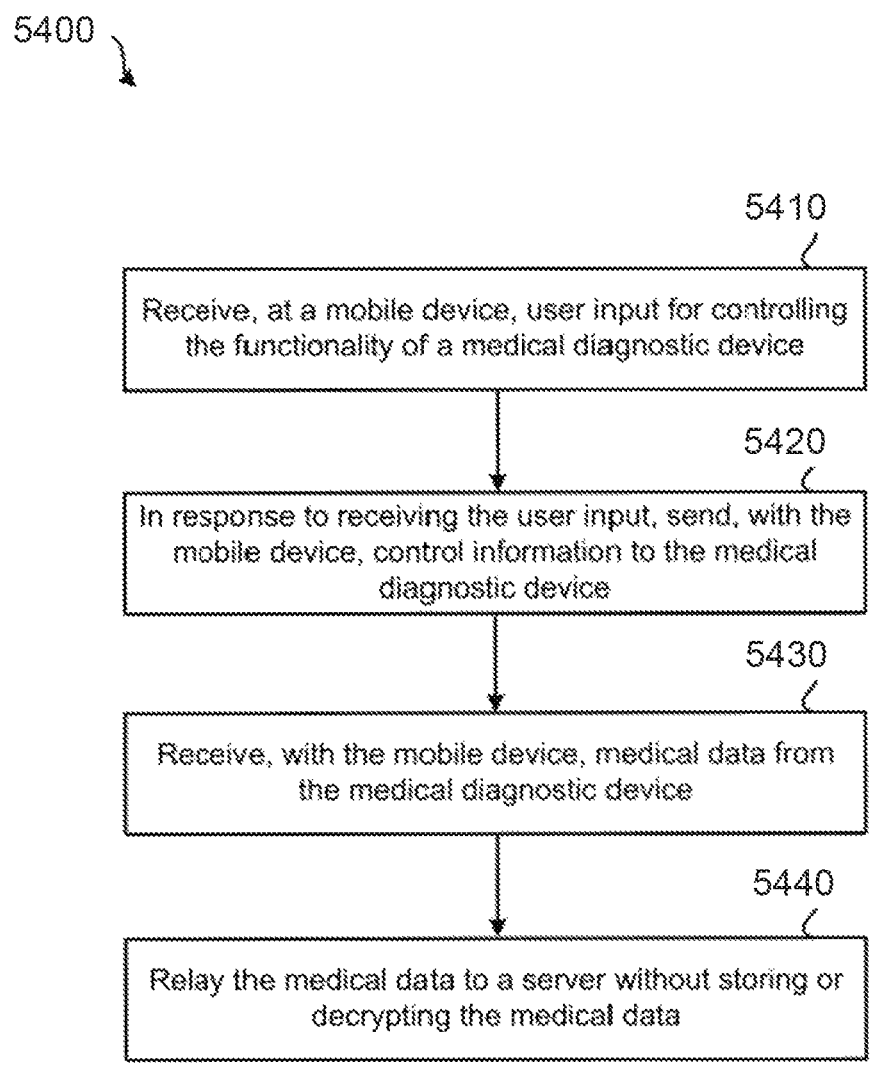
FIG. 54 is a flow diagram of a method of managing a diagnostic assay system with a mobile device, according to some embodiments of the invention.

FIG. 54 is a flow diagram 5400 of a method of managing a diagnostic assay system with a mobile device, according to some embodiments of the invention. As with other figures provided herein, FIG. 54 is provided as a non-limiting example. Some embodiments can include additional functionality to that shown in the figure, and/or the functionality shown in one or more of the blocks in the figure may be omitted, combined, separated, and/or performed simultaneously (or in close temporal proximity). Means for performing the functionality of the blocks can include a mobile device as described herein, which can implement one or more hardware and/or software components, such as those shown in FIG. 53. A person of ordinary skill in the art will recognize some variations that are suitable for use with the invention as disclosed herein.

At block 5410, the mobile device receives user input for controlling the functionality of a diagnostic device. As described earlier, the mobile device can execute a software application providing a GUI with which a user can control various functions of the diagnostic device, such as manage device settings of the diagnostic device; initiate, pause, or cancel medical tests conducted by the diagnostic device; specify the remote services to which the diagnostic device sends data; specify the type, content, and/or format of the data; and the like. At block 5420, in response to receiving the user input, the mobile device sends control information to the diagnostic device. If the mobile device is communicatively linked with a plurality of diagnostic devices, the mobile device may first need to select or identify the diagnostic device from the plurality of diagnostic devices.

At block 5430, the mobile device receives data from the diagnostic device. The data received may correspond to the type, content, and/or format of the data specified at block 5410 (if such features were specified). However, as indicated, the mobile device can act simply as a pass-through device by which the diagnostic device can communicate with a remote server (e.g., one or more remote services as shown on FIG. 101). In other words, the mobile device can act as a transparent bridge, connecting a LAN (which may be peer-to-peer connected, as described herein) to a WAN. But, as specified at block 5440, the received data can be relayed to the server without storing or decrypting the data, thereby helping ensure sensitive patient data is not compromised by the mobile device.

The methods, systems, and devices discussed above are examples. Various configurations can omit, substitute, or add various procedures or components as appropriate. For instance, in alternative configurations, the methods can be performed in an order different from that described, and/or various stages can be added, omitted, and/or combined. Also, features described with respect to certain configurations can be combined in various other configurations. Different aspects and elements of the configurations can be combined in a similar manner. Also, technology evolves and some of the elements as described are provided as non-limiting examples and thus do not limit the scope of the disclosure or claims.

Specific details are given in the description to provide a thorough understanding of exemplary configurations (including implementations). However, configurations can be practiced without these specific details. For example, well-known circuits, processes, algorithms, structures, and techniques have been shown without unnecessary detail in order to avoid obscuring the configurations. This description provides exemplary configurations that do not limit the scope, applicability, or configurations of the claims. Rather, the preceding description of the configurations will provide those skilled in the art with an enabling description for implementing described techniques. Various changes can be made in the function and arrangement of elements without departing from the spirit or scope of the disclosure.

Also, configurations can be described as a process which is depicted as a flow diagram or block diagram. Although each can describe the operations as a sequential process, some of the operations can be performed in parallel or concurrently. Furthermore, examples of the methods can be implemented by hardware, software, firmware, middleware, microcode, hardware description languages, or any combination thereof. When implemented in software, firmware, middleware, or microcode, the program code or code segments to perform the necessary tasks can be stored in a non-transitory computer-readable medium such as a storage medium. Processors can perform the described tasks.

Terms, "and" and "or" as used herein, may include a variety of meanings that also is expected to depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein may be used to describe any feature, structure, or characteristic in the singular or may be used to describe some combinations of features, structures, or characteristics. However, it should be noted that this is merely an illustrative example and claimed subject matter is not limited to this example. Furthermore, the term "at least one of" if used to associate a list, such as A, B, or C, can be interpreted to mean any combination of A, B, and/or C, such as A, AB, AA, AAB, AABBCCC, etc.

Having described several exemplary configurations, various modifications, alternative constructions, and equivalents can be used without departing from the spirit of the disclosure. For example, the above elements can be components of a larger system, wherein other rules can take precedence over or otherwise modify the application of the invention. Also, a number of steps can be undertaken before, during, or after the above elements are considered. Accordingly, the above description does not bound the scope of the claims.

All patents, patent applications, and other publications cited in this application are incorporated by reference in their entirety for all purposes.

What is claimed is:

1. A system for operating a valve drive mechanism, the system comprising:
 a valve drive mechanism chassis;
 a brushless DC (BLDC) motor coupled to the chassis, wherein the BLDC motor comprises a plurality of hall-effect sensors and does not include any encoder hardware;
 a transmission coupled to BLDC motor; and
 a valve drive coupled to the transmission, the valve drive configured to rotate positions of a valve body of a removable assay cartridge,
 wherein position of the valve drive output is determined based on analyzing a sinusoidal signal generated by the hall-effect sensors, and
 wherein the BLDC motor is configured to monitor cartridge integrity based a current measurements of a bridge circuit of the BLDC motor, the current draw measurements being associated with events indicating loss of integrity of the removable assay cartridge.

2. The system of claim 1, wherein the transmission comprises a first worm drive gear set directly attached to an output shaft of the BLDC motor, and a second worm drive gear set coupled between the first worm drive gear set and the valve drive output.

3. The system of claim 1, wherein the BLDC motor is located at a bottom side of the valve drive chassis and the valve drive output is located a top side of the valve drive chassis.

4. The system of claim 1, wherein the valve drive comprises a turntable.

5. The system of claim 1, wherein the BLDC motor is configured to home and center position of the valve drive output by performing a centering protocol based on the sinusoidal signal generated by the hall-effect sensors.

6. A method for operating a valve drive mechanism, the method comprising:
 receiving a command to power a brushless DC (BLDC) motor coupled to the chassis to move a valve drive to a particular position, the valve drive being configured to rotate positions of a valve body of a removable assay cartridge,
 wherein a transmission coupled between the BLDC motor and the valve drive and wherein the BLDC motor comprises a plurality of hall-effect sensors that does not include any encoder hardware;
 powering the BLDC motor in response to rotate a shaft of the BLDC motor a particular number of turns to move the valve drive to the particular position based on a sinusoidal signal generated by the hall-effect sensors, and
 wherein the BLDC motor is configured to home and center position of the valve drive output by performing a centering protocol based on the sinusoidal signal generated by the hall-effect sensors.

7. The method of claim 6, wherein the transmission comprises a first worm drive gear set directly attached to an output shaft of the BLDC motor, and a second worm drive gear set coupled between the first worm drive gear set and the valve drive output.

8. The method of claim 6, wherein the valve drive comprises a turntable.

9. The method of claim 6, wherein the BLDC motor is configured to monitor cartridge integrity based a current measurements of a bridge circuit of the BLDC motor, the current draw measurements being associated with events indicating loss of integrity of the removable assay cartridge.

* * * * *